US009012616B2

(12) United States Patent
Apt et al.

(10) Patent No.: US 9,012,616 B2
(45) Date of Patent: Apr. 21, 2015

(54) POLYNUCLEOTIDE FOR IMPROVING PROTEIN PRODUCTION IN MICROORGANISMS OF THE PHYLUM LABYRINTHULOMYCOTA

(71) Applicant: DSM IP Assets B.V., Te Heerlen (NL)

(72) Inventors: Kirk E. Apt, Ellicott City, MD (US); James Casey Lippmeier, Columbia, MD (US); David Simpson, Boulder, CO (US); Jun Wang, Cooksville, MD (US); James P. Wynn, Okemos, MI (US); Ross Zirkle, Mount Airy, MD (US)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 14/108,794

(22) Filed: Dec. 17, 2013

(65) Prior Publication Data

US 2014/0106402 A1 Apr. 17, 2014

Related U.S. Application Data

(62) Division of application No. 12/724,403, filed on Mar. 15, 2010, now Pat. No. 8,637,651.

(60) Provisional application No. 61/290,441, filed on Dec. 28, 2009, provisional application No. 61/160,618, filed on Mar. 16, 2009.

(51) Int. Cl.
| | |
|---|---|
| *C07H 21/04* | (2006.01) |
| *C12N 1/13* | (2006.01) |
| *C12P 21/02* | (2006.01) |
| *C07K 14/37* | (2006.01) |
| *C12N 15/80* | (2006.01) |
| *C12P 21/00* | (2006.01) |
| *C12R 1/90* | (2006.01) |

(52) U.S. Cl.
CPC .............. *C12P 21/00* (2013.01); *C07K 14/37* (2013.01); *C12N 15/80* (2013.01); *C12R 1/90* (2013.01)

(58) Field of Classification Search
USPC .............................. 536/23.1; 435/257.2, 69.1
See application file for complete search history.

(56) References Cited

U.S. PATENT DOCUMENTS

| | | | |
|---|---|---|---|
| 3,223,456 | A | 12/1965 | Sonnerischein |
| 4,381,897 | A | 5/1983 | Arbeletche et al. |
| 4,626,505 | A | 12/1986 | Falco |

(Continued)

FOREIGN PATENT DOCUMENTS

| | | |
|---|---|---|
| BE | 545283 | 3/1956 |
| DE | 195 29 475 A1 | 2/1997 |

(Continued)

OTHER PUBLICATIONS

Model document for preparing Statement for biological deposit in compliance with terms of Budapest Treaty, Feb. 19, 2014.*

(Continued)

*Primary Examiner* — Rosanne Kosson
(74) *Attorney, Agent, or Firm* — Xi Chen; Shannon McGarrah

(57) ABSTRACT

The present invention relates to recombinant cells and microorganisms of the phylum Labyrinthulomycota and their use in heterologous protein production. Novel promoter, terminator, and signal sequences for efficient production and, optionally, secretion of polypeptides from recombinant host cells and microorganisms are also encompassed by the present invention.

22 Claims, 45 Drawing Sheets

(56) References Cited

U.S. PATENT DOCUMENTS

| | | | |
|---|---|---|---|
| 5,130,242 A | 7/1992 | Barclay | |
| 5,340,742 A | 8/1994 | Barclay | |
| 5,426,040 A | 6/1995 | Cheney et al. | |
| 5,576,428 A | 11/1996 | Butler et al. | |
| 5,605,011 A | 2/1997 | Bedbrook et al. | |
| 5,661,017 A | 8/1997 | Dunahay et al. | |
| 5,804,408 A | 9/1998 | Hagiwara et al. | |
| 5,824,309 A | 10/1998 | Dassarma et al. | |
| 5,853,973 A | 12/1998 | Kakefuda et al. | |
| 6,027,900 A | 2/2000 | Allnutt et al. | |
| 6,419,425 B1 | 7/2002 | Fourcroy et al. | |
| 7,001,772 B2 | 2/2006 | Roessler et al. | |
| 7,029,872 B2 | 4/2006 | Gerngross | |
| 7,332,299 B2 | 2/2008 | Hamilton | |
| 7,625,756 B2 | 12/2009 | Hamilton | |
| 7,759,097 B2 | 7/2010 | Ono et al. | |
| 7,851,191 B2 | 12/2010 | Roessler et al. | |
| 7,888,123 B2 | 2/2011 | Ono et al. | |
| 8,003,772 B2 | 8/2011 | Weaver et al. | |
| 2002/0156254 A1 | 10/2002 | Qiu et al. | |
| 2002/0194641 A1 | 12/2002 | Metz et al. | |
| 2003/0166207 A1 | 9/2003 | Roessler et al. | |
| 2005/0112719 A1 | 5/2005 | Roessler et al. | |
| 2006/0029604 A1 | 2/2006 | Gerngross et al. | |
| 2006/0040353 A1 | 2/2006 | Davidson et al. | |
| 2006/0257399 A1 | 11/2006 | Gerngross et al. | |
| 2007/0128222 A1 | 6/2007 | Kovacs et al. | |
| 2007/0270494 A1 | 11/2007 | Metz et al. | |
| 2009/0053784 A1 | 2/2009 | Travassos-Leandro et al. | |
| 2009/0064567 A1 | 3/2009 | Lippmeier et al. | |
| 2009/0192304 A1 | 7/2009 | Roessler et al. | |
| 2011/0086390 A1 | 4/2011 | Roessler et al. | |
| 2011/0189228 A1 | 8/2011 | Bayne et al. | |
| 2011/0195448 A1 | 8/2011 | Lippmeier et al. | |
| 2011/0195449 A1 | 8/2011 | Lippmeier et al. | |
| 2011/0195480 A1 | 8/2011 | Apt | |

FOREIGN PATENT DOCUMENTS

| | | |
|---|---|---|
| EP | 0257 993 A2 | 3/1988 |
| EP | 0922766 A1 | 6/1999 |
| JP | 2007-524377 | 8/2007 |
| LU | 35839 | 2/1958 |
| WO | WO 00/58485 A1 | 10/2000 |
| WO | WO 00/73455 A1 | 12/2000 |
| WO | WO02/083869 | 10/2002 |
| WO | WO 2008/129358 A2 | 10/2008 |
| WO | WO2008/144473 | 11/2008 |
| WO | WO 2009/009876 A1 | 1/2009 |
| WO | WO 2009/101160 A1 | 8/2009 |
| WO | WO 2009/126843 A2 | 10/2009 |
| WO | WO2011/090731 | 7/2011 |

OTHER PUBLICATIONS

Result 1, search of instant SEQ ID No. 43 in the EST database, *M. musculus* molissmus clone No. 1-217G24.T7, on Feb. 12, 2014.*
Al-Ghamdi, M., "The anti-inflammatory, analgesie and antipyrectic activity of *Nigella sativa*," *J. Ethnopharmacol.* 76:45-48, Elsevier, Ireland (2001).
Ali, B. and Geald, B., "Pharmacological and toxicological properties of *Nigella sativa*," *Phytother, Res.* 17:299-305, Wiey, United Kingdom (2003).
Altschul, S., et al., "Gapped BLAST and PSI-BLAST: a new generation of protein database search programs,"*Nucleic Aids Res.* 25:3389-3402, Oxford University Press, United Kingdom (1997).
Apt, K., et al., "In vivo characterization of diatom multipartite plastid targeting signal," *J. Cell Sci.* 115:4061-4069, Company of Biologist, England (2002).
Armaleo, D., et al., "Biohstic Nuclear transformation of *Saccharomyces cerevisiae* and other fungi," *Curr. Genet.* 17.97-103, Springer International United States, 1990.
Bekkaoui, F., et al., "Isolation and structure of an aceolactate synthase gene from *Schzosaccharomyces pombe* and complementation of the ilv2 mutation in *Saccharomyces cerevislae*," *Curr. Gen.* 24:544-547, Springer International, United States (1993).
Branden, C. and Tooze, J., "Prediction, Engineering, and Design of Protein Structures," *Introduction to Protein Structure*. $1^{st}$ ed., p. 247, Garland Publishing Inc., United States (1991).
Chang, A.K. and Duggleby, R.G., "Herbicide-resistant forms of *Arabidopis thallana* acetohydroxyacid synthase: characterization of the catalytic properties and sensitivity to inhibitors of four defined mutant." *Biochem. J.* 333:765-777, The Biochemical Society, Great Britain (1998).
Chatdumrong, W., et al., "Optimization of Docosahexacnoic Acid (DHA) Production and Improvement of Astxanthun Content in a Mutant *Schizochytrium Ilmacinum* Isolated from Mangrove Forest in Thailand," *Kasersart Journal: Natural Science* 41(2):324-334, Kasetsart Universoty, Thailand (2007).
Chipman, D., et al., "Biosynthesis of 2-aceto-2-hydroxy acids: acetolaciate synthases and acetohydroxyacid synthases," *Biochem. Biophys. Acta.* 1385:401-419, Elsevier Science B.V., Netherlands (1998).
Chong, C.-K. and Choi, J.-D., "Amino Acid Residues Conferring Herbicide Tolerance in Tobacco Acetolactate Synthase," *Biochem. Biophys. Res. Commun.* 279:462-467, Academic Press, United States (2000).
Drocourt, D., et al., "Cassettes of the *Strepioalloteichushindustanible* gene for Transformation of lower and higher eukaryotes to phleomycin resistance," *Nucl. Acids Res.* 18(13):4009, Oxford University Press, England (1990).
Falco, S.C., et al., "Nucleotide sequence of the yeast ILV2 gene which encodes acetolactate synthae," *Nucl. Acids Res.* 13(11):4011-4027, IRL Press Limited, England (1985).
Floss, D., et al., "Production of vaccines and therapeutic antibodies for veterinary appliocations in transgenic plants: an overview," *Transgenic Res.* 13(3):315-332, Chapman & Hall, Nethelands (2007).
Fuhrmann, M. "Production of Antigens in *Cholmydomonas reinharditt*; Green Microalgaeas a Novel Source of Recombinant Protein," *Methods in Molecular Medicine* 94:191-195, Humana Press, United States (2004).
Gatignol, A., et al., "Cloning of *Saccharomyces cerevisae* promoters using a probe vector based on phleomycin resistance," *Gene* 91:35-41, Elsevier Science Publishers B.V., Netherlands (1990).
Guerrero, C., et al., "The bleomycin resistance gene of transposen Tn5 is an excellent marker for transformation of corynebacteria," *Appl. Mircobiol. Biotechnol.* 36:759-762, Springer-Verlag, Germany (1992).
Hajhashemi, et al., "Black cumin seed essential oil, as a potential analgesic and anti-inflammatory drug," *Phytother. Res.* 18:195-199, Wiley, United Kingdom (2004).
Hill, C.M. and Duggleby, R.G., "Mutagensis of *Escherichia coli* acetohydroxyacid synthase isoenzyme II and characterization three herbicide-insensitive forms," *Biochem. J.* 335:653-661. The Biochemical Society, Great Britain (1998).
Ibdah, M., et al., "Homology Modeling of the Structure of Bacterial Acetohydroxy Acid Sythase and Examination of the Active Site by Site-Directed Mutagenesis," *Biochemistry* 35:16282-16291, American Chemical Society, United States (1996).
Joensuu, J., et al., "Transgenic plants for animal health: plant-made vaccine antigens for animal infectious disease control," *Phytochem Rev.* 7:553-577, Springer Science, United States (2008).
Kaestner, K., et al., "Universal beta-gulactosidase cloning vectors for promotor analysis and gene targetting," *Gene* 148:67-70, Elsevier, Netherlands (1994).
Li, Q., et al., "Screening and Characterization of Squalene-Producing Thraustochytrids from Hong Kong Mangroves," *J. Agric. Food. Chem.* 57(10):4267-4272, American Chemical Society, United States (2009).
Lewis, T.E., et al., "The Biotechnological Potential of Thraustochytrids," *Marine Biotechnology* 1(6):580-587, Springer-Verlag New York Inc., United States (1999)(Abstract Only).
Mazur, B.J. and Falco, C.S., "The Development of Herbicide Resistant Crops," *Annu. Rev. Plan Physiol. Plant Mol. Biol.* 40:441-470, Annuak Reviews Inc, United States (1989).

(56) References Cited

OTHER PUBLICATIONS

Meinkoth, J. and Wahl, G., "Hybridization of nucleic acids immobilzed on solid support," *Anal. Biochem.* 138:267-284, Academic Press, US (1984).
NCBI Entrez, GenBank Report, Accession No. AJ875406.1 Leandro, M.J., et al., Entry Date Oct. 24, 2006.
NCBI Entrez, GenBank Report, Accession No. Q11199, Cermakian, N., et al., Entry Date Oct. 31, 2006 (this sequence replaced Accession No. 2148078 on Sep. 14, 2005).
NCBI Entrez, GenBank Report, Accession No. MI3616, MacKay, R.M. and Doolittle, W.F., Entry Date Oct. 14, 2994.
NCBI Entrez, GenBank Report, Accession No. X06104, MacKay, R.M. and Doolittle, W.F., Entry Date Jun. 6, 2003.
Perez, P., et al., "Phleomycin resistance as a dominant selectable marker for plant cell transformation" *Plant Molecular Biology* 13:365-373, Kluwer Academic Publishers, Belgium (1989).
Prasad, V., et al., "Expression of biologically active Hemagglutinin-neuraminidase protein of Peste de petits ruminants virus in transgenic pigeonpea [*Cajanus cajan (L) Millsp.*]," *Plant Sci.* 166(1):199-205, Elsevier, Netherlands (2004).
Salem, M., "Immunodulatory and therapeutic properties of the *Nigella sativa* L. seed," *Int Immunopharmacol.* 5:1749-1770, Elsevier, Netherlands (2005).
Sanford, J.C., et al., "Optimizing the Biolistic Process for Different Biological Applications," *Methods Enzymol.* 217:483-509, Academic Press, Inc., United States (1993).
Sefernick, J.L., et al., "Melamine Deaminase and Atrazine Chlorohydrolase: 98 Percent Identical but Functionally Different," *J. Bacteriol.* 183(8).2405•2410, American Society for Microbiology, United States (2001).
Sim, J., et al., "Expression and Characterization of Synthetic Heat-Labile Enterotoxin B Subunit and Hemagglutinin-Neuraminidase-Neutralizing Epitope Fusion Protein in *Escherichia coli* and Tobacco Chloroplasts," *Plant Mol. Biol.* 27:388-399, Springer Science, United States (2009).
Siripornadulsil, S., et al., "Microalgal Vaccines," *Adv. Exp. Med. Biol.* 616:122-128, Plenum Press, United States (2007).
Spychalla, J.P., et al., "Indentification of an animal ⊙-3 fatty acid desaturase by heterologous expression in *Arabidopis," Proc. Natl. Acad. Sci. USA* 94:1142-1147, The National Academy of Sciences of the USA, United States (1997).
Tanabayahsi, K., et al., "Expression of mumps virus gylcoproteins in mammalian cells from cloned cDNAs: both F and HN proteins are required for cell fusion," *Virology* 187(2):801-804, Academic Press, United States (1992).
Tatusova, T. and Madden, T., "BLAST 2 sequences, a new tool for comparing protein and nucleotide sequences," *FEMS Microbiol. Lett.* 174:247-250, Blackwell Publishers, United Kingdom (1999).
Tekeoglu, I., et al., "Effects of theymoquinone (volatile oil for black cumin) on rheumatoid arthritis in rat models," *Phytother. Res.* 21:895-897, Wiley, United Kingdom (2007).
Supplementary European Search Report for European Application No. EP 02 71 9515, European Patent Office, Munich, Germany, complete on Nov. 12, 2004.
International Search Report for International Application No. PCT/US02/12040, United States Patent Office, Alexandria, Virginia, United States, mailed on Nov. 23, 2003.
International Search Report for International Patent Application No. PCT/US2010/62277, International Searching Authority, Alexandria, VA, mailed Mar. 9, 2011, 3 pages.
International Search Report for International Patent Application No. PCT/US2010/62275, International Searching Authority, Alexandria, VA, mailed Jun. 7, 2011, 4 pages.
International Search Report for International Patent Application No. PCT/US2010/62276, International Searching Authority, Alexandria, VA, mailed May 6, 2011, 6 pages.
International Search Report for International Patent Application No. PCT/US10/27352, International Searching Authority, Alexandria, VA, mailed Aug. 10, 2010, 4 pages.

* cited by examiner

MANIMANVTPQGVAKGFGLFVGVLFFLY

WFLVGLA (SEQ ID NO:1)

FIG. 1 atggccaaca tcatggccaa cgtcacgccc cagggcgtcg ccaagggctt tggcctcttt    60
gtcggcgtgc tcttctttct ctactggttc cttgtcggcc tcgcc    105

(SEQ ID NO:2)

FIG. 2 ccgcgaatcaagaaggtaggcgcgctgcgaggcgcggcggcggagcggagcgagggagagggagaggga
gagagagggagggagacgtcgccgcggcggggcctggcctggcctggtttggcttggtcagcgcggccttgtc
cgagcgtgcagctggagttgggtggattcatttggatttctttgttttgttttctctctttcccggaaagtgttgg
ccggtcggtgttctttgttttgatttcttcaaaagttttggtggttggttctctctcttggctctctgtcaggcggtccg
gtccacgccccggcctctcctctcctcctctcctcctctccgtgcgtatacgtacgtacgtttgtatacgtaca
tacatcccgccgccgtgccggcgagggtttgctcagcctggagcaatgcgatgcgatgcgatgcgatgcgac
gcgacgcgacgcgagtcactggttcgcgctgtggctgtggcttgcttgcttacttgctttcgagctctcccgcttc
ttctttccttctcacgccaccaccaacgaaagaagatcggccccggcacgccgctgagaagggctggcggcga
tgacggcacgcgcgcccgctgccacgttggcgctcgctgctgctgctgctgctgctgctgctgctgctgctgc
tgctgcttctgcgcgcaggctttgccacgaggccggcgtgctggccgctgccgcttccagtccgcgtggaga
gatcgaatgagagataaactggatggattcatcgagggatgaatgaacgatggttggatgccttttccttttc
aggtccacagcgggaagcaggagcgcgtgaatctgccgccatccgcatacgtctgcatcgcatcgcatcgcat
gcacgcatcgctcgccgggagccacagacgggcgacagggcggccagccagccaggcagccagccaggca
ggcaccagagggccagagagcgcgcctcacgcacgcgccgcagtgcgcgcatcgctcgcagtgcagaccttg
attccccgcgcggatctccgcgagcccgaaacgaagagcgccgtacgggcccatcctagcgtcgcctcgcacc
gcatcgcatcgcatcgcgttccctagagagtagtactcgacgaaggcaccatttccgcgctcctcttcggcgcga
tcgaggcccccggcgccgcgacgatcgcggcggccgcggcgctggcggcggccctggcgctcgcgctggcgg
ccgccgcgggcgtctggccctggcgcgcgcgggcgccgcaggaggagcggcagcggctgctcgccgccaga
gaaggagcgcgccgggcccggggagggacggggaggagaaggagaaggcgcgcaaggcggccccgaaa
gagaagaccctggacttgaacgcgaagaagaagaagaaggagaagaagttgaagaagaagaagaagaag
gagaggaagttgaagaagacgaggagcaggcgcgttcaaggcgcgttctcttccggaggcgcgttccagct
gcggcggcggggcgggctgcggggcgggcgcgggcgcgggtgcgggcagaggggacgcgcgcgcggagg
cggaggggccgagcgggagcccctgctgctgcggggcgcccgggccgcaggtgtggcgcgcgcgacgacg
gaggcgacgacgccagcggccgcgacgacaaggccggcggcgtcggcgggcggaaggccccgcgcggag
caggggcgggagcaggacaaggcgcaggagcaggagcagggccgggagcgggagcgggagcgggcggc
ggagcccgaggcagaacccaatcgagatccagagcgagcagaggccggccgcgagcccgagcccgcgccg
cagatcactagtaccgctgcggaatcacagcagcagcagcagcagcagcagcagcagcagcagcagcagca
gccacgagagggagataaagaaaaagcggcagagacg (SEQ ID NO:3)

FIG. 3

| | |
|---|---|
| gatccgaaag tgaaccttgt cctaacccga cagcgaatgg cgggaggggg cgggctaaaa | 60 |
| gatcgtatta catagtattt ttcccctact ctttgtgttt gtcttttttt tttttttgaa | 120 |
| cgcattcaag ccacttgtct tggtttactt gtttgtttgc ttgcttgctt gcttgcttgc | 180 |
| ctgcttcttg gtcagacggc ccaaaaaagg gaaaaaattc attcatggca cagataagaa | 240 |
| aaagaaaaag tttgtcgacc accgtcatca gaaagcaaga gaagagaaac actcgcgctc | 300 |
| acattctcgc tcgcgtaaga atctta | 326 |

(SEQ ID NO:4)

FIG. 4

M K F A T S V A I L L V A N I A T A L A Q S D G C T P T D Q (SEQ ID NO:37)

FIG. 12

ATGAAGTTCGCGACCTCGGTCGCAATTTTGCTTGTGGCCAA

CATAGCCACCGCCCTCGCG (SEQ ID NO:38)

FIG. 13

```
ctccatcgat cgtgcggtca aaaagaaagg aagaagaaag gaaaaagaaa ggcgtgcgca    60
cccgagtgcg cgctgagcgc ccgctcgcgg ccccgcggag cctccgcgtt agtccccgcc   120
ccgcgccgcg cagtcccccg ggaggcatcg cgcacctctc gccgcccccct cgcgcctcgc  180
cgattccccg cctcccctttt tccgcttctt cgccgcctcc gctcgcggcc gcgtcgcccg  240
cgccccgctc cctatctgct ccccaggggg gcactccgca ccttttgcgc ccgctgccgc   300
cgccgcggcc gccccgccgc cctggtttcc cccgcgagcg cggccgcgtc gccgcgcaaa   360
gactcgccgc gtgccgcccc gagcaacggg tggcggcggc gcggcggcgg gcggggcgcg   420
gcggcgcgta ggcggggcta ggcgccggct aggcgaaacg ccgcccccgg gcgccgccgc   480
cgcccgctcc agagcagtcg ccgcgccaga ccgccaacgc agagaccgag accgaggtac   540
gtcgcgcccg agcacgccgc gacgcgcggc agggacgagg agcacgacgc cgcgccgcgc   600
cgcgcggggg gggggaggga gaggcaggac gcgggagcga gcgtgcatgt tccgcgcga    660
gacgacgccg cgcgcgctgg agaggagata aggcgcttgg atcgcgagag ggccagccag   720
gctggaggcg aaaatgggtg gagaggatag tatcttgcgt gcttggacga ggagactgac   780
gaggaggacg gatacgtcga tgatgatgtg cacagagaag aagcagttcg aaagcgacta   840
ctagcaagca agg                                                     853

(SEQ ID NO:42)
```

FIG. 19

```
ctcttatctg cctcgcgccg ttgaccgccg cttgactctt ggcgcttgcc gctcgcatcc    60
tgcctcgctc gcgcaggcgg gcgggcgagt gggtgggtcc gcagccttcc gcgctcgccc   120
gctagctcgc tcgcgccgtg ctgcagccag cagggcagca ccgcacggca ggcaggtccc   180
ggcgcggatc gatcgatcca tcgatccatc gatccatcga tcgtgcggtc aaaaagaaag   240
gaagaagaaa ggaaaaagaa aggcgtgcgc acccgagtgc gcgctgagcg cccgctcgcg   300
gtcccgcgga gcctccgcgt tagtccccgc cccgcgccgc gcagtccccc gggaggcatc   360
gcgcacctct cgccgccccc tcgcgcctcg ccgattcccc gcctcccctt ttccgcttct   420
tcgccgcctc cgctcgcggc gcgtcgccc gcgcccgct ccctatctgc tccccagggg   480
ggcactccgc accttttgcg cccgctgccg ccgccgcggc cgccccgccg ccctggtttc   540
ccccgcgagc gcggccgcgt cgccgcgcaa agactcgccg cgtgccgccc cgagcaacgg   600
gtggcggcgg cgcggcggcg ggcggggcgc ggcggcgcgt aggcggggct aggcgccggc   660
taggcgaaac gccgccccg ggcgccgccg ccgcccgctc cagagcagtc gccgcgccag   720
accgccaacg cagagaccga gaccgaggta cgtcgcgccc gagcacgccg cgacgcgcgg   780
cagggacgag gagcacgacg ccgcgccgcg ccgcgcgggg gggggaggg agaggcagga   840
cgcgggagcg agcgtgcatg tttccgcgcg agacgacgcc gcgcgcgctg gagaggagat   900
aaggcgcttg gatcgcgaga gggccagcca ggctggaggc gaaaatgggt ggagaggata   960
gtatcttgcg tgcttggacg aggagactga cgaggaggac ggatacgtcg atgatgatgt  1020
gcacagagaa gaagcagttc gaaagcgact actagcaagc aagg                   1064

(SEQ ID NO:43)
```

FIG. 20

```
cttcgctttc tcaacctatc tggacagcaa tccgccactt gccttgatcc ccttccgcgc      60
ctcaatcact cgctccacgt ccctcttccc cctcctcatc tccgtgcttt ctctgccccc     120
cccccccccg ccgcggcgtg cgcgcgcgtg gcgccgcggc cgcgacacct tccatactat     180
cctcgctccc aaaatgggtt gcgctatagg gcccggctag gcgaaagtct agcaggcact     240
tgcttggcgc agagccgccg cggccgctcg ttgccgcgga tggagaggga gagagagccc     300
gcctcgataa gcagagacag acagtgcgac tgacagacag acagagagac tggcagaccg     360
gaatacctcg aggtgagtgc ggcgcgggcg agcgggcggg agcgggagcg caagagggac     420
ggcgcggcgc ggcggccctg cgcgacgccg cggcgtattc tcgtgcgcag cgccgagcag     480
cgggacgggc ggctggctga tggttgaagc ggggcggggt gaaatgttag atgagatgat     540
catcgacgac ggtccgtgcg tcttggctgg cttggctggc ttggctggcg ggcctgccgt     600
gtttgcgaga agaggatga ggagagcgac gaggaaggac gagaagactg acgtgtaggg      660
cgcgcgatgg atgatcgatt gattgattga ttgattggtt gattggctgt gtggtcgatg     720
aacgtgtaga ctcagggagc gtggttaaat tgttcttgcg ccagacgcga ggactccacc     780
cccttctttc gcctttacac agcctttttg tgaagcaaca agaaagaaaa agccaag       837
```

(SEQ ID NO:44)

FIG. 21

```
cttttttccgc tctgcataat cctaaaagaa agactatacc ctagtcactg tacaaatggg      60
acatttctct cccgagcgat agctaaggat ttttgcttcg tgtgcactgt gtgctctggc     120
cgcgcatcga aagtccagga tcttactgtt tctctttcct ttcctttatt tcctgttctc     180
ttcttcgctt tctcaaccta tctggacagc aatccgccac ttgccttgat ccccttccgc     240
gcctcaatca ctcgctccac gtccctcttc cccctcctca tctccgtgct ttctctcgcc     300
cccccccccc ccgccgcggc gtgcgcgcgc gtggcgccgc ggccgcgaca ccttccatac     360
tatcctcgct cccaaaatgg gttgcgctat agggcccggc taggcgaaag tctagcaggc     420
acttgcttgg cgcagagccg ccgcggccgc tcgttgccgc ggatggagag ggagagagag     480
cccgcctcga taagcagaga cagacagtgc gactgacaga cagacagaga gactggcaga     540
ccggaatacc tcgaggtgag tgcggcgcgg gcgagcgggc gggagcggga gcgcaagagg     600
gacggcgcgg cgcggcggcc ctgcgcgacg ccgcggcgta ttctcgtgcg cagcgccgag     660
cagcgggacg ggcggctggc tgatggttga agcggggcgg ggtgaaatgt tagatgagat     720
gatcatcgac gacggtccgt gcgtcttggc tggcttggct ggcttggctg gcgggcctgc     780
cgtgtttgcg agaaagagga tgaggagagc gacgaggaag gacgagaaga ctgacgtgta     840
gggcgcgcga tggatgatcg attgattgat tgattgattg gttgattggc tgtgtggtcg     900
atgaacgtgt agactcaggg agcgtggtta aattgttctt gcgccagacg cgaggactcc     960 accccttct ttcgccttta cacagccttt ttgtgaagca acaagaaaga aaagccaag    1020
```

(SEQ ID NO:45)

FIG. 22

```
CCCGTCCTTGACGCCTTCGCTTCCGGCGCGGCCATCGATTCAATTCACCCATCCGATACGTTCC
GCCCCCTCACGTCCGTCTGCGCACGACCCCTGCACGACCACGCCAAGGCCAACGCGCCGCTCAG
CTCAGCTTGTCGACGAGTCGCACGTCACATATCTCAGATGCATTGCCTGCCTGCCTGCCTGCCT
GCCTGCCTGCCTGCCTGCCTGCCTGCCTCAGCCTCTCTTTGCTCTCTCTGCGGCGGCCGCTGCG
ACGCGCTGTACAGGAGAATGACTCCAGGAAGTGCGGCTGGGATACGCGCTGGCGTCGGCCGTGA
TGCGCGTGACGGGCGGCGGGCACGGCCGGCACGGGTTGAGCAGAGGACGAAGCGAGGCGAGACG
AGACAGGCCAGGCGCGGGGAGCGCTCGCTGCCGTGAGCAGCAGACCAGGGCGCAGGAATGTACT
TTTCTTGCGGGAGCGGAGACGAGGCTGCCGGCTGCTGGCTGCCGGTTGCTCTGCACGCGCCGCC
CGACTTGGCGTAGCGTGGACGCGCGGCGGCGGCCGCCGTCTCGTCGCGGTCGGCTTTGCCGTGT
ATCGACGCTGCGGGCTTGACACGGGATGGCGGAAGTTCAGCATCGCTGCGATCCCTCGCGCCGC
AGAACGAGGAGAGCGCAGGCCGGCTTCAAGTTTGAAAGGAGAGGAAGGCAGGCAAGGAGCTGGA
AGCTTGCCGCGGAAGGCGCAGGCATGCGTCACGTGAAAAAAAGGGATTTCAAGAGTAGTAAGTA
GGTATGGTCTACAAGTCCCCTATTCTTACTTCGCGGAACGTGGGCTGCTCGTGCGGGCGTCCAT
CTTGTTTTGTTTTTTTTCCGCTAGGCGCGTGCATTGCTTGATGAGTCTCAGCGTTCGTCTGC
AGCGAGGGCAGGAAAATAAGCGGCCCGTGCCGTCGAGCGCACAGGACGTGCAAGCGCCTTGCGA
GCGCAGCATCCTTGCACGGCGAGCATAGAGACCGCGGCCGATGGACTCCAGCGAGGAATTTTCG
ACCCTCTCTATCAAGCTGCGCTTGACAGCCGGGAATGGCAGCCTGAGGAGAGAGGGGCGAAGGA
AGGGACTTGGAGAAAAGAGGTAAGGCACCCTCAATCACGGCGCGTGAAAGCCAGTCATCCCTCG
CAAAGAAAAGACAAAAGCGGGTTTTTTGTTTCGATGGGAAAGAATTTCTTAGAGGAAGAAGCGG
CACACAGACTCGCGCCATGCAGATTTCTGCGCAGCTCGCGATCAAACCAGGAACGTGGTCGCTG
CGCGCCACTATCAGGGGTAGCGCACGAATACCAAACGCATTACTAGCTACGCGCCTGTGACCCG
AGGATCGGGCCACAGACGTTGTCTCTTGCCATCCCACGACCTGGCAGCGAGAAGATCGTCCATT
ACTCATCG (SEQ ID NO:46)
```

FIG. 23

| Proposed Structure | Mass [M+Na] | Chage State [z] | 76-3-I1 |
|---|---|---|---|
| $Hex_5HexNAc_2$ | 1579<br>802 | 1<br>2 | √ |
| $Hex_6HexNAc_2$ | 1783<br>903 | 1<br>2 | √ |
| $Hex_7HexNAc_2$ | 1987<br>1005 | 1<br>2 | √ |
| $Hex_8HexNAc_2$ | 1108 | 2 | √ |
| $Hex_9HexNAc_2$ | 1210 | 2 | √ |
| $Hex_{10}HexNAc_2$ | 1312 | 2 | √ |
| $Hex_{11}HexNAc_2$ | 1407 | 2 | √ |
| $Hex_{12}HexNAc_2$ | 1516 | 2 | √ |
| $Hex_{13}HexNAc_2$ | 1618 | 2 | √ |

√……..Detected
n.d…...Not detected

FIG. 40A

*Schizochytrium* predicted signal sequences (based on Signal P program)

alpha-1,6-mannosyltransferase (ALG12):

MRTVRGPQTAALAALLALAATHVAVSPFTKVE   (SEQ ID NO:59)

ATGCGCACGGTGAGGGGGCCGCAAACGGCGGCACTCGCCGCCCTTCTGGCACTTGCCGCGACGC
ACGTGGCTGTGAGCCCGTTCACCAAGGTGGAG   (SEQ ID NO:60)

BiP:

MGRLAKSLVLLTAVLAVIGGVRAEEDKSEA   (SEQ ID NO:61)

ATGGgCCGCCTCGCGAAGTCGCTTGTGCTGCTGACGGCCGTGCTGGCCGTGATCGGAGGCGTCCG
CGCCGAAGAGGACAAGTCCGAGGCC   (SEQ ID NO:62)

alpha-1,3-glucosidase (GLS2):

MTSTARALALVRALVLALAVLALLASQSVAVDRKKFRT   (SEQ ID NO:63)

ATGACGTCAACGGCGCGCGCGCTCGCGCTCGTGCGTGCTTTGGTGCTCGCTCTGGCTGTCTTGGC
GCTGCTAGCGAGCCAAAGCGTGGCCGTGGACCGCAAAAAGTTCAGGACC   (SEQ ID NO:64)

alpha-1,3-1,6-mannosidase - like:

MLRLKPLLLLFLCSLIASPVVAWARGGEGPSTSE   (SEQ ID NO:65)

ATGTTGCGGCTCAAGCCACTTTTACTCCTCTTCCTCTGCTCGTTGATTGCTTCGCCTGTGGTTGCC
TGGGCAAGAGGAGGAGAAGGGCCGTCCACGAGCGAA   (SEQ ID NO:66)

FIG. 41A alpha-1,3-1,6-mannosidase-like #1:

MAKILRSLLLAAVLVVTPQSLRAHSTRDA   (SEQ ID NO:67)

ATGGCCAAGATCTTGCGCAGTTTGCTCCTGGCGGCCGTGCTCGTGGTGACTCCTCAATCACTGCG
TGCTCATTCGACGCGGGACGCA   (SEQ ID NO:68)

alpha-1,2-mannosidase -like:

MVFRRVPWHGAATLAALVVACATCLGLGLDSEEATY   (SEQ ID NO:69)

ATGGTGTTTCGGCGCGTGCCATGGCACGGCGCGGCGACGCTGGCGGCCTTGGTCGTGGCCTGCG
CGACGTGTTTAGGCCTGGGACTGGACTCGGAGGAGGCCACGTAC   (SEQ ID NO:70)

beta-xylosdiase – like proteins:

MTANSVKISIVAVLVAALAWETCAKANYQW   (SEQ ID NO:71)

ATGACAGCTAACTCGGTGAAAATAAGCATCGTGGCTGTGCTGGTCGCGGCACTGGCTTGGGAAA
CATGCGCAAAAGCTAACTATCAGTGG   (SEQ ID NO:72)

carotene synthase:

MARRASRLGAAVVVVLVVVASACCWQAAADVVDAQ   (SEQ ID NO:73)

ATGGCGCGCAGGGCGTCGCGCCTCGGCGCCGCCGTCGTCGTCGTCCTCGTCGTCGTCGCCTCCGC
CTGCTGCTGGCAAGCCGCTGCGGACGTCGTGGACGCGCAG   (SEQ ID NO:74)

FIG. 41B

| AmAcid | Codon | Fraction | AmAcid | Codon | Fraction | AmAcid | Codon | Fraction | AmAcid | Codon | Fraction |
|---|---|---|---|---|---|---|---|---|---|---|---|
| Ala | GCC | 0.64 | End | TAA | 0.34 | Leu | CTT | 0.16 | Ser | TCG | 0.33 |
| Ala | GCA | 0.03 | End | TGA | 0.33 | Leu | TTG | 0.02 | Ser | TCC | 0.31 |
| Ala | GCT | 0.18 | End | TAG | 0.33 | Leu | CTG | 0.12 | Ser | AGT | 0.03 |
| Ala | GCG | 0.16 | Gln | CAA | 0.08 | Leu | CTC | 0.69 | Ser | TCA | 0 |
| Arg | CGG | 0.01 | Gln | CAG | 0.92 | Leu | TTA | 0 | Ser | TCT | 0.09 |
| Arg | AGA | 0 | Glu | GAA | 0.09 | Leu | CTA | 0 | Thr | ACG | 0.3 |
| Arg | CGC | 0.8 | Glu | GAG | 0.91 | Lys | AAA | 0.04 | Thr | ACC | 0.54 |
| Arg | CGA | 0.01 | Gly | GGA | 0.1 | Lys | AAG | 0.96 | Thr | ACA | 0.02 |
| Arg | AGG | 0 | Gly | GGT | 0.2 | Met | ATG | 1 | Thr | ACT | 0.14 |
| Arg | CGT | 0.17 | Gly | GGG | 0 | Phe | TTT | 0.45 | Trp | TGG | 1 |
| Asn | AAC | 0.94 | Gly | GGC | 0.7 | Phe | TTC | 0.55 | Tyr | TAC | 0.94 |
| Asn | AAT | 0.06 | His | CAC | 0.83 | Pro | CCT | 0.21 | Tyr | TAT | 0.06 |
| Asp | GAT | 0.24 | His | CAT | 0.17 | Pro | CCG | 0.34 | Val | GTC | 0.62 |
| Asp | GAC | 0.76 | Ile | ATC | 0.7 | Pro | CCC | 0.43 | Val | GTA | 0 |
| Cys | TGC | 0.95 | Ile | ATA | 0 | Pro | CCA | 0.02 | Val | GTT | 0.14 |
| Cys | TGT | 0.05 | Ile | ATT | 0.3 | Ser | AGC | 0.24 | Val | GTG | 0.24 |

FIG. 42 atgaagttcgcgaccteggtcgcaattttgcttgtggccaacatagccaccgccctcgcgGCCTCCCCCTC
GATGCAGACCCGTGCCTCCGTCGTCATTGATTACAACGTCGCTCCTCCTAACCTCTCCACC
CTCCCGAACGGCAGCCTCTTTGAGACCTGGCGTCCTCGCGCCCACGTTCTTCCCCCTAAC
GGTCAGATTGGCGATCCCTGCCTCCACTACACCGATCCCTCGACTGGCCTCTTTCACGTCG
GCTTTCTCCACGATGGCTCCGGCATTTCCTCCGCCACTACTGACGACCTCGCTACCTACAA
GGATCTCAACCAGGGCAACCAGGTCATCGTCCCCGGCGGTATCAACGACCCTGTCGCTG
TTTTCGACGGCTCCGTCATTCCTTCCGGCATTAACGGCCTCCCTACCCTCCTCTACACCTCC
GTCAGCTACCTCCCCATTCACTGGTCCATCCCCTACACCCGCGGTTCCGAGACGCAGAG
CCTGGCTGTCTCCAGCGATGGTGGCTCCAACTTTACTAAGCTCGACCAGGGCCCCGTTATT
CCTGGCCCCCCCTTTGCCTACAACGTCACCGCCTTCCGCGACCCCTACGTCTTTCAGAAC
CCCACCCTCGACTCCCTCCTCCACTCCAAGAACAACACCTGGTACACCGTCATTTCGGGT
GGCCTCCACGGCAAGGGCCCCGCCCAGTTTCTTTACCGTCAGTACGACCCCGACTTTCA
GTACTGGGAGTTCCTCGGCCAGTGGTGGCACGAGCCTACCAACTCCACCTGGGGCAAC
GGCACCTGGGCCGGCCGCTGGGCCTTCAACTTCGAGACCGGCAACGTCTTTTCGCTTGA
CGAGTACGGCTACAACCCCCACGGCCAGATCTTCTCCACCATTGGCACCGAGGGCTCC
GACCAGCCCGTTGTCCCCCAGCTCACCTCCATCCACGATATGCTTTGGGTCTCCGGTAAC
GTTTCGCGCAACGGATCGGTTTCCTTCACTCCCAACATGGCCGGCTTCCTCGACTGGGGTTT
CTCGTCCTACGCCGCCGCGGGTAAGGTTCTTCCTTCCACGTCGCTCCCCTCCACCAAGTC
CGGTGCCCCCGATCGCTTCATTTCGTACGTTTGGCTCTCCGGCGACCTCTTTGAGCAGGCTG
AGGGCTTTCCTACCAACCAGCAGAACTGGACCGGCACCCTCCTCCTCCCCCGTGAGCTC
CGCGTCCTTTACATCCCCAACGTGGTTGATAACGCCCTTGCGCGCGAGTCCGGCGCTTCCT
GGCAGGTCGTCTCCTCCGATAGCTCGGCCGGTACTGTGGAGCTCCAGACCCTCGGCATTT
CCATCGCCCGCGAGACCAAGGCCGCCCTCCTGTCCGGCACCTCGTTCACTGAGTCCGA
CCGCACTCTTAACTCCTCCGGCGTCGTTCCCTTTAAGCGTTCCCCCTCCGAGAAGTTTTTCGT
CCTCTCCGCCCAGCTCTCCTTCCCCGCCTCCGCCCGCGGCTCGGGCCTCAAGTCCGGC
TTCCAGATTCTTTCCTCCGAGCTCGAGTCCACCACGGTCTACTACCAGTTTAGCAACGAGTC
CATCATCGTCGACCGCAGCAACACCAGCGCCGCCGCCCGTACTACCGACGGTATCGA
CTCCTCCGCCGAGGCCGGCAAGCTCCGCCTCTTTGACGTCCTCAACGGCGGCGAGCAG
GCTATTGAGACCCTCGACCTTACCCTCGTCGTTGATAACTCCGTGCTCGAGATTTACGCCAA
CGGTCGTTTCGCGCTTTCCACCTGGGTTCGCTAA (SEQ ID NO.: 75)

FIG. 44

SEQUENCE LISTING

<160> NUMBER OF SEQ ID NOS: 75

<210> SEQ ID NO 1

```
<211> LENGTH: 35
<212> TYPE: PRT
<213> ORGANISM: Schizochytrium

<400> SEQUENCE: 1

Met Ala Asn Ile Met Ala Asn Val Thr Pro Gln Gly Val Ala Lys Gly
1               5                   10                  15

Phe Gly Leu Phe Val Gly Val Leu Phe Phe Leu Tyr Trp Phe Leu Val
            20                  25                  30

Gly Leu Ala
        35

<210> SEQ ID NO 2
<211> LENGTH: 105
<212> TYPE: DNA
<213> ORGANISM: Schizochytrium

<400> SEQUENCE: 2
atggccaaca tcatggccaa cgtcacgccc cagggcgtcg ccaagggctt tggcctcttt      60
gtcggcgtgc tcttctttct ctactggttc cttgtcggcc tcgcc                    105

<210> SEQ ID NO 3
<211> LENGTH: 1999
<212> TYPE: DNA
<213> ORGANISM: Schizochytrium

<400> SEQUENCE: 3
ccgcgaatca agaaggtagg cgcgctgcga ggcgcggcgg cggagcggag cgagggagag      60
ggagagggag agagagggag ggagacgtcg ccgcggcggg gcctggcctg gcctggtttg     120
gcttggtcag cgcggccttg tccgagcgtg cagctggagt tgggtggatt catttggatt     180
ttcttttgtt tttgttttc tctctttccc ggaaagtgtt ggccggtcgg tgttctttgt     240
tttgatttct tcaaaagttt tggtggttgg ttctctctct tggctctctg tcaggcggtc     300
cggtccacgc cccggcctct cctctcctct cctctcctct cctctccgtg cgtatacgta     360
cgtacgtttg tatacgtaca tacatcccgc ccgccgtgcc ggcgagggtt tgctcagcct     420
ggagcaatgc gatgcgatgc gatgcgatgc gacgcgacgc gacgcgagtc actggttcgc     480
gctgtggctg tggcttgctt gcttacttgc tttcgagctc tcccgctttc ttctttcctt     540
ctcacgccac caccaacgaa agaagatcgg ccccggcacg ccgctgagaa gggctggcgg     600
cgatgacggc acgcgcgccc gctgccacgt tggcgctcgc tgctgctgct gctgctgctg     660
ctgctgctgc tgctgctgct gctgctgctt ctgcgcgcag gctttgccac gaggccggcg     720
tgctggccgc tgccgcttcc agtccgcgtg gagagatcga atgagagata aactggatgg     780
attcatcgag ggatgaatga acgatggttg gatgcctttt tccttttttca ggtccacagc     840 gggaagcagg agcgcgtgaa tctgccgcca tccgcatacg tctgcatcgc atcgcatcgc     900
atgcacgcat cgctcgccgg gagccacaga cgggcgacag gcggccagc cagccaggca     960 gccagccagg caggcaccag agggccagag agcgcgcctc acgcacgcgc cgcagtgcgc    1020
gcatcgctcg cagtgcagac cttgattccc cgcgcggatc tccgcgagcc cgaaacgaag    1080
agcgccgtac gggcccatcc tagcgtcgcc tcgcaccgca tcgcatcgca tcgcgttccc    1140
tagagagtag tactcgacga aggcaccatt tccgcgctcc tcttcggcgc gatcgaggcc    1200 cccgcgccg cgacgatcgc ggcggccgcg cgctggcgg cggccctggc gctcgcgctg    1260
gcggccgccg cgggcgtctg gccctggcgc gcgcgggcgc gcaggagga gcggcagcgg    1320
```

| | | | |
|---|---|---|---|
| ctgctcgccg | ccagagaagg | agcgcgccgg gcccggggag ggacggggag gagaaggaga | 1380 |
| aggcgcgcaa | ggcggccccg | aaagagaaga ccctggactt gaacgcgaag aagaagaaga | 1440 |
| aggagaagaa | gttgaagaag | aagaagaaga aggagaggaa gttgaagaag acgaggagca | 1500 |
| ggcgcgttcc | aaggcgcgtt | ctcttccgga ggcgcgttcc agctgcggcg gcggggcggg | 1560 |
| ctgcggggcg | ggcgcgggcg | cgggtgcggg cagagggac gcgcgcgcgg aggcggaggg | 1620 |
| ggccgagcgg | gagcccctgc | tgctgcgggg cgcccgggcc gcaggtgtgg cgcgcgcgac | 1680 |
| gacggaggcg | acgacgccag | cggccgcgac gacaaggccg gcggcgtcgg cgggcggaag | 1740 |
| gccccgcgcg | gagcagggc | gggagcagga caaggcgcag gagcaggagc agggccggga | 1800 |
| gcgggagcgg | gagcgggcgg | cggagcccga ggcagaaccc aatcgagatc cagagcgagc | 1860 |
| agaggccggc | cgcgagcccg | agcccgcgcc gcagatcact agtaccgctg cggaatcaca | 1920 |
| gcagcagcag | cagcagcagc | agcagcagca gcagcagcag cagccacgag agggagataa | 1980 |
| agaaaaagcg | gcagagacg | | 1999 |

<210> SEQ ID NO 4
<211> LENGTH: 325
<212> TYPE: DNA
<213> ORGANISM: Schizochytrium

<400> SEQUENCE: 4

| | | | |
|---|---|---|---|
| gatccgaaag | tgaaccttgt | cctaacccga cagcgaatgg cgggagggg cgggctaaaa | 60 |
| gatcgtatta | catagtattt | ttcccctact ctttgtgttt gtctttttt tttttttgaac | 120 |
| gcattcaagc | cacttgtctt | ggtttacttg tttgtttgct tgcttgcttg cttgcttgcc | 180 |
| tgcttcttgg | tcagacggcc | caaaaaggg aaaaaattca ttcatggcac agataagaaa | 240 |
| aagaaaaagt | ttgtcgacca | ccgtcatcag aaagcaagag aagagaaaca ctcgcgctca | 300 |
| cattctcgct | cgcgtaagaa | tctta | 325 |

<210> SEQ ID NO 5
<211> LENGTH: 372
<212> TYPE: DNA
<213> ORGANISM: Streptoalloteichus hindustanus

<400> SEQUENCE: 5

| | | | |
|---|---|---|---|
| atggccaagt | tgaccagtgc | cgttccggtg ctcaccgcgc gcgacgtcgc cggagcggtc | 60 |
| gagttctgga | ccgaccggct | cgggttctcc cgggacttcg tggaggacga cttcgccggt | 120 |
| gtggtccggg | acgacgtgac | cctgttcatc agcgcggtcc aggaccaggt ggtgccggac | 180 |
| aacaccctgg | cctgggtgtg | ggtgcgcggc ctggacgagc tgtacgccga gtggtcggag | 240 |
| gtcgtgtcca | cgaacttccg | ggacgcctcc gggccggcca tgaccgagat cggcgagcag | 300 |
| ccgtgggggc | gggagttcgc | cctgcgcgac ccggccggca actgcgtgca cttcgtggcc | 360 |
| gaggagcagg | ac | | 372 |

<210> SEQ ID NO 6
<211> LENGTH: 2055
<212> TYPE: DNA
<213> ORGANISM: Schizochytrium

<400> SEQUENCE: 6

| | | | |
|---|---|---|---|
| atgagcgcga | cccgcgcggc | gacgaggaca gcggcggcgc tgtcctcggc gctgacgacg | 60 |
| cctgtaaagc | agcagcagca | gcagcagctg cgcgtaggcg cggcgtcggc acggctggcg | 120 |
| gccgcggcgt | tctcgtccgg | cacgggcgga gacgcggcca agaaggcggc cgcggcgagg | 180 |

```
gcgttctcca cgggacgcgg ccccaacgcg acacgcgaga agagctcgct ggccacggtc    240
caggcggcga cggacgatgc gcgcttcgtc ggcctgaccg gcgcccaaat ctttcatgag    300
ctcatgcgcg agcaccaggt ggacaccatc tttggctacc ctggcggcgc cattctgccc    360
gtttttgatg ccattttga gagtgacgcc ttcaagttca ttctcgctcg ccacgagcag    420
ggcgccggcc acatggccga gggctacgcg cgcgccacgg gcaagcccgg cgttgtcctc    480
gtcacctcgg gccctggagc caccaacacc atcaccccga tcatggatgc ttacatggac    540
ggtacgccgc tgctcgtgtt caccggccag gtgcccacct ctgctgtcgg cacggacgct    600
ttccaggagt gtgacattgt tggcatcagc gcgcgtgca ccaagtggaa cgtcatggtc    660
aaggacgtga aggagctccc gcgccgcatc aatgaggcct ttgagattgc catgagcggc    720 cgccggtc ccgtgctcgt cgatcttcct aaggatgtga ccgccgttga gctcaaggaa    780
atgcccgaca gctccccca ggttgctgtg cgccagaagc aaaaggtcga gcttttccac    840
aaggagcgca ttggcgctcc tggcacggcc gacttcaagc tcattgccga gatgatcaac    900
cgtgcggagc gacccgtcat ctatgctggc cagggtgtca tgcagagccc gttgaatggc    960
ccggctgtgc tcaaggagtt cgcggagaag gccaacattc ccgtgaccac caccatgcag   1020
ggtctcggcg gctttgacga gcgtagtccc ctctcccctca agatgctcgg catgcacggc   1080
tctgcctacg ccaactactc gatgcagaac gccgatctta tcctggcgct cggtgccccgc   1140 tttgatgatc gtgtgacggg ccgcgttgac gcctttgctc cggaggctcg ccgtgccgag   1200
cgcgagggcc gcggtggcat cgttcacttt gagatttccc ccaagaacct ccacaaggtc   1260
gtccagccca ccgtcgcggt cctcggcgac gtggtcgaga acctcgccaa cgtcacgccc   1320
cacgtgcagc gccaggagcg cgagccgtgg tttgcgcaga tcgccgattg gaaggagaag   1380 caccctttc tgctcgagtc tgttgattcg gacgacaagg ttctcaagcc gcagcaggtc   1440
ctcacggagc ttaacaagca gattctcgag attcaggaga aggacgccga ccaggaggtc   1500
tacatcacca cgggcgtcgg aagccaccag atgcaggcag cgcagttcct tacctggacc   1560
aagccgcgcc agtggatctc ctcgggtggc gccggcacta tgggctacgg ccttccctcg   1620
gccattggcg ccaagattgc caagcccgat gctattgtta ttgacatcga tggtgatgct   1680
tcttattcga tgaccggtat ggaattgatc acagcagccg aattcaaggt tggcgtgaag   1740
attcttcttt tgcagaacaa cttttcaggc atggtcaaga actggcagga tctctttttac   1800 gacaagcgct actcgggcac cgccatgttc aacccgcgct tcgacaaggt cgccgatgcg   1860
atgcgtgcca agggtctcta ctgcgcgaaa cagtcggagc tcaaggacaa gatcaaggag   1920
tttctcgagt acgatgaggg tcccgtcctc ctcgaggttt tcgtggacaa ggacacgctc   1980
gtcttgccca tggtccccgc tggctttccg ctccacgaga tggtcctcga gcctcctaag   2040
cccaaggacg cctaa                                                   2055
```

<210> SEQ ID NO 7
<211> LENGTH: 684
<212> TYPE: PRT
<213> ORGANISM: Schizochytrium

<400> SEQUENCE: 7

Met Ser Ala Thr Arg Ala Ala Thr Arg Thr Ala Ala Ala Leu Ser Ser
1               5                   10                  15

Ala Leu Thr Thr Pro Val Lys Gln Gln Gln Gln Gln Gln Leu Arg Val
            20                  25                  30

-continued

```
Gly Ala Ala Ser Ala Arg Leu Ala Ala Ala Phe Ser Gly Thr
         35                  40                  45

Gly Gly Asp Ala Ala Lys Lys Ala Ala Ala Arg Ala Phe Ser Thr
 50                  55                  60

Gly Arg Gly Pro Asn Ala Thr Arg Glu Lys Ser Ser Leu Ala Thr Val
 65                  70                  75                  80

Gln Ala Ala Thr Asp Asp Ala Arg Phe Val Gly Leu Thr Gly Ala Gln
                 85                  90                  95

Ile Phe His Glu Leu Met Arg Glu His Gln Val Asp Thr Ile Phe Gly
                100                 105                 110

Tyr Pro Gly Gly Ala Ile Leu Pro Val Phe Asp Ala Ile Phe Glu Ser
            115                 120                 125

Asp Ala Phe Lys Phe Ile Leu Ala Arg His Glu Gln Gly Ala Gly His
        130                 135                 140

Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Pro
            180                 185                 190

Thr Ser Ala Val Gly Thr Asp Ala Phe Gln Glu Cys Asp Ile Val Gly
        195                 200                 205

Ile Ser Arg Ala Cys Thr Lys Trp Asn Val Met Val Lys Asp Val Lys
    210                 215                 220

Glu Leu Pro Arg Arg Ile Asn Glu Ala Phe Glu Ile Ala Met Ser Gly
225                 230                 235                 240

Arg Pro Gly Pro Val Leu Val Asp Leu Pro Lys Asp Val Thr Ala Val
                245                 250                 255

Glu Leu Lys Glu Met Pro Asp Ser Ser Pro Gln Val Ala Val Arg Gln
            260                 265                 270

Lys Gln Lys Val Glu Leu Phe His Lys Glu Arg Ile Gly Ala Pro Gly
        275                 280                 285

Thr Ala Asp Phe Lys Leu Ile Ala Glu Met Ile Asn Arg Ala Glu Arg
    290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
                325                 330                 335

Thr Thr Met Gln Gly Leu Gly Gly Phe Asp Glu Arg Ser Pro Leu Ser
            340                 345                 350

Leu Lys Met Leu Gly Met His Gly Ser Ala Tyr Ala Asn Tyr Ser Met
        355                 360                 365

Gln Asn Ala Asp Leu Ile Leu Ala Leu Gly Ala Arg Phe Asp Asp Arg
    370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
                405                 410                 415

Leu His Lys Val Val Gln Pro Thr Val Ala Val Leu Gly Asp Val Val
            420                 425                 430

Glu Asn Leu Ala Asn Val Thr Pro His Val Gln Arg Gln Glu Arg Glu
        435                 440                 445

Pro Trp Phe Ala Gln Ile Ala Asp Trp Lys Glu Lys His Pro Phe Leu
```

```
            450                 455                 460
Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
                485                 490                 495

Asp Gln Glu Val Tyr Ile Thr Thr Gly Val Gly Ser His Gln Met Gln
                500                 505                 510

Ala Ala Gln Phe Leu Thr Trp Thr Lys Pro Arg Gln Trp Ile Ser Ser
                515                 520                 525

Gly Gly Ala Gly Thr Met Gly Tyr Gly Leu Pro Ser Ala Ile Gly Ala
530                 535                 540

Lys Ile Ala Lys Pro Asp Ala Ile Val Ile Asp Ile Asp Gly Asp Ala
545                 550                 555                 560

Ser Tyr Ser Met Thr Gly Met Glu Leu Ile Thr Ala Ala Glu Phe Lys
                565                 570                 575

Val Gly Val Lys Ile Leu Leu Leu Gln Asn Asn Phe Gln Gly Met Val
                580                 585                 590

Lys Asn Trp Gln Asp Leu Phe Tyr Asp Lys Arg Tyr Ser Gly Thr Ala
                595                 600                 605

Met Phe Asn Pro Arg Phe Asp Lys Val Ala Asp Ala Met Arg Ala Lys
610                 615                 620

Gly Leu Tyr Cys Ala Lys Gln Ser Glu Leu Lys Asp Lys Ile Lys Glu
625                 630                 635                 640

Phe Leu Glu Tyr Asp Glu Gly Pro Val Leu Leu Glu Val Phe Val Asp
                645                 650                 655

Lys Asp Thr Leu Val Leu Pro Met Val Pro Ala Gly Phe Pro Leu His
                660                 665                 670

Glu Met Val Leu Glu Pro Pro Lys Pro Lys Asp Ala
                675                 680
```

```
<210> SEQ ID NO 8
<211> LENGTH: 684
<212> TYPE: PRT
<213> ORGANISM: Artificial Sequence
<220> FEATURE:
<223> OTHER INFORMATION: Mutated ALS 1

<400> SEQUENCE: 8

Met Ser Ala Thr Arg Ala Ala Thr Arg Thr Ala Ala Leu Ser Ser
1               5                   10                  15

Ala Leu Thr Thr Pro Val Lys Gln Gln Gln Gln Gln Leu Arg Val
                20                  25                  30

Gly Ala Ala Ser Ala Arg Leu Ala Ala Ala Phe Ser Ser Gly Thr
                35                  40                  45

Gly Gly Asp Ala Ala Lys Lys Ala Ala Ala Arg Ala Phe Ser Thr
50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95

Ile Phe His Glu Leu Met Arg Glu His Gln Val Asp Thr Ile Phe Gly
                100                 105                 110

Tyr Pro Gly Gly Ala Ile Leu Pro Val Phe Asp Ala Ile Phe Glu Ser
                115                 120                 125

Asp Ala Phe Lys Phe Ile Leu Ala Arg His Glu Gln Gly Ala Gly His
```

-continued

```
            130                 135                 140
Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Pro
            180                 185                 190

Thr Ser Ala Val Gly Thr Asp Ala Phe Gln Glu Cys Asp Ile Val Gly
                195                 200                 205

Ile Ser Arg Ala Cys Thr Lys Trp Asn Val Met Val Lys Asp Val Lys
            210                 215                 220

Glu Leu Pro Arg Arg Ile Asn Glu Ala Phe Glu Ile Ala Met Ser Gly
225                 230                 235                 240

Arg Pro Gly Pro Val Leu Val Asp Leu Pro Lys Asp Val Thr Ala Val
                245                 250                 255

Glu Leu Lys Glu Met Pro Asp Ser Ser Pro Gln Val Ala Val Arg Gln
            260                 265                 270

Lys Gln Lys Val Glu Leu Phe His Lys Glu Arg Ile Gly Ala Pro Gly
            275                 280                 285

Thr Ala Asp Phe Lys Leu Ile Ala Glu Met Ile Asn Arg Ala Glu Arg
            290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
                325                 330                 335

Thr Thr Met Gln Gly Leu Gly Gly Phe Asp Glu Arg Ser Pro Leu Ser
            340                 345                 350

Leu Lys Met Leu Gly Met His Gly Ser Ala Tyr Ala Asn Tyr Ser Met
            355                 360                 365

Gln Asn Ala Asp Leu Ile Leu Ala Leu Gly Ala Arg Phe Asp Asp Arg
            370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
                405                 410                 415

Leu His Lys Val Val Gln Pro Thr Val Ala Val Leu Gly Asp Val Val
            420                 425                 430

Glu Asn Leu Ala Asn Val Thr Pro His Val Gln Arg Gln Glu Arg Glu
            435                 440                 445

Pro Trp Phe Ala Gln Ile Ala Asp Trp Lys Glu Lys His Pro Phe Leu
450                 455                 460

Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
                485                 490                 495

Asp Gln Glu Val Tyr Ile Thr Thr Gly Val Gly Ser His Gln Met Gln
            500                 505                 510

Ala Ala Gln Phe Leu Thr Trp Thr Lys Pro Arg Gln Trp Ile Ser Ser
            515                 520                 525

Gly Gly Ala Gly Thr Met Gly Tyr Gly Leu Pro Ser Ala Ile Gly Ala
            530                 535                 540

Lys Ile Ala Lys Pro Asp Ala Ile Val Ile Asp Ile Asp Gly Asp Ala
545                 550                 555                 560
```

```
Ser Tyr Ser Met Thr Gly Met Glu Leu Ile Thr Ala Ala Glu Phe Lys
                565                 570                 575

Val Gly Val Lys Ile Leu Leu Leu Gln Asn Asn Phe Gln Gly Met Val
            580                 585                 590

Lys Asn Val Gln Asp Leu Phe Tyr Asp Lys Arg Tyr Ser Gly Thr Ala
        595                 600                 605

Met Phe Asn Pro Arg Phe Asp Lys Val Ala Asp Ala Met Arg Ala Lys
    610                 615                 620

Gly Leu Tyr Cys Ala Lys Gln Ser Glu Leu Lys Asp Lys Ile Lys Glu
625                 630                 635                 640

Phe Leu Glu Tyr Asp Glu Gly Pro Val Leu Leu Glu Val Phe Val Asp
                645                 650                 655

Lys Asp Thr Leu Val Leu Pro Met Val Pro Ala Gly Phe Pro Leu His
            660                 665                 670

Glu Met Val Leu Glu Pro Pro Lys Pro Lys Asp Ala
        675                 680
```

<210> SEQ ID NO 9
<211> LENGTH: 684
<212> TYPE: PRT
<213> ORGANISM: Artificial Sequence
<220> FEATURE:
<223> OTHER INFORMATION: Mutated ALS 2

<400> SEQUENCE: 9

```
Met Ser Ala Thr Arg Ala Ala Thr Arg Thr Ala Ala Ala Leu Ser Ser
1               5                   10                  15

Ala Leu Thr Thr Pro Val Lys Gln Gln Gln Gln Gln Gln Leu Arg Val
            20                  25                  30

Gly Ala Ala Ser Ala Arg Leu Ala Ala Ala Phe Ser Ser Gly Thr
        35                  40                  45

Gly Gly Asp Ala Ala Lys Lys Ala Ala Ala Arg Ala Phe Ser Thr
    50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95

Ile Phe His Glu Leu Met Arg Glu His Gln Val Asp Thr Ile Phe Gly
            100                 105                 110

Tyr Pro Gly Gly Ala Ile Leu Pro Val Phe Asp Ala Ile Phe Glu Ser
        115                 120                 125

Asp Ala Phe Lys Phe Ile Leu Ala Arg His Glu Gln Gly Ala Gly His
    130                 135                 140

Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Gln
            180                 185                 190

Thr Ser Ala Val Gly Thr Asp Ala Phe Gln Glu Cys Asp Ile Val Gly
        195                 200                 205

Ile Ser Arg Ala Cys Thr Lys Trp Asn Val Met Val Lys Asp Val Lys
    210                 215                 220

Glu Leu Pro Arg Arg Ile Asn Glu Ala Phe Glu Ile Ala Met Ser Gly
225                 230                 235                 240
```

```
Arg Pro Gly Pro Val Leu Val Asp Leu Pro Lys Asp Val Thr Ala Val
            245                 250                 255

Glu Leu Lys Glu Met Pro Asp Ser Ser Pro Gln Val Ala Val Arg Gln
            260                 265                 270

Lys Gln Lys Val Glu Leu Phe His Lys Glu Arg Ile Gly Ala Pro Gly
            275                 280                 285

Thr Ala Asp Phe Lys Leu Ile Ala Glu Met Ile Asn Arg Ala Glu Arg
            290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
            325                 330                 335

Thr Thr Met Gln Gly Leu Gly Gly Phe Asp Glu Arg Ser Pro Leu Ser
            340                 345                 350

Leu Lys Met Leu Gly Met His Gly Ser Ala Tyr Ala Asn Tyr Ser Met
            355                 360                 365

Gln Asn Ala Asp Leu Ile Leu Ala Leu Gly Ala Arg Phe Asp Asp Arg
            370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
            405                 410                 415

Leu His Lys Val Val Gln Pro Thr Val Ala Val Leu Gly Asp Val Val
            420                 425                 430

Glu Asn Leu Ala Asn Val Thr Pro His Val Gln Arg Gln Glu Arg Glu
            435                 440                 445

Pro Trp Phe Ala Gln Ile Ala Asp Trp Lys Glu Lys His Pro Phe Leu
            450                 455                 460

Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
            485                 490                 495

Asp Gln Glu Val Tyr Ile Thr Thr Gly Val Gly Ser His Gln Met Gln
            500                 505                 510

Ala Ala Gln Phe Leu Thr Trp Thr Lys Pro Arg Gln Trp Ile Ser Ser
            515                 520                 525

Gly Gly Ala Gly Thr Met Gly Tyr Gly Leu Pro Ser Ala Ile Gly Ala
            530                 535                 540

Lys Ile Ala Lys Pro Asp Ala Ile Val Ile Asp Ile Asp Gly Asp Ala
545                 550                 555                 560

Ser Tyr Ser Met Thr Gly Met Glu Leu Ile Thr Ala Ala Glu Phe Lys
            565                 570                 575

Val Gly Val Lys Ile Leu Leu Leu Gln Asn Asn Phe Gln Gly Met Val
            580                 585                 590

Lys Asn Trp Gln Asp Leu Phe Tyr Asp Lys Arg Tyr Ser Gly Thr Ala
            595                 600                 605

Met Phe Asn Pro Arg Phe Asp Lys Val Ala Asp Ala Met Arg Ala Lys
            610                 615                 620

Gly Leu Tyr Cys Ala Lys Gln Ser Glu Leu Lys Asp Lys Ile Lys Glu
625                 630                 635                 640

Phe Leu Glu Tyr Asp Glu Gly Pro Val Leu Leu Glu Val Phe Val Asp
            645                 650                 655
```

Lys Asp Thr Leu Val Leu Pro Met Val Pro Ala Gly Phe Pro Leu His
            660                 665                 670

Glu Met Val Leu Glu Pro Pro Lys Pro Lys Asp Ala
            675                 680

<210> SEQ ID NO 10
<211> LENGTH: 684
<212> TYPE: PRT
<213> ORGANISM: Artificial Sequence
<220> FEATURE:
<223> OTHER INFORMATION: Mutated ALS 3

<400> SEQUENCE: 10

Met Ser Ala Thr Arg Ala Ala Thr Arg Thr Ala Ala Leu Ser Ser
1               5                   10                  15

Ala Leu Thr Thr Pro Val Lys Gln Gln Gln Gln Gln Leu Arg Val
            20                  25                  30

Gly Ala Ala Ser Ala Arg Leu Ala Ala Ala Phe Ser Ser Gly Thr
            35                  40                  45

Gly Gly Asp Ala Ala Lys Lys Ala Ala Ala Arg Ala Phe Ser Thr
        50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95

Ile Phe His Glu Leu Met Arg Glu His Gln Val Asp Thr Ile Phe Gly
            100                 105                 110

Tyr Pro Gly Gly Ala Ile Leu Pro Val Phe Asp Ala Ile Phe Glu Ser
            115                 120                 125

Asp Ala Phe Lys Phe Ile Leu Ala Arg His Glu Gln Gly Ala Gly His
        130                 135                 140

Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Gln
            180                 185                 190

Thr Ser Ala Val Gly Thr Asp Ala Phe Gln Glu Cys Asp Ile Val Gly
            195                 200                 205

Ile Ser Arg Ala Cys Thr Lys Trp Asn Val Met Val Lys Asp Val Lys
        210                 215                 220

Glu Leu Pro Arg Arg Ile Asn Glu Ala Phe Glu Ile Ala Met Ser Gly
225                 230                 235                 240

Arg Pro Gly Pro Val Leu Val Asp Leu Pro Lys Asp Val Thr Ala Val
                245                 250                 255

Glu Leu Lys Glu Met Pro Asp Ser Ser Pro Gln Val Ala Val Arg Gln
            260                 265                 270

Lys Gln Lys Val Glu Leu Phe His Lys Glu Arg Ile Gly Ala Pro Gly
            275                 280                 285

Thr Ala Asp Phe Lys Leu Ile Ala Glu Met Ile Asn Arg Ala Glu Arg
        290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
                325                 330                 335

```
Thr Thr Met Gln Gly Leu Gly Gly Phe Asp Glu Arg Ser Pro Leu Ser
            340                 345                 350

Leu Lys Met Leu Gly Met His Gly Ser Ala Tyr Ala Asn Tyr Ser Met
        355                 360                 365

Gln Asn Ala Asp Leu Ile Leu Ala Leu Gly Ala Arg Phe Asp Asp Arg
    370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
                405                 410                 415

Leu His Lys Val Val Gln Pro Thr Val Ala Val Leu Gly Asp Val Val
                420                 425                 430

Glu Asn Leu Ala Asn Val Thr Pro His Val Gln Arg Gln Glu Arg Glu
            435                 440                 445

Pro Trp Phe Ala Gln Ile Ala Asp Trp Lys Glu Lys His Pro Phe Leu
        450                 455                 460

Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
                485                 490                 495

Asp Gln Glu Val Tyr Ile Thr Thr Gly Val Gly Ser His Gln Met Gln
                500                 505                 510

Ala Ala Gln Phe Leu Thr Trp Thr Lys Pro Arg Gln Trp Ile Ser Ser
            515                 520                 525

Gly Gly Ala Gly Thr Met Gly Tyr Gly Leu Pro Ser Ala Ile Gly Ala
        530                 535                 540

Lys Ile Ala Lys Pro Asp Ala Ile Val Ile Asp Ile Asp Gly Asp Ala
545                 550                 555                 560

Ser Tyr Ser Met Thr Gly Met Glu Leu Ile Thr Ala Ala Glu Phe Lys
                565                 570                 575

Val Gly Val Lys Ile Leu Leu Leu Gln Asn Asn Phe Gln Gly Met Val
                580                 585                 590

Lys Asn Val Gln Asp Leu Phe Tyr Asp Lys Arg Tyr Ser Gly Thr Ala
            595                 600                 605

Met Phe Asn Pro Arg Phe Asp Lys Val Ala Asp Ala Met Arg Ala Lys
        610                 615                 620

Gly Leu Tyr Cys Ala Lys Gln Ser Glu Leu Lys Asp Lys Ile Lys Glu
625                 630                 635                 640

Phe Leu Glu Tyr Asp Glu Gly Pro Val Leu Leu Glu Val Phe Val Asp
                645                 650                 655

Lys Asp Thr Leu Val Leu Pro Met Val Pro Ala Gly Phe Pro Leu His
                660                 665                 670

Glu Met Val Leu Glu Pro Pro Lys Pro Lys Asp Ala
            675                 680

<210> SEQ ID NO 11
<211> LENGTH: 2052
<212> TYPE: DNA
<213> ORGANISM: Artificial Sequence
<220> FEATURE:
<223> OTHER INFORMATION: Mutated ALS 1

<400> SEQUENCE: 11
atgagcgcga cccgcgcggc gacgaggaca gcggcggcgc tgtcctcggc gctgacgacg      60
cctgtaaagc agcagcagca gcagcagctg cgcgtaggcg cggcgtcggc acggctggcg     120
```

```
gccgcggcgt tctcgtccgg cacgggcgga gacgcggcca agaaggcggc cgcggcgagg      180
gcgttctcca cgggacgcgg ccccaacgcg acacgcgaga agagctcgct ggccacggtc      240
caggcggcga cggacgatgc gcgcttcgtc ggcctgaccg gcgcccaaat ctttcatgag      300
ctcatgcgcg agcaccaggt ggacaccatc tttggctacc ctggcggcgc cattctgccc      360 gttttttgatg ccattttga gagtgacgcc ttcaagttca ttctcgctcg ccacgagcag      420
ggcgccggcc acatggccga gggctacgcg cgcgccacgg gcaagcccgg cgttgtcctc      480
gtcacctcgg gcctggagc caccaacacc atcaccccga tcatggatgc ttacatggac      540
ggtacgccgc tgctcgtgtt caccggccag gtgcccacct tgctgtcgg cacggacgct      600 ttccaggagt gtgacattgt tggcatcagc cgcgcgtgca ccaagtggaa cgtcatggtc      660
aaggacgtga aggagctccc gccgcatc aatgaggcct ttgagattgc catgagcggc       720
cgcccgggtc ccgtgctcgt cgatcttcct aaggatgtga ccgccgttga gctcaaggaa      780
atgcccgaca gctcccccca ggttgctgtg cgccagaagc aaaaggtcga gcttttccac      840
aaggagcgca ttggcgctcc tggcacggcc gacttcaagc tcattgccga gatgatcaac      900
cgtgcggagc gacccgtcat ctatgctggc cagggtgtca tgcagagccc gttgaatggc      960
ccggctgtgc tcaaggagtt cgcggagaag gccaacattc ccgtgaccac caccatgcag     1020
ggtctcggcg gctttgacga gcgtagtccc ctctccctca agatgctcgg catgcacggc     1080
tctgcctacg ccaactactc gatgcagaac gccgatctta tcctggcgct cggtgcccgc     1140
tttgatgatc gtgtgacggg ccgcgttgac gcctttgctc cggaggctcg ccgtgccgag     1200
cgcgagggcc gcggtggcat cgttcacttt gagatttccc ccaagaacct ccacaaggtc     1260
gtccagccca ccgtcgcggt cctcggcgac gtggtcgaga acctcgccaa cgtcacgccc     1320
cacgtgcagc gccaggagcg cgagccgtgg tttgcgcaga tcgccgattg gaaggagaag     1380 caccctttt ctgctcgagtc tgttgattcg gacgacaagg ttctcaagcc gcagcaggtc     1440
ctcacggagc ttaacaagca gattctcgag attcaggaga aggacgccga ccaggaggtc     1500
tacatcacca cggcgtcgg aagccaccag atgcaggcag cgcagttcct tacctggacc     1560
aagccgcgcc agtggatctc ctcgggtggc gccggcacta gggctacgg ccttccctcg     1620 gccattggcg ccaagattgc caagcccgat gctattgtta ttgacatcga tggtgatgct     1680
tcttattcga tgaccggtat ggaattgatc acagcagccg aattcaaggt tggcgtgaag     1740
attcttcttt tgcagaacaa cttcaggc atggtcaaga acgttcagga tctctttac      1800 gacaagcgct actcgggcac cgccatgttc aacccgcgct cgacaaggt cgccgatgcg      1860 atgcgtgcca agggtctcta ctgcgcgaaa cagtcggagc tcaaggacaa gatcaaggag     1920
tttctcgagt acgatgaggg tcccgtcctc ctcgaggttt tcgtggacaa ggacacgctc     1980
gtcttgccca tggtccccgc tggctttccg ctccacgaga tggtcctcga gcctcctaag     2040
cccaaggacg cc                                                         2052
```

<210> SEQ ID NO 12
<211> LENGTH: 2052
<212> TYPE: DNA
<213> ORGANISM: Artificial Sequence
<220> FEATURE:
<223> OTHER INFORMATION: Mutated ALS 2

<400> SEQUENCE: 12

```
atgagcgcga cccgcgcggc gacgaggaca gcggcggcgc tgtcctcggc gctgacgacg       60
```

```
cctgtaaagc agcagcagca gcagcagctg cgcgtaggcg cggcgtcggc acggctggcg    120
gccgcggcgt tctcgtccgg cacgggcgga gacgcggcca agaaggcggc cgcggcgagg    180
gcgttctcca cgggacgcgg ccccaacgcg acacgcgaga agagctcgct ggccacggtc    240
caggcggcga cggacgatgc gcgcttcgtc ggcctgaccg gcgcccaaat ctttcatgag    300
ctcatgcgcg agcaccaggt ggacaccatc tttggctacc ctggcggcgc cattctgccc    360
gttttttgatg ccatttttga gagtgacgcc ttcaagttca ttctcgctcg ccacgagcag    420
ggcgccggcc acatggccga gggctacgcg cgcgccacgg gcaagcccgg cgttgtcctc    480
gtcacctcgg gccctggagc caccaacacc atcaccccga tcatggatgc ttacatggac    540
ggtacgccgc tgctcgtgtt caccggccag gtgcagacct ctgctgtcgg cacggacgct    600
ttccaggagt gtgacattgt tggcatcagc cgcgcgtgca ccaagtggaa cgtcatggtc    660
aaggacgtga aggagctccc cgcgccgcatc aatgaggcct ttgagattgc catgagcggc    720
cgcccgggtc ccgtgctcgt cgatcttcct aaggatgtga ccgccgttga gctcaaggaa    780
atgcccgaca gctccccca ggttgctgtg cgccagaagc aaaaggtcga gcttttccac    840
aaggagcgca ttggcgctcc tggcacggcc gacttcaagc tcattgccga gatgatcaac    900
cgtgcggagc gacccgtcat ctatgctggc cagggtgtca tgcagagccc gttgaatggc    960
ccggctgtgc tcaaggagtt cgcggagaag gccaacattc ccgtgaccac caccatgcag    1020
ggtctcggcg gctttgacga gcgtagtccc ctctccctca gatgctcgg catgcacggc    1080
tctgcctacg ccaactactc gatgcagaac gccgatctta tcctggcgct cggtgcccgc    1140
tttgatgatc gtgtgacggg ccgcgttgac gcctttgctc cggaggctcg ccgtgccgag    1200
cgcgagggcc gcggtggcat cgttcacttt gagatttccc ccaagaacct ccacaaggtc    1260
gtccagccca ccgtcgcggt cctcggcgac gtggtcgaga acctcgccaa cgtcacgccc    1320
cacgtgcagc gccaggagcg cgagccgtgg tttgcgcaga tcgccgattg aaggagaag    1380
cacccttttc tgctcgagtc tgttgattcg gacgacaagg ttctcaagcc gcagcaggtc    1440
ctcacggagc ttaacaagca gattctcgag attcaggaga aggacgccga ccaggaggtc    1500
tacatcacca cggcgtcgg aagccaccag atgcaggcag cgcagttcct tacctggacc    1560
aagccgcgcc agtggatctc ctcgggtggc gccggcacta tgggctacgg ccttccctcg    1620
gccattggcg ccaagattgc caagcccgat gctattgtta ttgacatcga tggtgatgct    1680
tcttattcga tgaccggtat ggaattgatc acagcagccg aattcaaggt tggcgtgaag    1740
attcttcttt tgcagaacaa cttttcaggggc atggtcaaga actggcagga tctcttttac    1800
gacaagcgct actcgggcac cgccatgttc aacccgcgct tcgacaaggt cgccgatgcg    1860
atgcgtgcca aggtctctca ctgcgcgaaa cagtcggagc tcaaggacaa gatcaaggag    1920
tttctcgagt acgatgaggg tcccgtcctc ctcgaggttt tcgtggacaa ggacacgctc    1980
gtcttgccca tggtccccgc tggctttccg ctccacgaga tggtcctcga gcctcctaag    2040
cccaaggacg cc                                                         2052
```

<210> SEQ ID NO 13
<211> LENGTH: 2055
<212> TYPE: DNA
<213> ORGANISM: Artificial Sequence
<220> FEATURE:
<223> OTHER INFORMATION: Mutated ALS 3

<400> SEQUENCE: 13

```
atgagcgcga cccgcgcggc gacgaggaca gcggcggcgc tgtcctcggc gctgacgacg    60
```

```
cctgtaaagc agcagcagca gcagcagctg cgcgtaggcg cggcgtcggc acggctggcg    120
gccgcggcgt tctcgtccgg cacgggcgga gacgcgccca agaaggcggc cgcggcgagg    180
gcgttctcca cgggacgcgg ccccaacgcg acacgcgaga agagctcgct ggccacggtc    240
caggcggcga cggacgatgc gcgcttcgtc ggcctgaccg gcgcccaaat ctttcatgag    300
ctcatgcgcg agcaccaggt ggacaccatc tttggctacc ctggcggcgc cattctgccc    360 gttttttgatg ccattttga gagtgacgcc ttcaagttca ttctcgctcg ccacgagcag    420
ggcgccggcc acatggccga gggctacgcg cgcgccacgg gcaagcccgg cgttgtcctc    480
gtcacctcgg gccctggagc caccaacacc atcaccccga tcatggatgc ttacatggac    540
ggtacgccgc tgctcgtgtt caccggccag gtgcagacct ctgctgtcgg cacggacgct    600
ttccaggagt gtgacattgt tggcatcagc gcgcgtgca ccaagtggaa cgtcatggtc    660
aaggacgtga aggagctccc gcgccgcatc aatgaggcct ttgagattgc catgagcggc    720
cgcccgggtc ccgtgctcgt cgatcttcct aaggatgtga ccgccgttga gctcaaggaa    780
atgcccgaca gctcccccca ggttgctgtg cgccagaagc aaaaggtcga gcttttccac    840
aaggagcgca ttggcgctcc tggcacggcc gacttcaagc tcattgccga gatgatcaac    900
cgtgcggagc gacccgtcat ctatgctggc cagggtgtca tgcagagccc gttgaatggc    960
ccggctgtgc tcaaggagtt cgcggagaag gccaacattc ccgtgaccac caccatgcag   1020
ggtctcggcg gctttgacga gcgtagtccc ctctccctca agatgctcgg catgcacggc   1080
tctgcctacg ccaactactc gatgcagaac gccgatctta tcctggcgct cggtgcccgc   1140
tttgatgatc gtgtgacggg ccgcgttgac gcctttgctc cggaggctcg ccgtgccgag   1200
cgcgagggcc gcggtggcat cgttcacttt gagatttccc ccaagaacct ccacaaggtc   1260
gtccagccca ccgtcgcggt cctcggcgac gtggtcgaga acctcgccaa cgtcacgccc   1320
cacgtgcagc gccaggagcg cgagccgtgg tttgcgcaga tcgccgattg gaaggagaag   1380 caccctttc tgctcgagtc tgttgattcg gacgacaagg ttctcaagcc gcagcaggtc   1440
ctcacggagc ttaacaagca gattctcgag attcaggaga aggacgccga ccaggaggtc   1500
tacatcacca cgggcgtcgg aagccaccag atgcaggcag cgcagttcct tacctggacc   1560
aagccgcgcc agtggatctc ctcgggtggc gccggcacta tgggctacgg ccttccctcg   1620
gccattggcg ccaagattgc caagcccgat gctattgtta ttgacatcga tggtgatgct   1680
tcttattcga tgaccggtat ggaattgatc acagcagccg aattcaaggt tggcgtgaag   1740
attcttcttt tgcagaacaa cttcagggc atggtcaaga acgttcagga tctcttttac   1800
gacaagcgct actcgggcac cgccatgttc aacccgcgct tcgacaaggt cgccgatgcg   1860
atgcgtgcca agggtctcta ctgcgcgaaa cagtcggagc tcaaggacaa gatcaaggag   1920
tttctcgagt acgatgaggg tcccgtcctc ctcgaggttt tcgtggacaa ggacacgctc   1980
gtcttgccca tggtccccgc tggctttccg ctccacgaga tggtcctcga gcctcctaag   2040
cccaaggacg cctaa                                                    2055
```

<210> SEQ ID NO 14
<211> LENGTH: 12
<212> TYPE: DNA
<213> ORGANISM: Schizochytrium

<400> SEQUENCE: 14

```
cacgacgagt tg                                                         12
```

<210> SEQ ID NO 15
<211> LENGTH: 53
<212> TYPE: PRT
<213> ORGANISM: Schizochytrium

<400> SEQUENCE: 15

Met Ala Asn Ile Met Ala Asn Val Thr Pro Gln Gly Val Ala Lys Gly
1               5                   10                  15

Phe Gly Leu Phe Val Gly Val Leu Phe Phe Leu Tyr Trp Phe Leu Val
            20                  25                  30

Gly Leu Ala Leu Leu Gly Asp Gly Phe Lys Val Ile Ala Gly Asp Ser
        35                  40                  45

Ala Gly Thr Leu Phe
    50

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer S4termF

<400> SEQUENCE: 16
gatcccatgg cacgtgctac g                                          21

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer S4termR

<400> SEQUENCE: 17
ggcaacatgt atgataagat ac                                         22

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer C2mcsSmaF

<400> SEQUENCE: 18
gatccccggg ttaagcttgg t                                          21

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer C2mcsSmaR

<400> SEQUENCE: 19
actggggccc gtttaaactc                                            20

<210> SEQ ID NO 20
<211> LENGTH: 34
<212> TYPE: DNA
<213> ORGANISM: Artificial Sequence
<220> FEATURE:
<223> OTHER INFORMATION: Synthetic Primer 5'tubMCS_BglI

<400> SEQUENCE: 20
gactagatct caattttagg ccccccactg accg                            34

<210> SEQ ID NO 21
<211> LENGTH: 34
<212> TYPE: DNA
<213> ORGANISM: Artificial Sequence
<220> FEATURE:
<223> OTHER INFORMATION: Synthetic Primer 3'SV40MCS_Sal

<400> SEQUENCE: 21
gactgtcgac catgtatgat aagatacatt gatg                            34

<210> SEQ ID NO 22
<211> LENGTH: 28
<212> TYPE: DNA
<213> ORGANISM: Artificial Sequence
<220> FEATURE:
<223> OTHER INFORMATION: Synthetic Primer 5'ALSproNde3

<400> SEQUENCE: 22
gactcatatg gcccaggcct actttcac                                   28

<210> SEQ ID NO 23
<211> LENGTH: 34
<212> TYPE: DNA
<213> ORGANISM: Artificial Sequence
<220> FEATURE:
<223> OTHER INFORMATION: Synthetic Primer 3'ALStermBglII

<400> SEQUENCE: 23
gactagatct gggtcaaggc agaagaattc cgcc                            34

<210> SEQ ID NO 24
<211> LENGTH: 97
<212> TYPE: DNA
<213> ORGANISM: Artificial Sequence
<220> FEATURE:
<223> OTHER INFORMATION: Synthetic Primer sec.Gfp5'1b

<400> SEQUENCE: 24
tactggttcc ttgtcggcct cgcccttctc ggcgatggct tcaaggtcat cgccggtgac   60
tccgccggta cgctcttcat ggtgagcaag ggcgagg                           97

<210> SEQ ID NO 25
<211> LENGTH: 32
<212> TYPE: DNA
<213> ORGANISM: Artificial Sequence
<220> FEATURE:
<223> OTHER INFORMATION: Synthetic Primer sec.Gfp3'Spe

<400> SEQUENCE: 25
gatcggtacc ggtgttcttt gttttgattt ct                              32

<210> SEQ ID NO 26
<211> LENGTH: 105
<212> TYPE: DNA
<213> ORGANISM: Artificial Sequence
<220> FEATURE:
<223> OTHER INFORMATION: Synthetic Primer sec.Gfp5'Bam

<400> SEQUENCE: 26
taatggatcc atggccaaca tcatggccaa cgtcacgccc cagggcgtcg ccaagggctt   60
tggcctcttt gtcggcgtgc tcttctttct ctactggttc cttgt                 105

<210> SEQ ID NO 27

```
<211> LENGTH: 40
<212> TYPE: DNA
<213> ORGANISM: Artificial Sequence
<220> FEATURE:
<223> OTHER INFORMATION: Synthetic Primer ss.eGfpHELD3'RV

<400> SEQUENCE: 27
cctgatatct tacaactcgt cgtggttgta cagctcgtcc                            40

<210> SEQ ID NO 28
<211> LENGTH: 105
<212> TYPE: DNA
<213> ORGANISM: Artificial Sequence
<220> FEATURE:
<223> OTHER INFORMATION: Synthetic Primer sec.Gfp5'Bam2

<400> SEQUENCE: 28
taatggatcc atggccaaca tcatggccaa cgtcacgccc cagggcgtcg ccaagggctt      60
tggcctcttt gtcggcgtgc tcttctttct ctactggttc cttgt                    105

<210> SEQ ID NO 29
<211> LENGTH: 27
<212> TYPE: DNA
<213> ORGANISM: Artificial Sequence
<220> FEATURE:
<223> OTHER INFORMATION: Synthetic Primer prREZ15

<400> SEQUENCE: 29
cggtacccgc gaatcaagaa ggtaggc                                         27

<210> SEQ ID NO 30
<211> LENGTH: 27
<212> TYPE: DNA
<213> ORGANISM: Artificial Sequence
<220> FEATURE:
<223> OTHER INFORMATION: Synthetic Primer prREZ16

<400> SEQUENCE: 30
cggatcccgt ctctgccgct ttttctt                                         27

<210> SEQ ID NO 31
<211> LENGTH: 30
<212> TYPE: DNA
<213> ORGANISM: Artificial Sequence
<220> FEATURE:
<223> OTHER INFORMATION: Synthetic Primer prREZ17

<400> SEQUENCE: 31
cggatccgaa agtgaacctt gtcctaaccc                                      30

<210> SEQ ID NO 32
<211> LENGTH: 27
<212> TYPE: DNA
<213> ORGANISM: Artificial Sequence
<220> FEATURE:
<223> OTHER INFORMATION: Synthetic Primer prREZ18

<400> SEQUENCE: 32
ctctagacag atccgcacca tcggccg                                         27

<210> SEQ ID NO 33
<211> LENGTH: 32
<212> TYPE: DNA
<213> ORGANISM: Artificial Sequence
<220> FEATURE:
<223> OTHER INFORMATION: Synthetic Primer 5'eGFP_kpn
```

```
<400> SEQUENCE: 33
gactggtacc atggtgaagc aagggcgagg ag                                    32

<210> SEQ ID NO 34
<211> LENGTH: 34
<212> TYPE: DNA
<213> ORGANISM: Artificial Sequence
<220> FEATURE:
<223> OTHER INFORMATION: Synthetic Primer 3'eGFP_xba

<400> SEQUENCE: 34
gacttctaga ttacttgtac agctcgtcca tgcc                                  34

<210> SEQ ID NO 35
<211> LENGTH: 32
<212> TYPE: DNA
<213> ORGANISM: Artificial Sequence
<220> FEATURE:
<223> OTHER INFORMATION: Synthetic Primer 5'ORFCproKpn-2

<400> SEQUENCE: 35
gatcggtacc ggtgttcttt gttttgattt ct                                    32

<210> SEQ ID NO 36
<211> LENGTH: 31
<212> TYPE: DNA
<213> ORGANISM: Artificial Sequence
<220> FEATURE:
<223> OTHER INFORMATION: Synthetic Primer 3'ORFCproKpn-2

<400> SEQUENCE: 36
gatcggtacc gtctctgccg cttttctttt a                                     31

<210> SEQ ID NO 37
<211> LENGTH: 20
<212> TYPE: PRT
<213> ORGANISM: Schizochytrium

<400> SEQUENCE: 37

Met Lys Phe Ala Thr Ser Val Ala Ile Leu Leu Val Ala Asn Ile Ala
1               5                   10                  15

Thr Ala Leu Ala
            20

<210> SEQ ID NO 38
<211> LENGTH: 60
<212> TYPE: DNA
<213> ORGANISM: Schizochytrium

<400> SEQUENCE: 38
atgaagttcg cgacctcggt cgcaattttg cttgtggcca acatagccac cgccctcgcg     60

<210> SEQ ID NO 39
<211> LENGTH: 28
<212> TYPE: DNA
<213> ORGANISM: Artificial Sequence
<220> FEATURE:
<223> OTHER INFORMATION: Synthetic Primer 5'ss-X Bgl long

<400> SEQUENCE: 39
gactagatct atgaagttcg cgacctcg                                         28

<210> SEQ ID NO 40
```

```
<211> LENGTH: 33
<212> TYPE: DNA
<213> ORGANISM: Artificial Sequence
<220> FEATURE:
<223> OTHER INFORMATION: Synthetic Primer 3'ritx_kap_bh_Bgl

<400> SEQUENCE: 40
gactagatct tcagcactca ccgcggttaa agg                                      33

<210> SEQ ID NO 41
<211> LENGTH: 702
<212> TYPE: DNA
<213> ORGANISM: Artificial Sequence
<220> FEATURE:
<223> OTHER INFORMATION: Optimized Sec1

<400> SEQUENCE: 41
atgaagttcg cgacctcggt cgcaattttg cttgtggcca acatagccac cgccctcgcg         60
cagatcgtcc tcagccagtc ccccgccatc ctttccgctt cccccggtga aaggtgacc         120 atgacctgcc gcgctagctc ctccgtctcg tacatccact ggttccagca aagcccggc         180 tcgtccccca agccctggat ctacgccacc tccaacctcg cctccggtgt tcccgttcgt        240
ttttccggtt ccggttccgg cacctcctac tccctcacca tctcccgcgt cgaggccgag        300
gatgccgcca cctactactg ccagcagtgg accagcaacc ccccaccctt cggcggtggt        360
acgaagctcg agattaagcg caccgtcgcc gccccctccg tcttcatttt tcccccctcc        420
gatgagcagc tcaagtccgg taccgcctcc gtcgtttgcc tcctcaacaa cttctacccc        480
cgtgaggcca aggtccagtg gaaggtcgac aacgcgcttc agtccggtaa ctcccaggag        540
tccgtcaccg agcaggattc gaaggacagc acctactccc tctcctccac cctcacccctc       600 tccaaggcca actacgagaa gcacaaggtc tacgcctgcg aggtcacgca ccagggtctt        660
tcctcccccg tcacgaagtc ctttaaccgc ggtgagtgct ga                           702

<210> SEQ ID NO 42
<211> LENGTH: 853
<212> TYPE: DNA
<213> ORGANISM: Schizochytrium

<400> SEQUENCE: 42
ctccatcgat cgtgcggtca aaagaaagg aagaagaaag gaaaagaaa ggcgtgcgca           60 cccgagtgcg cgctgagcgc ccgctcgcgg ccccgcggag cctccgcgtt agtccccgcc        120
ccgcgccgcg cagtccccc ggaggcatcg cgcacctctc gccgcccct cgcgcctcgc         180 cgattccccg cctcccctttt tccgcttctt cgccgcctcc gctcgcggcc gcgtcgcccg       240
cgccccgctc cctatctgct ccccaggggg gcactccgca cctttttgcgc ccgctgccgc      300 cgccgcggcc gccccgccgc cctggtttcc cccgcgagcg cggccgcgtc gccgcgcaaa       360
gactcgccgc gtgccgcccc gagcaacggg tggcggcggc gcggcggcgg cggggcgcg        420 gcggcgcgta ggcggggcta ggcgccggct aggcgaaacg ccgcccccgg gcgccgccgc       480
cgcccgctcc agagcagtcg ccgcgccaga ccgccaacgc agagaccgag accgaggtac       540
gtcgcgcccg agcacgccgc gacgcgcggc agggacgagg agcacgacgc cgcgccgcgc       600
cgcgcggggg gggggaggga gaggcaggac gcgggagcga gcgtgcatgt tccgcgcga        660 gacgacgccg cgcgcgctgg agaggagata aggcgcttgg atcgcgagag ggccagccag       720
gctggaggcg aaaatggtg gagaggatag tatcttgcgt gcttggacga ggagactgac         780
gaggaggacg gatacgtcga tgatgatgtg cacagagaag aagcagttcg aaagcgacta       840
```

```
ctagcaagca agg                                                     853
```

<210> SEQ ID NO 43
<211> LENGTH: 1064
<212> TYPE: DNA
<213> ORGANISM: Schizochytrium

<400> SEQUENCE: 43

```
ctcttatctg cctcgcgccg ttgaccgccg cttgactctt ggcgcttgcc gctcgcatcc    60
tgcctcgctc gcgcaggcgg gcgggcgagt gggtgggtcc gcagccttcc gcgctcgccc   120
gctagctcgc tcgcgccgtg ctgcagccag cagggcagca ccgcacggca ggcaggtccc   180
ggcgcggatc gatcgatcca tcgatccatc gatccatcga tcgtgcggtc aaaaagaaag   240
gaagaagaaa ggaaaaagaa aggcgtgcgc acccgagtgc gcgctgagcg cccgctcgcg   300
gtcccgcgga gcctccgcgt tagtccccgc cccgcgccgc gcagtccccc gggaggcatc   360
gcgcacctct cgccgccccc tcgcgcctcg ccgattcccc gctcccctt ttccgcttct    420
tgcccgcctc cgctcgcggc gcgtcgccc gcccccgct ccctatctgc tccccagggg    480
ggcactccgc acctttttgcg cccgctgccg ccgccgcggc cgccccgccg ccctggtttc   540
ccccgcgagc gcggccgcgt cgccgcgcaa agactcgccg cgtgccgccc cgagcaacgg   600
gtggcggcgg cgcggcggcg ggcggggcgc ggcggcgcgt aggcggggct aggcgccggc   660
taggcgaaac gccgccccg ggcgccgccg ccgcccgctc cagagcagtc gccgcgccag    720
accgccaacg cagagaccga gaccgaggta cgtcgcgccc gagcacgccg cgacgcgcgg   780
cagggacgag gagcacgacg ccgcgccgcg ccgcgcgggg ggggggaggg agaggcagga   840
cgcgggagcg agcgtgcatg tttccgcgcg agacgacgcc gcgcgcgctg gagaggagat   900
aaggcgcttg gatcgcgaga gggccagcca ggctggaggc gaaaatgggt ggagaggata   960
gtatcttgcg tgcttggacg aggagactga cgaggaggac ggatacgtcg atgatgatgt  1020
gcacagagaa gaagcagttc gaaagcgact actagcaagc aagg                  1064
```

<210> SEQ ID NO 44
<211> LENGTH: 837
<212> TYPE: DNA
<213> ORGANISM: Schizochytrium

<400> SEQUENCE: 44

```
cttcgctttc tcaacctatc tggacagcaa tccgccactt gccttgatcc ccttccgcgc    60
ctcaatcact cgctccacgt ccctcttccc cctcctcatc tccgtgcttt ctctgccccc   120
cccccccccg ccgcggcgtg cgcgcgcgtg gcgccgcggc gcgacacct tccatactat    180
cctcgctccc aaaatgggtt gcgctatagg gcccggctag gcgaaagtct agcaggcact   240
tgcttggcgc agagccgccg cggccgctcg ttgccgcgga tggagaggga gagagagccc   300
gcctcgataa gcagagacag acagtgcgac tgacagacag acagagagac tggcagaccg   360
gaataccctcg aggtgagtgc ggcgcgggcg agcgggcggg agcgggagcg caagagggac   420
ggcgcggcgc ggcggccctg cgcgacgccg cggcgtattc tcgtgcgcag cgccgagcag   480
cgggacgggg ggctggctga tggttgaagc ggggcggggt gaaatgttag atgagatgat   540
catcgacgac ggtccgtgcg tcttggctgg cttggctggc ttggctggcg ggcctgccgt   600
gtttgcgaga aagaggatga ggagagcgac gaggaaggac gagaagactg acgtgtaggg   660
cgcgcgatgg atgatcgatt gattgattga ttgattggtt gattggctgt gtggtcgatg   720
```

| | |
|---|---|
| aacgtgtaga ctcagggagc gtggttaaat tgttcttgcg ccagacgcga ggactccacc | 780 |
| cccttctttc gcctttacac agccttttg tgaagcaaca agaaagaaaa agccaag | 837 |

<210> SEQ ID NO 45
<211> LENGTH: 1020
<212> TYPE: DNA
<213> ORGANISM: Schizochytrium

<400> SEQUENCE: 45

| | |
|---|---|
| ctttttccgc tctgcataat cctaaaagaa agactatacc ctagtcactg tacaaatggg | 60 |
| acatttctct cccgagcgat agctaaggat ttttgcttcg tgtgcactgt gtgctctggc | 120 |
| cgcgcatcga aagtccagga tcttactgtt tctctttcct ttcctttatt tcctgttctc | 180 |
| ttcttcgctt tctcaaccta tctggacagc aatccgccac ttgccttgat ccccttccgc | 240 |
| gcctcaatca ctcgctccac gtccctcttc cccctcctca tctccgtgct ttctctcgcc | 300 |
| ccccccccc ccgccgcggc gtgcgcgcgc gtggcgccgc ggccgcgaca ccttccatac | 360 |
| tatcctcgct cccaaaatgg gttgcgctat agggcccggc taggcgaaag tctagcaggc | 420 |
| acttgcttgg cgcagagccg ccgcggccgc tcgttgccgc ggatggagag ggagagagag | 480 |
| cccgcctcga taagcagaga cagacagtgc gactgacaga cagacagaga gactggcaga | 540 |
| ccggaatacc tcgaggtgag tgcggcgcgg gcgagcgggc gggagcggga gcgcaagagg | 600 |
| gacggcgcg cgcggcggcc ctgcgcgacg ccgcggcgta ttctcgtgcg cagcgccgag | 660 |
| cagcgggacg ggcggctggc tgatggttga agcggggcgg ggtgaaatgt tagatgagat | 720 |
| gatcatcgac gacggtccgt gcgtcttggc tggcttggct ggcttggctg gcgggcctgc | 780 |
| cgtgtttgcg agaaagagga tgaggagagc gacgaggaag gacgagaaga ctgacgtgta | 840 |
| gggcgcgcga tggatgatcg attgattgat tgattgattg gttgattggc tgtgtggtcg | 900 |
| atgaacgtgt agactcaggg agcgtggtta aattgttctt gcgccagacg cgaggactcc | 960 |
| accccccttct ttcgccttta cacagccttt ttgtgaagca acaagaaaga aaaagccaag | 1020 |

<210> SEQ ID NO 46
<211> LENGTH: 1416
<212> TYPE: DNA
<213> ORGANISM: Schizochytrium

<400> SEQUENCE: 46

| | |
|---|---|
| cccgtccttg acgccttcgc ttccggcgcg gccatcgatt caattcaccc atccgatacg | 60 |
| ttccgccccc tcacgtccgt ctgcgcacga cccctgcacg accacgccaa ggccaacgcg | 120 |
| ccgctcagct cagcttgtcg acgagtcgca cgtcacatat ctcagatgca ttgcctgcct | 180 |
| gcctgcctgc ctgcctgcct gcctgcctgc ctgcctgcct cagcctctct ttgctctctc | 240 |
| tgcggcggcc gctgcgacgc gctgtacagg agaatgactc caggaagtgc ggctgggata | 300 |
| cgcgctggcg tcggccgtga tgcgcgtgac gggcggcggg cacggccggc acgggttgag | 360 |
| cagaggacga agcgaggcga gacgagacag gccaggcgcg gggagcgctc gctgccgtga | 420 |
| gcagcagacc agggcgcagg aatgtacttt tcttgcggga gcggagacga ggctgccggc | 480 |
| tgctggctgc cggttgctct gcacgcgccg cccgacttgg cgtagcgtgg acgcgcggcg | 540 |
| gcggccgccg tctcgtcgcg gtcggctttg ccgtgtatcg acgctgcggg cttgacacgg | 600 |
| gatggcggaa gttcagcatc gctgcgatcc ctcgcgccgc agaacgagga gagcgcaggc | 660 |
| cggcttcaag tttgaaagga gaggaaggca ggcaaggagc tggaagcttg ccgcggaagg | 720 |
| cgcaggcatg cgtcacgtga aaaaaaggga tttcaagagt agtaagtagg tatggtctac | 780 |

```
aagtcccta ttcttacttc gcggaacgtg ggctgctcgt gcgggcgtcc atcttgtttt    840 tgttttttt tccgctaggc gcgtgcattg cttgatgagt ctcagcgttc gtctgcagcg    900
agggcaggaa ataagcggc ccgtgccgtc gagcgcacag gacgtgcaag cgccttgcga   960
gcgcagcatc cttgcacggc gagcatagag accgcggccg atggactcca gcaggaatt   1020 ttcgaccctc tctatcaagc tgcgcttgac agccgggaat ggcagcctga ggagagaggg   1080
gcgaaggaag ggactggagg aaaagaggta aggcaccctc aatcacggcg cgtgaaagcc   1140
agtcatccct cgcaaagaaa agacaaaagc gggttttttg tttcgatggg aaagaatttc   1200
ttagaggaag aagcggcaca cagactcgcg ccatgcagat ttctgcgcag ctcgcgatca   1260
aaccaggaac gtggtcgctg cgcgccacta tcaggggtag cgcacgaata ccaaacgcat   1320
tactagctac gcgcctgtga cccgaggatc gggccacaga cgttgtctct tgccatccca   1380
cgacctggca gcgagaagat cgtccattac tcatcg                            1416
```

<210> SEQ ID NO 47
<211> LENGTH: 24
<212> TYPE: DNA
<213> ORGANISM: Artificial Sequence
<220> FEATURE:
<223> OTHER INFORMATION: Synthetic Primer 5'60S-807

<400> SEQUENCE: 47
tcgatttgcg gatacttgct caca                                          24

<210> SEQ ID NO 48
<211> LENGTH: 21
<212> TYPE: DNA
<213> ORGANISM: Artificial Sequence
<220> FEATURE:
<223> OTHER INFORMATION: Synthetic Primer 3'60S-2821

<400> SEQUENCE: 48
gacgacctcg cccttggaca c                                             21

<210> SEQ ID NO 49
<211> LENGTH: 34
<212> TYPE: DNA
<213> ORGANISM: Artificial Sequence
<220> FEATURE:
<223> OTHER INFORMATION: Synthetic Primer 5'60Sp-1302-Kpn

<400> SEQUENCE: 49
gactggtacc tttttccgct ctgcataatc ctaa                               34

<210> SEQ ID NO 50
<211> LENGTH: 32
<212> TYPE: DNA
<213> ORGANISM: Artificial Sequence
<220> FEATURE:
<223> OTHER INFORMATION: Synthetic Primer 3'60Sp-Bam

<400> SEQUENCE: 50
gactggatcc ttggcttttt ctttcttgtt gc                                 32

<210> SEQ ID NO 51
<211> LENGTH: 24
<212> TYPE: DNA
<213> ORGANISM: Artificial Sequence
<220> FEATURE:
<223> OTHER INFORMATION: Synthetic Primer 5'EF1-68

```
<400> SEQUENCE: 51
cgccgttgac cgccgcttga ctct                                           24

<210> SEQ ID NO 52
<211> LENGTH: 24
<212> TYPE: DNA
<213> ORGANISM: Artificial Sequence
<220> FEATURE:
<223> OTHER INFORMATION: Synthetic Primer 3'EF1-2312

<400> SEQUENCE: 52
cgggggtagc ctcggggatg gact                                           24

<210> SEQ ID NO 53
<211> LENGTH: 34
<212> TYPE: DNA
<213> ORGANISM: Artificial Sequence
<220> FEATURE:
<223> OTHER INFORMATION: Synthetic Primer 5'EF1-54-Kpn

<400> SEQUENCE: 53
gactggtacc tcttatctgc ctcgcgccgt tgac                                34

<210> SEQ ID NO 54
<211> LENGTH: 37
<212> TYPE: DNA
<213> ORGANISM: Artificial Sequence
<220> FEATURE:
<223> OTHER INFORMATION: Synthetic Primer 5'EF1-1114-Bam

<400> SEQUENCE: 54
gactggatcc cttgcttgct agtagtcgct ttcgaac                             37

<210> SEQ ID NO 55
<211> LENGTH: 29
<212> TYPE: DNA
<213> ORGANISM: Artificial Sequence
<220> FEATURE:
<223> OTHER INFORMATION: Synthetic Primer 5'Sec1P-kpn

<400> SEQUENCE: 55
gactggtacc ccgtccttga cgccttcgc                                      29

<210> SEQ ID NO 56
<211> LENGTH: 31
<212> TYPE: DNA
<213> ORGANISM: Artificial Sequence
<220> FEATURE:
<223> OTHER INFORMATION: Synthetic Primer 3'Sec1P-ba

<400> SEQUENCE: 56
gactggatcc gatgagtaat ggacgatctt c                                   31

<210> SEQ ID NO 57
<211> LENGTH: 1614
<212> TYPE: DNA
<213> ORGANISM: Artificial sequence
<220> FEATURE:
<223> OTHER INFORMATION: Secretion signal

<400> SEQUENCE: 57
ggatccatga agttcgcgac ctcggtcgca attttgcttg tggccaacat agccaccgcc    60
ctcgcgtcga tgaccaacga gacctcggac cgccctctcg tgcactttac ccccaacaag   120
ggttggatga acgatcccaa cggcctctgg tacgacgaga aggatgctaa gtggcacctt   180
```

```
tactttcagt acaaccctaa cgacaccgtc tggggcaccc cgctcttctg gggccacgcc      240
acctccgacg acctcaccaa ctgggaggac cagcccattg ctatcgcccc caagcgcaac      300
gactcgggag cttttccgg ttccatggtt gtggactaca acaacacctc cggttttttt      360
aacgacacca ttgacccccg ccagcgctgc gtcgccatct ggacctacaa cacgcccgag      420
agcgaggagc agtacatcag ctacagcctt gatggaggct acacctttac cgagtaccag      480
aagaaccctg tcctcgccgc caactccacc cagttccgcg accctaaggt ttttggtac      540 gagccttccc agaagtggat tatgaccgcc gctaagtcgc aggattacaa gatcgagatc      600
tacagcagcg acgacctcaa gtcctggaag cttgagtccg cctttgccaa cgagggtttt      660
ctcggatacc agtacgagtg ccccggtctc atcgaggtcc ccaccgagca ggacccgtcc      720
aagtcctact gggtcatgtt tatttccatc aaccctggcg ccctgccgg cggcagcttc      780 aaccagtact cgtcggctc ctttaacggc acgcattttg aggccttcga caaccagtcc      840
cgcgtcgtcg acttcggcaa ggactactac gccctccaga ccttctttaa caccgacccc      900
acctacggca gcgccctcgg tattgcttgg gcctccaact gggagtactc cgctttcgtc      960
cccactaacc cctggcgcag ctcgatgtcc ctcgtccgca gttttcgct taacaccgag     1020 taccaggcca accccgagac cgagcttatt aacctgaagg ccgagcctat tctcaacatc     1080
tccaacgctg gccctggtc ccgctttgct actaacacta ccctcaccaa ggccaactcc     1140
tacaacgtcg atctctccaa ctccaccggt actcttgagt tgagctcgt ctacgccgtc     1200 aacaccaccc agaccatctc caagtccgtc ttcgccgacc tctccctctg gttcaagggc     1260
cttgaggacc ccgaggagta cctgcgcatg ggttttgagg tctccgcctc ctccttcttc     1320
ctcgatcgcg gtaactccaa ggttaagttt gtcaaggaga accccttact tactaaccgt     1380
atgagcgtca caaccagcc ctttaagtcc gagaacgatc ttagctacta caaggtttac     1440
ggcctcctcg accagaacat tctcgagctc tactttaacg acggagatgt cgtcagcacc     1500
aacacctact ttatgaccac tggaaacgcc ctcggcagcg tgaacatgac caccggagtc     1560
gacaacctct tttacattga caagtttcag gttcgcgagg ttaagtaaca tatg          1614
```

<210> SEQ ID NO 58
<211> LENGTH: 11495
<212> TYPE: DNA
<213> ORGANISM: Artificial sequence
<220> FEATURE:
<223> OTHER INFORMATION: pCL0076

<400> SEQUENCE: 58

```
ctcttatctg cctcgcgccg ttgaccgccg cttgactctt ggcgcttgcc gctcgcatcc       60
tgcctcgctc gcgcaggcgg gcgggcgagt gggtgggtcc gcagccttcc gcgctcgccc      120
gctagctcgc tcgcgccgtg ctgcagccag cagggcagca ccgcacggca ggcaggtccc      180
ggcgcggatc gatcgatcca tcgatccatc gatccatcga tcgtgcggtc aaaaagaaag      240
gaagaagaaa ggaaaaagaa aggcgtgcgc acccgagtgc gcgctgagcg cccgctcgcg      300
gtcccgcgga gcctccgcgt tagtcccgc cccgcgccgc gcagtccccc gggaggcatc      360
gcgcacctct cgccgccccc tcgcgcctcg ccgattcccc gcctcccctt ttccgcttct      420
tcgccgcctc cgctcgcggc gcgtcgcccc gcgccccgct ccctatctgc tccccagggg      480
ggcactccgc accttttgcg cccgctgccg ccgccgcggc gccccgccg ccctggtttc      540 ccccgcgagc gcggccgcgt cgccgcgcaa agactcgccg cgtgccgccc cgagcaacgg      600
```

```
gtggcggcgg cgcggcggcg ggcggggcgc ggcggcgcgt aggcggggct aggcgccggc    660
taggcgaaac gccgccccg  ggcgccgccg ccgcccgctc cagagcagtc gccgcgccag    720
accgccaacg cagagaccga gaccgaggta cgtcgcgccc gagcacgccg cgacgcgcgg    780
cagggacgag gagcacgacg ccgcgccgcg ccgcgcgggg gggggagggg agaggcagga    840
cgcgggagcg agcgtgcatg tttccgcgcg agacgacgcc gcgcgcgctg gagaggagat    900
aaggcgcttg gatcgcgaga gggccagcca ggctggaggc gaaaatgggt ggagaggata    960
gtatcttgcg tgcttggacg aggagactga cgaggaggac ggatacgtcg atgatgatgt    1020
gcacagagaa gaagcagttc gaaagcgact actagcaagc aagggatcca tgaagttcgc    1080
gacctcggtc gcaattttgc ttgtggccaa catagccacc gccctcgcgt cgatgaccaa    1140
cgagacctcg gaccgccctc tcgtgcactt taccccaac  aagggttgga tgaacgatcc    1200
caacggcctc tggtacgacg agaaggatgc taagtggcac ctttactttc agtacaaccc    1260
taacgacacc gtctggggca ccccgctctt ctggggccac gccacctccg acgacctcac    1320
caactgggag gaccagccca ttgctatcgc ccccaagcgc aacgactcgg agcttttttc    1380
cggttccatg gttgtggact acaacaacac ctccggtttt tttaacgaca ccattgaccc    1440
ccgccagcgc tgcgtcgcca tctggaccta caacacgccc gagagcgagg agcagtacat    1500
cagctacagc cttgatggag gctacacctt taccgagtac cagaagaacc ctgtcctcgc    1560
cgccaactcc acccagttcc gcgacccta  ggttttttgg tacgagcctt cccagaagtg    1620
gattatgacc gccgctaagt cgcaggatta caagatcgag atctacagca gcgacgacct    1680
caagtcctgg aagcttgagt ccgcctttgc caacgagggt tttctcggat accagtacga    1740
gtgccccggt ctcatcgagg tccccaccga gcaggacccg tccaagtcct actgggtcat    1800
gtttatttcc atcaaccctg gcgccctgc  cggcggcagc ttcaaccagt acttcgtcgg    1860
ctcctttaac ggcacgcatt ttgaggcctt cgacaaccag tcccgcgtcg tcgacttcgg    1920
caaggactac tacgccctcc agaccttctt taacaccgac cccacctacg cagcgccct    1980 cggtattgct tgggcctcca actgggagta ctccgctttc gtccccacta accctggcg    2040 cagctcgatg tccctcgtcc gcaagttttc gcttaacacc gagtaccagg ccaaccccga    2100
gaccgagctt attaacctga aggccgagcc tattctcaac atctccaacg ctggcccctg    2160
gtcccgcttt gctactaaca ctaccctcac caaggccaac tcctacaacg tcgatctctc    2220
caactccacc ggtactcttg agtttgagct cgtctacgcc gtcaacacca cccagaccat    2280
ctccaagtcc gtcttcgccg acctctccct ctggttcaag ggccttgagg accccgagga    2340
gtacctgcgc atgggttttg aggtctccgc ctcctccttc ttcctcgatc gcggtaactc    2400
caaggttaag tttgtcaagg agaaccccta ctttactaac cgtatgagcg tcaacaacca    2460 gcccttaag  tccgagaacg atcttagcta ctacaaggtt tacggcctcc tcgaccagaa    2520
cattctcgag ctctacttta cgacggaga  tgtcgtcagc accaacacct acttatgac     2580 cactggaaac gccctcggca gcgtgaacat gaccaccgga gtcgacaacc tcttttacat    2640
tgacaagttt caggttcgcg aggttaagta acatatgtta tgagagatcc gaaagtgaac    2700
cttgtcctaa cccgacagcg aatgcgggga ggggcgggc  taaagatcg  tattacatag    2760 tatttttccc ctactctttg tgtttgtctt ttttttttt  ttgaacgcat tcaagccact    2820
tgtctgggtt tacttgtttg tttgcttgct tgcttgcttg cttgcctgct tcttggtcag    2880
acggcccaaa aagggaaaa  aattcattca tggcacagat aagaaaaaga aaagtttgt     2940 cgaccaccgt catcagaaag caagagaaga gaaacactcg cgctcacatt ctcgctcgcg    3000
```

```
taagaatctt agccacgcat acgaagtaat ttgtccatct ggcgaatctt tacatgagcg   3060
ttttcaagct ggagcgtgag atcataccct tcttgatcgt aatgttccaa ccttgcatag   3120
gcctcgttgc gatccgctag caatgcgtcg tactcccgtt gcaactgcgc catcgcctca   3180
ttgtgacgtg agttcagatt cttctcgaga ccttcgagcg ctgctaattt cgcctgacgc   3240
tccttctttt gtgcttccat gacacgccgc ttcaccgtgc gttccacttc ttcctcagac   3300
atgcccttgg ctgcctcgac ctgctcggta agcttcgtcg taatctcctc gatctcggaa   3360
ttcttcttgc cctccatcca ctcggcacca tacttggcag cctgttcaac acgtcattg    3420 aaaaactttt cattctcttc cagctccgca acccgcgctc gaagctcatt cacttccgcc   3480
accacggctt cggcatcgag cgccgaatca gtcgccgaac tttccgaaag atacaccacg   3540
gcccctccgc tgctgctgcg cagcgtcatc atcagtcgcg tgttatcttc gcgcagattc   3600
tccacctgct ccgtaagcag cttcacggtg gcctcttgat tctgagggct cacgtcgtgg   3660
attagcgctt gcagctcttg cagctccgtc agcttggaag agctcgtaat catggctttg   3720
cacttgtcca gacgtcgcag agcgttcgag agccgcttcg cgttatctgc catggacgct   3780
tctgcgctcg cggcctccct gacgacagtc tcttgcagtt tcactagatc atgtccaatc   3840
agcttgcggt gcagctctcc aatcacgttc tgcatcttgt ttgtgtgtcc gggccgcgcc   3900
tcgtcttgcg atttgcgaat ttcctcctcg agctcgcgtt cgagctccag ggcgcccttta  3960 agtagctcga agtcagccgc cgttagcccc agctccgtcg ccgcgttcag acagtcggtt   4020
agcttgattc gattccgctt ttccatggca agtttaagat cctggcccag ctgcacctcc   4080
tgcgccttgc gcatcatgcg cggttccgcc tggcgcaaaa gcttcgagtc gtatcctgcc   4140
tgccatgcca gcgcaatggc acgcacgagc gacttgagtt gccaactatt catcgccgag   4200
atgagcagca ttttgatctg catgaacacc tcgtcagagt cgtcatcctc tgcctcctcc   4260
agctctgcgg gcgagcgacg ctctccttgc agatgaagcg agggccgcag gcctccgaag   4320
agcacctctt gcgcgagatc ctcctccgtc gtcgccctcc gcaggattgc ggtcgtgtcc   4380
gccatcttgc cgccacagca gcttttgctc gctctgcacc ttcaatttct ggtgccgctg   4440
gtgccgctgg tgccgcttgt gctggtgctg gtgctggtgc tggtgctggt gccttgtgct   4500
ggtgctgcca cagacaccgc cgctcctgct gctgctcttc cggcccccctc gccgccgccg   4560 cgagcccccg ccgcgcgccg tgcctgggct ctccgcgctc tccgcgggct cctcggcctc   4620
ggcctcgccg tccgcgacga cgtctgcgcg gccgatggtg cggatctgct ctagagggcc   4680
cttcgaaggt aagcctatcc ctaaccctct cctcggtctc gattctacgc gtaccggtca   4740
tcatcaccat caccattgag tttaaacggg ccccagcacg tgctacgaga tttcgattcc   4800
accgccgcct tctatgaaag gttgggcttc ggaatcgttt tccgggacgc cggctggatg   4860
atcctccagc gcggggatct catgctggag ttcttcgccc accccaactt gtttattgca   4920
gcttataatg gttacaaata agcaatagc atcacaaatt tcacaaataa agcattttt    4980 tcactgcatt ctagttgtgg tttgtccaaa ctcatcaatg tatcttatca tacatggtcg   5040
acctgcagga acctgcatta atgaatcggc caacgcgcgg ggagaggcgg tttgcgtatt   5100
gggcgctctt ccgcttcctc gctcactgac tcgctgcgct cggtcgttcg gctgcggcga   5160
gcggtatcag ctcactcaaa ggcggtaata cggttatcca cagaatcagg ggataacgca   5220
ggaaagaaca tgtgagcaaa aggccagcaa aaggccagga accgtaaaaa ggccgcgttg   5280
ctggcgtttt tccataggct ccgcccccct gacgagcatc acaaaaatcg acgctcaagt   5340
```

```
cagaggtggc gaaacccgac aggactataa agataccagg cgtttccccc tggaagctcc    5400
ctcgtgcgct ctcctgttcc gaccctgccg cttaccggat acctgtccgc ctttctccct    5460
tcgggaagcg tggcgctttc tcatagctca cgctgtaggt atctcagttc ggtgtaggtc    5520
gttcgctcca agctgggctg tgtgcacgaa ccccccgttc agcccgaccg ctgcgcctta    5580
tccggtaact atcgtcttga gtccaacccg gtaagacacg acttatcgcc actggcagca    5640
gccactggta acaggattag cagagcgagg tatgtaggcg gtgctacaga gttcttgaag    5700
tggtggccta actacggcta cactagaaga acagtatttg gtatctgcgc tctgctgaag    5760
ccagttacct tcggaaaaag agttggtagc tcttgatccg gcaaacaaac caccgctggt    5820
agcggtggtt ttttgtttg caagcagcag attacgcgca gaaaaaagg atctcaagaa       5880
gatcctttga tcttttctac ggggtctgac gctcagtgga acgaaaactc acgttaaggg    5940
attttggtca tgagattatc aaaaaggatc ttcacctaga tccttttaaa ttaaaaatga    6000
agttttaaat caatctaaag tatatatgag taaacttggt ctgacagtta ccaatgctta    6060
atcagtgagg cacctatctc agcgatctgt ctatttcgtt catccatagt tgcctgactc    6120
cccgtcgtgt agataactac gatacgggag ggcttaccat ctggccccag tgctgcaatg    6180
ataccgcgag acccacgctc accggctcca gatttatcag caataaacca gccagccgga    6240
agggccgagc gcagaagtgg tcctgcaact ttatccgcct ccatccagtc tattaattgt    6300
tgccgggaag ctagagtaag tagttcgcca gttaatagtt tgcgcaacgt tgttgccatt    6360
gctacaggca tcgtggtgtc acgctcgtcg tttggtatgg cttcattcag ctccggttcc    6420
caacgatcaa ggcgagttac atgatccccc atgttgtgca aaaaagcggt tagctccttc    6480
ggtcctccga tcgttgtcag aagtaagttg gccgcagtgt tatcactcat ggttatggca    6540
gcactgcata attctcttac tgtcatgcca tccgtaagat gcttttctgt gactggtgag    6600
tactcaacca agtcattctg agaatagtgt atgcggcgac cgagttgctc ttgcccggcg    6660
tcaatacggg ataataccgc gccacatagc agaactttaa aagtgctcat cattggaaaa    6720
cgttcttcgg ggcgaaaact ctcaaggatc ttaccgctgt tgagatccag ttcgatgtaa    6780
cccactcgtg cacccaactg atcttcagca tcttttactt tcaccagcgt ttctgggtga    6840
gcaaaaacag gaaggcaaaa tgccgcaaaa aagggaataa gggcgacacg gaaatgttga    6900
atactcatac tcttcctttt tcaatattat tgaagcattt atcagggtta ttgtctcatg    6960
agcggataca tatttgaatg tatttagaaa aataaacaaa taggggttcc gcgcacattt    7020
ccccgaaaag tgccacctga cgtctaagaa accattatta tcatgacatt aacctataaa    7080
aataggcgta tcacgaggcc ctttcgtctc gcgcgtttcg gtgatgacgg tgaaaacctc    7140
tgacacatgc agctcccgga gacggtcaca gcttgtctgt aagcggatgc cgggagcaga    7200
caagcccgtc agggcgcgtc agcgggtgtt ggcgggtgtc ggggctggct taactatgcg    7260
gcatcagagc agattgtact gagagtgcac caagctttgc ctcaacgcaa ctaggcccag    7320
gcctactttc actgtgtctt gtcttgcctt tcacaccgac cgagtgtgca caaccgtgtt    7380
ttgcacaaag cgcaagatgc tcactcgact gtgaagcaaa ggttgcgcgc aagcgactgc    7440
gactgcgagg atgaggatga ctggcagcct gttcaaaaac tgaaaatccg cgatgggtca    7500
gctgccattc gcgcatgacg cctgcgagag acaagttaac tcgtgtcact ggcatgtcct    7560
agcatcttta cgcgagcaaa attcaatcgc tttatttttt cagtttcgta accttctcgc    7620
aaccgcgaat cgccgtttca gcctgactaa tctgcagctg cgtggcactg tcagtcagtc    7680
agtcagtcgt gcgcgctgtt ccagcaccga ggtcgcgcgt cgccgcgcct ggaccgctgc    7740
```

-continued

```
tgctactgct agtggcacgg caggtaggag cttgttgccg gaacaccagc agccgccagt   7800
cgacgccagc caggggaaag tccggcgtcg aagggagagg aaggcggcgt gtgcaaacta   7860
acgttgacca ctggcgcccg ccgacacgag caggaagcag gcagctgcag agcgcagcgc   7920
gcaagtgcag aatgcgcgaa agatccactt gcgcgcggcg ggcgcgcact tgcgggcgcg   7980
gcgcggaaca gtgcggaaag gagcggtgca gacggcgcgc agtgacagtg ggcgcaaagc   8040
cgcgcagtaa gcagcggcgg ggaacggtat acgcagtgcc gcgggccgcc gcacacagaa   8100
gtatacgcgg gccgaagtgg ggcgtcgcgc gcgggaagtg cggaatggcg ggcaaggaaa   8160
ggaggagacg gaaagagggc gggaaagaga gagagagaga gtgaaaaaag aaagaaagaa   8220
agaaagaaag aaagaaagct cggagccacg ccgcggggag agagagaaat gaaagcacgg   8280
cacggcaaag caaagcaaag cagacccagc cagacccagc cgagggagga gcgcgcgcag   8340
gacccgcgcg gcgagcgagc gagcacggcg cgcgagcgag cgagcgagcg agcgcgcgag   8400
cgagcaaggc ttgctgcgag cgatcgagcg agcgagcggg aaggatgagc gcgacccgcg   8460
cggcgacgag gacagcggcg gcgctgtcct cggcgctgac gacgcctgta aagcagcagc   8520
agcagcagca gctgcgcgta ggcgcggcgt cggcacggct ggcggccgcg gcgttctcgt   8580
ccggcacggg cggagacgcg gccaagaagg cggccgcggc gagggcgttc tccacgggac   8640
gcggccccaa cgcgacacgc gagaagagct cgctggccac ggtccaggcg gcgacggacg   8700
atgcgcgctt cgtcggcctg accggcgccc aaatctttca tgagctcatg cgcgagcacc   8760
aggtggacac catctttggc taccctggcg gcgccattct gcccgttttt gatgccattt   8820
ttgagagtga cgcgcttcaa gttcattctc gctcgccacg agcagggcgc cggccacatg   8880
gccgagggct acgcgcgcgc cacgggcaag cccggcgttg tcctcgtcac ctcgggccct   8940
ggagccacca acaccatcac cccgatcatg gatgcttaca tggacggtac gccgctgctc   9000
gtgttcaccg gccaggtgca gacctctgct gtcggcacgg acgctttcca ggagtgtgac   9060
attgttggca tcagccgcgc gtgcaccaag tggaacgtca tggtcaagga cgtgaaggag   9120
ctcccgcgcc gcatcaatga ggcctttgag attgccatga gcggccgccc gggtcccgtg   9180
ctcgtcgatc ttcctaagga tgtgaccgcc gttgagctca aggaaatgcc cgacagctcc   9240
ccccaggttg ctgtgcgcca gaagcaaaag gtcgagcttt ccacaagga gcgcattggc   9300
gctcctggca cggccgactt caagctcatt gccgagatga tcaaccgtgc ggagcgaccc   9360
gtcatctatg ctggccaggg tgtcatgcag agcccgttga atggcccggc tgtgctcaag   9420
gagttcgcgc agaaggccaa cattcccgtg accaccacca tgcagggtct cggcggcttt   9480
gacgagcgta gtcccctctc cctcaagatg ctcggcatgc acggctctgc ctacgccaac   9540
tactcgatgc agaacgccga tcttatcctg gcgctcggtg cccgctttga tgatcgtgtg   9600
acgggccgcg ttgacgcctt tgctccggag gctcgccgtg ccgagcgcga gggccgcggt   9660
ggcatcgttc actttgagat ttcccccaag aacctccaca aggtcgtcca gcccaccgtc   9720
gcggtcctcg gcgacgtggt cgagaacctc gccaacgtca cgccccacgt gcagcgccag   9780
gagcgcgagc cgtggtttgc gcagatcgcc gattggaagg agaagcaccc ttttctgctc   9840
gagtctgttg attcggacga caaggttctc aagccgcagc aggtcctcac ggagcttaac   9900
aagcagattc tcgagattca ggagaaggac gccgaccagg aggtctacat caccacgggc   9960
gtcggaagcc accagatgca ggcagcgcag ttccttacct ggaccaagcc gcgccagtgg  10020
atctcctcgg gtggcgccgg cactatgggc tacggccttc cctcggccat tggcgccaag  10080
```

```
attgccaagc cgatgctat tgttattgac atcgatggtg atgcttctta ttcgatgacc    10140
ggtatggaat tgatcacagc agccgaattc aaggttggcg tgaagattct tcttttgcag    10200
aacaactttc agggcatggt caagaacgtt caggatctct tttacgacaa gcgctactcg    10260
ggccaccgcc atgttcaacc cgcgcttcga caaggtcgcc gatgcgatgc gtgccaaggg    10320
tctctactgc gcgaaacagt cggagctcaa ggacaagatc aaggagtttc tcgagtacga    10380
tgagggtccc gtcctcctcg aggttttcgt ggacaaggac acgctcgtct tgcccatggt    10440
ccccgctggc tttccgctcc acgagatggt cctcgagcct cctaagccca aggacgccta    10500
agttcttttt tccatggcgg gcgagcgagc gagcgcgcga gcgcgcaagt gcgcaagcgc    10560
cttgccttgc tttgcttcgc ttcgctttgc tttgcttcac acaacctaag tatgaattca    10620
agttttcttg cttgtcggcg atgcctgcct gccaaccagc cagccatccg gccgccgtc    10680 cttgacgcct tcgcttccgg cgcggccatc gattcaattc acccatccga tacgttccgc    10740
cccctcacgt ccgtctgcgc acgacccctg cacgaccacg ccaaggccaa cgcgccgctc    10800
agctcagctt gtcgacgagt cgcacgtcac atatctcaga tgcatttgga ctgtgagtgt    10860
tattatgcca ctagcacgca acgatcttcg gggtcctcgc tcattgcatc cgttcgggcc    10920
ctgcaggcgt ggacgcgagt cgccgccgag acgctgcagc aggccgctcc gacgcgaggg    10980
ctcgagctcg ccgcgcccgc gcgatgtctg cctggcgccg actgatctct ggagcgcaag    11040
gaagacacgc gacgcgagg aggaccgaag agagacgctg gggtatgcag gatatacccg    11100
gggcgggaca ttcgttccgc atacactccc ccattcgagc ttgctcgtcc ttggcagagc    11160
cgagcgcgaa cggttccgaa gcggcaagg attttggctc tggtgggtgg actccgatcg    11220
aggcgcaggt tctccgcagg ttctcgcagg ccggcagtgg tcgttagaaa tagggagtgc    11280
cggagtcttg acgcgcctta gctcactctc cgcccacgcg cgcatcgccg ccatgccgcc    11340
gtcccgtctg tcgctgcgct ggccgcgacc ggctgcgcca gagtacgaca gtgggacaga    11400
gctcgaggcg acgcgaatcg ctcgggttgt aagggtttca agggtcgggc gtcgtcgcgt    11460
gccaaagtga aaatagtagg ggggggggg ggtac                                 11495
```

<210> SEQ ID NO 59
<211> LENGTH: 32
<212> TYPE: PRT
<213> ORGANISM: Schizochytrium

<400> SEQUENCE: 59

Met Arg Thr Val Arg Gly Pro Gln Thr Ala Ala Leu Ala Ala Leu Leu
1               5                   10                  15

Ala Leu Ala Ala Thr His Val Ala Val Ser Pro Phe Thr Lys Val Glu
            20                  25                  30

<210> SEQ ID NO 60
<211> LENGTH: 96
<212> TYPE: DNA
<213> ORGANISM: Schizochytrium

<400> SEQUENCE: 60
atgcgcacgg tgagggggcc gcaaacggcg gcactcgccg cccttctggc acttgccgcg    60
acgcacgtgg ctgtgagccc gttcaccaag gtggag                              96

<210> SEQ ID NO 61
<211> LENGTH: 30
<212> TYPE: PRT
<213> ORGANISM: Schizochytrium

<400> SEQUENCE: 61

Met Gly Arg Leu Ala Lys Ser Leu Val Leu Leu Thr Ala Val Leu Ala
1               5                   10                  15

Val Ile Gly Gly Val Arg Ala Glu Glu Asp Lys Ser Glu Ala
            20                  25                  30

<210> SEQ ID NO 62
<211> LENGTH: 90
<212> TYPE: DNA
<213> ORGANISM: Schizochytrium

<400> SEQUENCE: 62
atgggccgcc tcgcgaagtc gcttgtgctg ctgacggccg tgctggccgt gatcggaggc      60
gtccgcgccg aagaggacaa gtccgaggcc                                      90

<210> SEQ ID NO 63
<211> LENGTH: 38
<212> TYPE: PRT
<213> ORGANISM: Schizochytrium

<400> SEQUENCE: 63

Met Thr Ser Thr Ala Arg Ala Leu Ala Leu Val Arg Ala Leu Val Leu
1               5                   10                  15

Ala Leu Ala Val Leu Ala Leu Leu Ala Ser Gln Ser Val Ala Val Asp
            20                  25                  30

Arg Lys Lys Phe Arg Thr
        35

<210> SEQ ID NO 64
<211> LENGTH: 114
<212> TYPE: DNA
<213> ORGANISM: Schizochytrium

<400> SEQUENCE: 64
atgacgtcaa cggcgcgcgc gctcgcgctc gtgcgtgctt tggtgctcgc tctggctgtc      60
ttggcgctgc tagcgagcca aagcgtggcc gtggaccgca aaaagttcag gacc           114

<210> SEQ ID NO 65
<211> LENGTH: 34
<212> TYPE: PRT
<213> ORGANISM: Schizochytrium

<400> SEQUENCE: 65

Met Leu Arg Leu Lys Pro Leu Leu Leu Phe Leu Cys Ser Leu Ile
1               5                   10                  15

Ala Ser Pro Val Val Ala Trp Ala Arg Gly Gly Glu Gly Pro Ser Thr
            20                  25                  30

Ser Glu

<210> SEQ ID NO 66
<211> LENGTH: 102
<212> TYPE: DNA
<213> ORGANISM: Schizochytrium

<400> SEQUENCE: 66
atgttgcggc tcaagccact tttactcctc ttcctctgct cgttgattgc ttcgcctgtg      60
gttgcctggg caagaggagg agaagggccg tccacgagcg aa                       102

```
<210> SEQ ID NO 67
<211> LENGTH: 29
<212> TYPE: PRT
<213> ORGANISM: Schizochytrium

<400> SEQUENCE: 67

Met Ala Lys Ile Leu Arg Ser Leu Leu Ala Val Leu Val Val
1               5                   10                  15

Thr Pro Gln Ser Leu Arg Ala His Ser Thr Arg Asp Ala
            20                  25

<210> SEQ ID NO 68
<211> LENGTH: 87
<212> TYPE: DNA
<213> ORGANISM: Schizochytrium

<400> SEQUENCE: 68
atggccaaga tcttgcgcag tttgctcctg gcggccgtgc tcgtggtgac tcctcaatca        60
ctgcgtgctc attcgacgcg ggacgca                                            87

<210> SEQ ID NO 69
<211> LENGTH: 36
<212> TYPE: PRT
<213> ORGANISM: Schizochytrium

<400> SEQUENCE: 69

Met Val Phe Arg Arg Val Pro Trp His Gly Ala Ala Thr Leu Ala Ala
1               5                   10                  15

Leu Val Val Ala Cys Ala Thr Cys Leu Gly Leu Gly Leu Asp Ser Glu
            20                  25                  30

Glu Ala Thr Tyr
        35

<210> SEQ ID NO 70
<211> LENGTH: 108
<212> TYPE: DNA
<213> ORGANISM: Schizochytrium

<400> SEQUENCE: 70
atggtgtttc ggcgcgtgcc atggcacggc gcggcgacgc tggcggcctt ggtcgtggcc        60
tgcgcgacgt gtttaggcct gggactggac tcggaggagg ccacgtac                    108

<210> SEQ ID NO 71
<211> LENGTH: 30
<212> TYPE: PRT
<213> ORGANISM: Schizochytrium

<400> SEQUENCE: 71

Met Thr Ala Asn Ser Val Lys Ile Ser Ile Val Ala Val Leu Val Ala
1               5                   10                  15

Ala Leu Ala Trp Glu Thr Cys Ala Lys Ala Asn Tyr Gln Trp
            20                  25                  30

<210> SEQ ID NO 72
<211> LENGTH: 90
<212> TYPE: DNA
<213> ORGANISM: Schizochytrium

<400> SEQUENCE: 72
atgacagcta actcggtgaa ataagcatc gtggctgtgc tggtcgcggc actggcttgg        60
gaaacatgcg caaaagctaa ctatcagtgg                                         90
```

<210> SEQ ID NO 73
<211> LENGTH: 35
<212> TYPE: PRT
<213> ORGANISM: Schizochytrium

<400> SEQUENCE: 73

Met Ala Arg Arg Ala Ser Arg Leu Gly Ala Ala Val Val Val Leu
1               5                  10                  15

Val Val Val Ala Ser Ala Cys Cys Trp Gln Ala Ala Asp Val Val
            20                  25                  30

Asp Ala Gln
        35

<210> SEQ ID NO 74
<211> LENGTH: 105
<212> TYPE: DNA
<213> ORGANISM: Schizochytrium

<400> SEQUENCE: 74
atggcgcgca gggcgtcgcg cctcggcgcc gccgtcgtcg tcgtcctcgt cgtcgtcgcc    60
tccgcctgct gctggcaagc cgctgcggac gtcgtggacg cgcag                  105

<210> SEQ ID NO 75
<211> LENGTH: 1785
<212> TYPE: DNA
<213> ORGANISM: Artificial Sequence
<220> FEATURE:
<223> OTHER INFORMATION: Codon optimized nucleic acid sequence

<400> SEQUENCE: 75
atgaagttcg cgacctcggt cgcaattttg cttgtggcca acatagccac cgccctcgcg    60
gcctccccct cgatgcagac ccgtgcctcc gtcgtcattg attacaacgt cgctcctcct   120
aacctctcca ccctcccgaa cggcagcctc tttgagacct ggcgtcctcg cgcccacgtt   180
cttcccccta acggtcagat tggcgatccc tgcctccact acaccgatcc ctcgactggc   240
ctctttcacg tcggctttct ccacgatggc tccggcattt cctccgccac tactgacgac   300
ctcgctacct acaaggatct caaccagggc aaccaggtca tcgtccccgg cggtatcaac   360
gaccctgtcg ctgttttcga cggctccgtc attccttccg cattaacgg cctccctacc    420 ctcctctaca cctccgtcag ctacctcccc attcactggt ccatccccta cacccgcggt   480
tccgagacgc agagcctggc tgtctccagc gatggtggct ccaactttac taagctcgac   540
cagggccccg ttattcctgg ccccccctt gcctacaacg tcaccgcctt ccgcgacccc    600
tacgtctttc agaaccccac cctcgactcc ctcctccact ccaagaacaa cacctggtac   660
accgtcattt cgggtggcct ccacggcaag ggccccgccc agtttcttta ccgtcagtac   720
gaccccgact ttcagtactg ggagttcctc ggccagtggt ggcacgagcc taccaactcc   780
acctggggca acggcacctg gccggccgc tgggccttca acttcgagac cggcaacgtc    840
ttttcgcttg acgagtacgg ctacaacccc cacggccaga tcttctccac cattggcacc   900
gagggctccg accagcccgt tgtccccag ctcacctcca tccacgatat gctttgggtc    960
tccggtaacg tttcgcgcaa cggatcggtt tccttcactc ccaacatggc cggcttcctc   1020
gactggggtt tctcgtccta cgccgccgcg ggtaaggttc ttccttccac gtcgctcccc   1080
tccaccaagt ccgtgccccc cgatcgcttc atttcgtacg tttggctctc cggcgaccte   1140 tttgagcagg ctgagggctt tcctaccaac cagcagaact ggaccggcac cctcctcctc   1200

```
ccccgtgagc tccgcgtcct ttacatcccc aacgtggttg ataacgccct tgcgcgcgag    1260
tccggcgctt cctggcaggt cgtctcctcc gatagctcgg ccggtactgt ggagctccag    1320
accctcggca tttccatcgc ccgcgagacc aaggccgccc tcctgtccgg cacctcgttc    1380
actgagtccg accgcactct taactcctcc ggcgtcgttc cctttaagcg ttccccctcc    1440
gagaagtttt tcgtcctctc cgcccagctc tccttccccg cctccgcccg cggctcgggc    1500
ctcaagtccg gcttccagat tctttcctcc gagctcgagt ccaccacggt ctactaccag    1560
tttagcaacg agtccatcat cgtcgaccgc agcaacacca gcgccgccgc ccgtactacc    1620
gacggtatcg actcctccgc cgaggccggc aagctccgcc tctttgacgt cctcaacggc    1680
ggcgagcagg ctattgagac cctcgacctt accctcgtcg ttgataactc cgtgctcgag    1740
atttacgcca acggtcgttt cgcgctttcc acctgggttc gctaa                    1785
```

POLYNUCLEOTIDE FOR IMPROVING PROTEIN PRODUCTION IN MICROORGANISMS OF THE PHYLUM LABYRINTHULOMYCOTA

CROSS-REFERENCE TO RELATED APPLICATION

This application claims the benefit of the filing date of U.S. Appl. No. 61/160,618, filed Mar. 16, 2009, and U.S. Appl. No. 61/290,441, filed Dec. 28, 2009, which are hereby incorporated by reference in their entireties.

REFERENCE TO A SEQUENCE LISTING SUBMITTED ELECTRONICALLY

The content of the electronically submitted sequence listing ("Sequence Listing.ascii.txt", 79,458 bytes, created on Mar. 10, 2010) filed with the application is incorporated herein by reference in its entirety.

BACKGROUND OF THE INVENTION

1. Field of the Invention

The present invention relates to recombinant cells and microorganisms of the phylum Labyrinthulomycota and their use in heterologous protein production. Novel promoter, terminator, and signal sequences for efficient production and, optionally, secretion of polypeptides from recombinant host cells and microorganisms are also encompassed by the present invention.

2. Background Art

Advancements in biotechnology and molecular biology have enabled the production of proteins in microbial, plant, and animal cells, many of which were previously available only by extraction from tissues, blood, or urine of humans and other animals. Biologics that are commercially available today are typically manufactured either in mammalian cells, such as Chinese Hamster Ovary (CHO) cells, or in microbial cells, such as yeast or *E. coli* cell lines.

Production of proteins via the fermentation of microorganisms presents several advantages over existing systems such as plant and animal cell culture. For example, microbial fermentation-based processes can offer: (i) rapid production of high concentration of protein; (ii) the ability to use sterile, well-controlled production conditions (such as Good Manufacturing Practice (GMP) conditions); (iii) the ability to use simple, chemically defined growth media allowing for simpler fermentations and fewer impurities; (iv) the absence of contaminating human or animal pathogens; and (v) the ease of recovering the protein (e.g., via isolation from the fermentation media). In addition, fermentation facilities are typically less costly to construct than cell culture facilities.

U.S. Publ. No. 2003/0166207 (now U.S. Pat. No. 7,001,772) was the first disclosure of recombinant constructs suitable for transforming thraustochytrids, including members of the genus *Schizochytrium*. This publication disclosed, among other things, *Schizochytrium* nucleic acid and amino acid sequences for an acetolactate synthase, an acetolactate synthase promoter and terminator region, an α-tubulin promoter, a promoter from a polyketide synthase (PKS) system, and a fatty acid desaturase promoter. U.S. Publ. Nos. 2006/0275904 and 2006/0286650, both herein incorporated by reference in their entireties, subsequently disclosed *Schizochytrium* sequences for actin, elongation factor 1 alpha (ef1α), and glyceraldehyde 3-phosphate dehydrogenase (gadph) promoters and terminators.

A continuing need exists for the identification of additional regulatory control elements for expression of proteins in thraustochytrid microorganisms, including regulatory control elements that are differentially expressed, for example, during different time points or under certain growth conditions, or in response to chemical or environmental stimuli. A need also exists for the identification of secretion signal sequences that can efficiently direct the secretion of a protein from a microorganism of the phylum Labyrinthulomycota and the order Thraustochytriales, such as *Schizochytrium* and other thraustochytrids.

BRIEF SUMMARY OF THE INVENTION

The present invention is directed to an isolated nucleic acid molecule comprising the polynucleotide sequence of SEQ ID NO:3.

The present invention is also directed to an isolated nucleic acid molecule comprising the polynucleotide sequence of SEQ ID NO:4.

The present invention is also directed to an isolated nucleic acid molecule comprising a polynucleotide sequence encoding a polypeptide, wherein the polypeptide comprises the amino acid sequence of SEQ ID NO: 1. In some embodiments, the polynucleotide sequence comprises SEQ ID NO:2.

The present invention is also directed to an isolated nucleic acid molecule comprising a polynucleotide sequence encoding a polypeptide, wherein the polypeptide comprises the amino acid sequence of SEQ ID NO:37. In some embodiments, the polynucleotide sequence comprises SEQ ID NO:38.

The present invention is also directed to an isolated nucleic acid molecule comprising the polynucleotide sequence of SEQ ID NO:42. In some embodiments, the polynucleotide sequence comprises SEQ ID NO:43.

The present invention is also directed to an isolated nucleic acid molecule comprising the polynucleotide sequence of SEQ ID NO:44. In some embodiments, the polynucleotide sequence comprises the polynucleotide sequence of SEQ ID NO:45.

The present invention is also directed to an isolated nucleic acid molecule comprising the polynucleotide sequence of SEQ ID NO:46.

The present invention is also directed to an isolated nucleic acid molecule comprising a polynucleotide sequence that is fully complementary to any of the polynucleotide sequences described above.

The present invention is also directed to a recombinant nucleic acid molecule comprising any of the isolated nucleic acid molecules described above. In some embodiments, the recombinant nucleic acid molecule is a vector.

In some embodiments, the isolated nucleic acid molecule is operably linked to a polynucleotide sequence encoding a protein. In some embodiments, the protein is operably linked to a secretion signal.

The present invention is also directed to a host cell comprising any of the isolated nucleic acid molecules or recombinant nucleic acid molecules described above, or combinations thereof. In some embodiments, the host cell is a member of the order Thraustochytriales. In some embodiments, the host cell is a *Schizochytrium* or a *Thraustochytrium*.

The present invention is also directed to a method for production of a protein, comprising culturing a recombinant microorganism of the order Thraustochytriales in a medium, wherein the recombinant microorganism comprises any of the isolated nucleic acid molecules described above operably linked to a polynucleotide sequence that encodes the protein, to produce the protein. In some embodiments, the protein is recovered from an isolated Thraustochytriales biomass. In some embodiments, the protein accumulates within the microorganism. In some embodiments, the protein accumulates within a membrane of the microorganism. In some embodiments, the protein is recovered from the culture medium. In some embodiments, the protein is secreted.

The present invention is also directed to an isolated polypeptide comprising the amino acid sequence of SEQ ID NO:1.

The present invention is also directed to an isolated polypeptide comprising the amino acid sequence of SEQ ID NO:15.

The present invention is also directed to a method of transforming a host cell, comprising: (a) pretreating the host cell with an enzyme having protease activity, and (b) introducing a nucleic acid molecule into the host cell by electroporation.

BRIEF DESCRIPTION OF THE DRAWINGS

FIG. 1 shows a *Schizochytrium* Na/Pi-IIIb2 transporter protein signal peptide amino acid sequence (SEQ ID NO:1).

FIG. 2 shows the polynucleotide sequence (SEQ ID NO:2) that encodes the signal peptide of SEQ ID NO:1.

FIG. 3 shows the *Schizochytrium* PUFA PKS OrfC promoter region polynucleotide sequence (SEQ ID NO:3).

FIG. 4 shows the *Schizochytrium* PUFA PKS OrfC terminator element-1 polynucleotide sequence (SEQ ID NO:4).

FIGS. 9A, 9C, and 9E are fluorescent micrographs. FIGS. 9B, 9D, and 9F are light micrographs. FIGS. 9A and 9B show the same field of cells transformed with pSchiz-sGr. FIGS. 9C and 9D show the same field of cells transformed with pSchiz-cG. FIGS. 9E and 9F show the same field of cells transformed with pSchiz-E.

FIG. 12 shows the first 30 amino acids of *Schizochytrium* Sec1 protein transporter protein. Amino acids 1 through 20 constitute the signal peptide sequence (SEQ ID NO:37).

FIG. 13 shows the polynucleotide sequence (SEQ ID NO:38) that encodes the signal peptide of SEQ ID NO:37.

FIG. 19 shows the *Schizochytrium* EF1 short promoter polynucleotide sequence (SEQ TD NO:42).

FIG. 20 shows the *Schizochytrium* EF1 long promoter polynucleotide sequence (SEQ ID NO:43).

FIG. 21 shows the *Schizochytrium* 60S short promoter polynucleotide sequence (SEQ ID NO:44).

FIG. 22 shows the *Schizochytrium* 60S long promoter polynucleotide sequence (SEQ ID NO:45).

FIG. 23 shows the *Schizochytrium* Sec1 promoter polynucleotide sequence (SEQ ID NO:46).

FIG. 40A shows N-glycan structures detected on *Schizochytrium* secreted proteins as determined by NSI-Total Ion Mapping of permethylated N-glycans.

FIG. 41A and FIG. 41B show predicted signal sequences native to *Schizochytrium* based on use of the SignalP algorithm. See, e.g., Bendsten et al., *J, Mol. Biol.* 340: 783-795 (2004); Nielsen and Krogh, *Proc. Int. Conf. Intell. Syst. Mol. Biol.* 6:122-130 (1998); Nielsen et al., *Protein Engineering* 12:3-9 (1999); Emanuelsson et al., *Nature Protocols* 2:953-971 (2007).

FIG. 42 shows a codon usage table for *Schizochytrium*.

FIG. 44 shows a codon-optimized nucleic acid sequence (SEQ ID NO:75) encoding the Sec1 signal peptide from *Schizochytrium* fused to the mature Suc1 invertase from *Aspergillus niger* (GenBank Accession No. S33920).

DETAILED DESCRIPTION OF THE INVENTION

Figure 5:
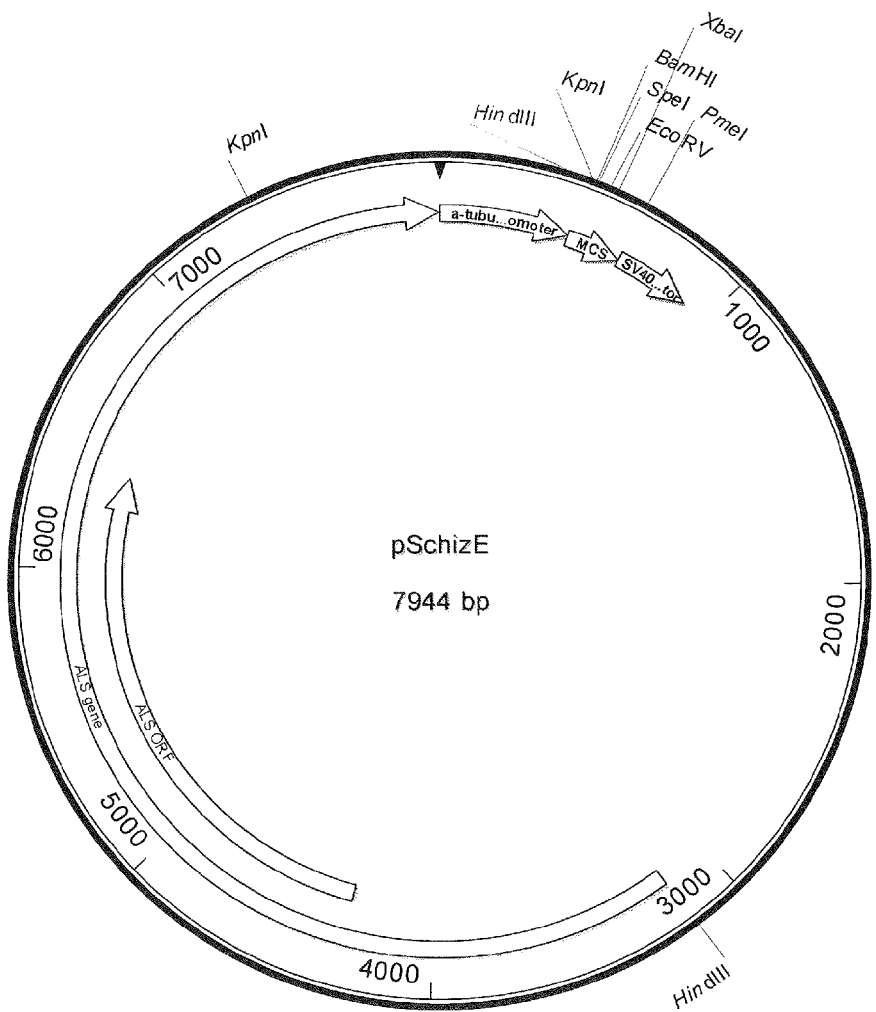
FIG. 5 shows a plasmid map of pSchizE.

Members of the phylum Labyrinthulomycota, such as *Schizochytrium*, *Thraustochytrium*, and other thraustochytrids, are eukaryotes that are capable of processing polypeptides through a conventional secretory pathway. It has been recognized that these microorganisms also produce fewer abundantly-secreted proteins than CHO cells, resulting in an advantage of using *Schizochytrium* over CHO cells. In addition, unlike *E. coli*, members of the phylum Labyrinthulomycota, such as *Schizochytrium*, perform protein glycosylation, such as N-linked glycosylation, which is required for the biological activity of certain proteins. It has been determined that the N-linked glycosylation exhibited by thraustochytrids such as *Schizochytrium* more closely resembles mammalian glycosylation patterns than does yeast glycosylation.

Efficient production of recombinant proteins also includes: (i) methods for transforming a selected host cell, (ii) selection markers for selecting transformants, and (iii) expression cassettes comprising regulatory elements that function in the particular host cell. Such regulatory elements include promoter and terminator sequences that are important for controlling expression of a polynucleotide sequence. According to the present invention, the terms regulatory elements, regulatory control elements, and regulatory sequences can be used interchangeably and include, but are not limited to, sequences and/or molecules that are promoters, enhancers, transcription terminators, signal sequences, ribosomal binding sites, repressor binding sites, stem-loops, and intron splice sites. Signal peptides (also known as signal sequences, secretion signal peptides, or leader sequences) that direct the secretion of a protein can also be utilized if protein secretion into the culture medium is desired.

Host Cells

The present invention is directed to production of protein in a host cell that is a microorganism of the phylum Labyrinthulomycota. In some embodiments, the host cell of the phylum Labyrinthulomycota is used as a biofactory for protein production.

In some embodiments, the recombinant host cell of the phylum Labyrinthulomycota is a thraustochytrid, such as a *Schizochytrium* or *Thraustochytrium*. According to the present invention, the term "thraustochytrid" refers to any member of the order Thraustochytriales, which includes the family Thraustochytriaceae, and the term "labyrinthulid" refers to any member of the order Labyrinthulales, which includes the family Labyrinthulaceae. Members of the family Labyrinthulaceae were previously considered to be members of the order Thraustochytriales, but in more recent revisions of the taxonomic classification of such organisms, the family Labyrinthulaceae is now considered to be a member of the order Labyrinthulales. Both Labyrinthulales and Thraustochytriales are considered to be members of the phylum Labyrinthulomycota. Taxonomic theorists now generally place both of these groups of microorganisms with the algae or algae-like protists of the Stramenopile lineage. The current taxonomic placement of the thraustochytrids and labyrinthulids can be summarized as follows:

Realm: Stramenopila (Chromista)
Phylum: Labyrinthulomycota (Heterokonta)
Class: Labyrinthulomycetes (Labyrinthulae)
Order: Labyrinthulales
Family: Labyrinthulaceae
Order: Thraustochytriales
Family: Thraustochytriaceae For purposes of the present invention, strains described as thraustochytrids include the following organisms: Order: Thraustochytriales; Family: Thraustochytriaceae; Genera: *Thraustochytrium* (Species: sp., *arudimentale, aureum, benthicola, globosurn, kinnei, rnotivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporum*), *Japonochytrium* (Species: sp., *marinum*), *Aplanochytrium* (Species: sp., *haliotidis, kerguelensis, profunda, stocchinoi*), *Althornia* (Species: sp., *crouchii*), or *Elina* (Species: sp., *marisalba, sinorifica*). For the purposes of this invention, species described within *Ulkenia* will be considered to be members of the genus *Thraustochytrium*. *Aurantiacochytrium* and *Oblogospora* are two additional genuses encompassed by the phylum Labyrinthulomycota in the present invention.

Strains described in the present invention as Labyrinthulids include the following organisms: Order: Labyrinthulales, Family: Labyrinthulaceae, Genera: *Labyrinthula* (Species: sp., *algeriensis, coenocystis, chattonii, macrocystis, macrocystis atlantica, macrocystis macro cystis, marina, minuta, roscoffensis, valkanovii, vitellina, vitellina pacifica, vitellina vitellina, zopfii*), *Labyrinthuloides* (Species: sp., *haliotidis, yorkensis*), *Labyrinthomyxa* (Species: sp., *marina*), *Diplophrys* (Species: sp., *archeri*), *Pyrrhosorus* (Species: sp., *marinus*), *Sorodiplophrys* (Species: sp., *stercorea*) or *Chlamydomyxa* (Species: sp., *labyrinthuloides, montana*) (although there is currently not a consensus on the exact taxonomic placement of *Pyrrhosorus, Sorodiplophrys* or *Chlamydomyxa*).

Host cells of the phylum Labyrinthulomycota include, but are not limited to, deposited strains PTA-10212, PTA-10213, PTA-10214, PTA-10215, PTA-9695, PTA-9696, PTA-9697, PTA-9698, PTA-10208, PTA-10209, PTA-10210, PTA-10211, the microorganism deposited as SAM2179 (named "*Ulkenia* SAM2179" by the depositor), any *Thraustochytrium* species (including former *Ulkenia* species such as *U. visurgensis, U. amoeboida, U. sarkariana, U. profunda, U radiata, U. minuta* and *Ulkenia* sp. BP-5601), and including *Thraustochytrium striatum, Thraustochytrium aureum, Thraustochytrium roseum*; and any *Japonochytrium* species. Strains of Thraustochytriales include, but are not limited to *Thraustochytrium* sp. (23B) (ATCC 20891); *Thraustochytrium striatum* (Schneider)(ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207). *Schizochytrium* include, but are not limited to *Schizochytrium aggregatum, Schizochytrium limacinum, Schizochytrium* sp. (S31) (ATCC 20888), *Schizochytrium* sp. (S8) (ATCC 20889), *Schizochytrium* sp. (LC-RM) (ATCC 18915), *Schizochytrium* sp. (SR 21), deposited strain ATCC 28209 and deposited *Schizochytrium limacinum* strain IFO 32693. In some embodiments, the host cell is a *Schizochytrium* or a *Thraustochytrium*. *Schizochytrium* can replicate both by successive bipartition and by forming sporangia, which ultimately release zoospores. *Thraustochytrium*, however, replicate only by forming sporangia, which then release zoospores. In some embodiments, the host cell of the invention is a recombinant host cell.

Effective culture conditions for a host cell of the invention include, but are not limited to, effective media, bioreactor, temperature, pH, and oxygen conditions that permit protein production and/or recombination. An effective medium refers to any medium in which a Thraustochytriales cell, e.g., a *Schizochytrium* host cell, is typically cultured. Such medium typically comprises an aqueous medium having assimilable carbon, nitrogen, and phosphate sources, as well as appropriate salts, minerals, metals, and other nutrients, such as vitamins. Non-limiting examples of suitable media and culture conditions are disclosed in the Examples section. Non-limiting culture conditions suitable for Thraustochytriales microorganisms are also described in U.S. Pat. No. 5,340,742, incorporated herein by reference in its entirety. Cells of the present invention can be cultured in conventional fermentation bioreactors, shake flasks, test tubes, microtiter dishes, and petri plates. Culturing can be carried out at a temperature, pH, and oxygen content appropriate for a recombinant cell. In some embodiments, a Labyrinthulomycota host cell of the invention contains a recombinant vector comprising a nucleic acid sequence encoding a selection marker. In some embodiments, the selection marker allows for the selection of transformed microorganisms. Examples of dominant selection markers include enzymes that degrade compounds with antibiotic or fungicide activity such as, for example, the Sh ble gene from *Steptoalloteichus hindustanus*, which encodes a "bleomycin-binding protein" represented by SEQ ID NO:5. In some embodiments, the nucleic acid sequence encoding a dominant selection marker comprises a thraustochytrid acetolactate synthase sequence such as a mutated version of the polynucleotide sequence of SEQ ID NO:6. In some embodiments, the acetolactate synthase has been modified, mutated, or otherwise selected to be resistant to inhibition by sulfonylurea compounds, imidazolinone-class inhibitors, and/or pyrimidinyl oxybenzoates. In some embodiments, the acetolactate synthase is a homologue of a naturally occurring acetolactate synthase. In some embodiments, a thraustochytrid microorganism that has been transfected with a recombinant vector comprising the acetolactate synthase has a reduced sensitivity to sulfonurea compounds, imidazolinone-class inhibitors, and/or pyrimidinyl oxybezoates. In some embodiments, the recombinant vector comprises a nucleic acid sequence encoding an acetolactate synthase protein comprising an amino acid sequence that differs from SEQ ID NO:7 by an amino acid deletion, insertion, or substitution at one or more of the following positions: 116G, 117A, 192P, 200A, 251K, 358M, 383D, 592V, 595W, or 599F. In some embodiments, a mutated acetolactate synthase protein has an amino acid sequence selected from the group consisting of: SEQ ID NO:8, SEQ ID NO:9, and SEQ ID NO:10. In some embodiments, the recombinant vector comprises a polynucleotide sequence at least about 70%, at least about 75%, at least about 80%, at least about 85%, at least about 90%, at least about 95%, at least about 96%, at least about 97%, at least about 98%, or at least about 99% identical to SEQ ID NO:7, SEQ ID NO:8, SEQ ID NO:9, or SEQ ID NO:10, wherein said polynucleotide sequence encodes an amino acid sequence that functions as a dominant selection marker, at least in a thraustochytrid. In some embodiments, the recombinant vector comprises a polynucleotide sequence encoding a functional fragment of SEQ ID NO:7, which functions as a dominant selection marker, at least in a thraustochytrid. In some embodiments, the recombinant vector comprises a polynucleotide sequence selected from the group consisting of: SEQ ID NO:11, SEQ ID NO:12, and SEQ ID NO:13.

According to the present invention, the term "transformation" is used to refer to any method by which an exogenous nucleic acid molecule (i.e., a recombinant nucleic acid molecule) can be inserted into microbial cells. In microbial systems, the term "transformation" is used to describe an inherited change due to the acquisition of exogenous nucleic acids by the microorganism and is essentially synonymous with the term "transfection." Suitable transformation techniques for introducing exogenous nucleic acid molecules into the Labyrinthulomycota host cells include, but are not limited to, particle bombardment, electroporation, microinjection, lipofection, adsorption, infection, and protoplast fusion. In some embodiments, exogenous nucleic acid molecules, including recombinant vectors, are introduced into a microbial cell that is in a stationary phase. In some embodiments, exogenous nucleic acid molecules, including recombinant vectors, are introduced into a microbial cell during the exponential growth phase. In some embodiments, exogenous nucleic acid molecules, including recombinant vectors, are introduced into cells when they reach an optical density of 1.5 to 2 at 600 nm.

The present invention is also directed to a method of transforming a host cell, comprising: (a) pretreating the host cell with an enzyme having protease activity, and (b) introducing a nucleic acid molecule into the host cell by electroporation. In some embodiments, the host cell is transformed with higher efficiency following enzyme pretreatment prior to electroporation than without enzyme pretreatment. The enzyme includes, but is not limited to, an enzymatic activity associated with snail acetone powder, protease IX, protease XIV, sulfatase, β-glucuronidase, and combinations thereof. In some embodiments, the host cell is pretreated with about 0.05 mg/ml, about 0.1 mg/ml, about 0.15 mg/ml, about 0.2 mg/ml, about 0.25 mg/ml, about 0.3 mg/ml, about 0.4 mg/ml, about 0.5 mg/ml, about 0.6 mg/ml, 0.7 mg/ml, 0.8 mg/ml, 0.9 mg/ml, or about 1 mg/ml of snail acetone powder, protease IX, protease XIV, or combinations thereof. In some embodiments, the host cell is treated with about 0.05 mg/ml to about 1 mg/ml, about 0.1 mg/ml to about 1 mg/ml, about 0.1 mg/ml to about 0.5 mg/ml, or about 0.05 mg/ml to about 0.5 mg/ml of snail acetone powder, protease IX, protease XIV, or a combination thereof. In some embodiments, the host cell is treated with 0.05×, 0.1×, 0.2×, 0.3×, 0.4×, 0.5×, 0.6×, 0.7×, 0.8×, 0.9×, or 1× of sulfatase, β-Glucuronidase, or a combination thereof. In some embodiments, the host cell is treated with about 0.05× to about 1×, about 0.1× to about 1×, about 0.1× to about 0.5×, or about 0.05× to about 0.5× of sulfatase, β-Glucuronidase, or a combination thereof. In some embodiments, protease pretreatment comprises pretreatment with protease IX, protease XIV, snail acetone powder, sulfatase, β-Glucuronidase, or a combination thereof at any of the above-described concentrations. In some embodiments, electroporation occurs at a voltage of about 100 V to about 500 V for a 0.1 cm or a 0.2 cm cuvette gap distance. In some embodiments, electroporation occurs at a voltage of about 100 V, 150 V, 200 V, 250 V, 300 V, 350 V, 400 V, 450 V, or 500 V for a 0.1 cm or a 0.2 cm cuvette gap distance.

In some embodiments of the invention, a host cell is genetically modified to introduce or delete genes involved in biosynthetic pathways associated with the transport and/or synthesis of carbohydrates, including those involved in glycosylation. For example, the host cell can be modified by deleting endogenous glycosylation genes and/or inserting human or animal glycosylation genes to allow for glycosylation patterns that more closely resemble those of humans. Modification of glycosylation in yeast can be found, for example, in U.S. Pat. No. 7,029,872 and U.S. Publ. Nos. 2004/0171826, 2004/0230042, 2006/0257399, 2006/0029604, and 2006/0040353. A host cell of the present invention also includes a cell in which an RNA viral element is employed to increase or regulate gene expression.

Expression Systems

In some embodiments, the expression system of the invention used for expression of a protein in a host cell comprises regulatory control elements that are active in algal cells. In some embodiments, the expression system of the invention comprises regulatory control elements that are active in Labyrinthulomycota cells. In some embodiments, the expression system of the invention comprises regulatory control elements that are active in thraustochytrids. In some embodiments, the expression system of the invention comprises regulatory control elements that are active in *Schizochytrium* or *Thraustochytrium*. Many algal regulatory control elements, including various promoters, are active in a number of diverse species. Therefore, the novel regulatory sequences disclosed as aspects of the invention can be utilized in a cell type that is identical to the cell from which they were isolated or can be utilized in a cell type that is different than the cell from which they were isolated. The design and construction of such expression cassettes use standard molecular biology techniques known to persons skilled in the art. See, for example, Sambrook et al., 2001, Molecular Cloning: A Laboratory Manual, 3$^{rd}$ edition.

In some embodiments, the expression system used for protein production in Labyrinthulomycota cells comprises regulatory elements that are derived from Labyrinthulomycota sequences. In some embodiments, the expression system used to produce proteins in Labyrinthulomycota cells comprises regulatory elements that are derived from non-Labyrinthulomycota sequences, including sequences derived from non-Labyrinthulomycota algal sequences. In some embodiments, the expression system of the invention comprises a polynucleotide sequence encoding a protein, wherein the polynucleotide sequence is associated with any promoter sequence, any terminator sequence, and/or any other regulatory sequences that are functional in a Labyrinthulomycota host cell. Inducible or constitutively active sequences can be used. Suitable regulatory control elements also include any of the regulatory control elements associated with the nucleic acid molecules described herein.

The present invention is also directed to an expression cassette for expression of a protein in a host cell. The present invention is also directed to any of the above-described host cells comprising an expression cassette for expression of a protein in the host cell. In some embodiments, the expression system comprises an expression cassette containing genetic elements, such as at least a promoter, a coding sequence, and a terminator region operably linked in such a way that they are functional in a host cell. In some embodiments, the expression cassette comprises at least one of the isolated nucleic acid molecules of the invention as described herein. In some embodiments, all of the genetic elements of the expression cassette are sequences associated with isolated nucleic acid molecules. In some embodiments, the control sequences are inducible sequences. In some embodiments, the nucleic acid sequence encoding the protein is integrated into the genome of the host cell. In some embodiments, the nucleic acid sequence encoding the protein is stably integrated into the genome of the host cell.

In some embodiments, an isolated nucleic acid sequence encoding a protein to be expressed is operably linked to a promoter sequence and/or a terminator sequence, both of which are functional in the host cell. The promoter and/or terminator sequence to which the isolated nucleic acid sequence encoding a protein to be expressed is operably linked can include any promoter and/or terminator sequence, including but not limited to the novel nucleic acid sequences of the present invention, the regulatory sequences disclosed in issued U.S. Pat. No. 7,001,772, the regulatory sequences disclosed in U.S. Publ. Nos. 2006/0275904 and 2006/0286650, or other regulatory sequences functional in the host cell in which they are transformed that are operably linked to the isolated polynucleotide sequence encoding a protein. In some embodiments, the nucleic acid sequence encoding the protein is codon-optimized for the specific Labyrinthulomycota host cell to maximize translation efficiency.

The present invention is also directed to recombinant vectors comprising an expression cassette of the present invention. Recombinant vectors include, but are not limited to, plasmids, phages, and viruses. In some embodiments, the recombinant vector is a linearized vector. In some embodiments, the recombinant vector is an expression vector. As used herein, the phrase "expression vector" refers to a vector that is suitable for production of an encoded product (e.g., a protein of interest). In some embodiments, a nucleic acid sequence encoding the product to be produced is inserted into the recombinant vector to produce a recombinant nucleic acid molecule. The nucleic acid sequence encoding the protein to be produced is inserted into the vector in a manner that operatively links the nucleic acid sequence to regulatory sequences in the vector (e.g., a Thraustochytriales promoter), which enables the transcription and translation of the nucleic acid sequence within the recombinant microorganism. In some embodiments, a selectable marker, including any of the selectable markers described herein, enables the selection of a recombinant microorganism into which a recombinant nucleic acid molecule of the present invention has successfully been introduced.

In some embodiments, proteins produced by a recombinant host cell of the invention include, but are not limited to, therapeutic proteins. A "therapeutic protein" as used herein includes proteins that are useful for the treatment or prevention of diseases, conditions, or disorders in animals and humans. The teens "treat" and "treatment" refer to both therapeutic treatment and prophylactic or preventative measures, wherein the object is to prevent or slow down (lessen) an undesired physiological condition, disease, or disorder, or to obtain beneficial or desired clinical results. For purposes of this invention, beneficial or desired clinical results include, but are not limited to, alleviation of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a clinically significant response without excessive side effects. Treatment also includes prolonging survival as compared to expected survival if not receiving treatment.

In certain embodiments, therapeutic proteins include, but are not limited to, biologically active proteins, e.g., enzymes, antibodies, or antigenic proteins. In certain embodiments, therapeutic proteins include, but are not be limited to: protein A, human growth hormone, an interferon, aprotinin, human alpha antitrypsin, lipophilic proteins, human serum albumin, glutamic acid decarboxylase, gastric lipases, lactoferrin/lysozyme, invertase, antibodies (including, but not limited to, VEGF monoclonal antibody (AVASTIN®) and HER2 monoclonal antibody (HERCEPTIN®)), a human vaccine, an animal vaccine, and an animal therapeutic.

In some embodiments, proteins produced by a recombinant host cell of the invention include, but are not limited to industrial enzymes. Industrial enzymes include, but are not limited to, enzymes that are used in the manufacture, preparation, preservation, nutrient mobilization, or processing of products, including food, medical, chemical, mechanical, and other industrial products. Industrial enzymes include, but are not limited to: alpha amylase, alpha-galactosidase, beta-amylase, cellulose, beta-glucanase, dextranase, dextrinase, glucoamylase, hemmicellulase/pentosanase, xylanase, invertase, lactase, naringinase, pectinase, pullulanase, acid proteinase, alkaline protease, bromelain, papain, pepsin, aminopeptidase, endo-peptidases (trypsin, chemotrypsin, pepsin, elastase), rennet/rennin/chymosin, subtilism, thermolysin, aminoacylase, glutaminase, lysozyme, penicillin acylase, triglyceridases, phospholipases, pregastric esterases, phytase, amidases, isomerases, alcohol dehydrogenase, amino acid oxidase, catalase, chloroperoxidase, peroxidase, acetolactate decarboxylase, aspartic beta-decarboxylase, histidase, cyclodextrin glycosyltransferase, fromase, phytase, and chymosin.

In some embodiments, proteins produced by a recombinant host cell of the invention include an auxotrophic marker, a dominant selection marker (such as, for example, an enzyme that degrades antibiotic activity) or another protein involved in transformation selection, a protein that functions as a reporter, an enzyme involved in protein glycosylation, and an enzyme involved in cell metabolism.

In any of the embodiments of the invention, a protein produced by a host cell of the invention can be an "output protein" or a "heterologous output protein." An "output protein" or "heterologous output protein" as used herein refers to a heterologous recombinant protein that is not involved in modifying the metabolism of the host cell producing the protein and that is produced by the host cell for subsequent isolation. "Output protein" as defined herein does not include proteins encoded by reporter genes.

Heterologous output proteins produced by a recombinant host cell of the invention do not include selectable markers such as a Zeocin resistance gene (e.g., the ble gene from *Steptoalloteichus hindustanus*) and *E. coli* Neomycin phosphotransferase (npt), and transposon Tn5, blasticidin deaminase (bsdR) from *Aspergillus terreus*, PUFA synthase ORFA from *Thraustochytrium* T23B, PUFA synthase ORFB from *Thraustochytrium* T23B, PUFA synthase ORFC from *Thraustochytrium* T23B, synthetic eGFP derived from *Aequorea victoria*, native genes encoding proteins associated with the synthesis of a fatty acid selected from the group consisting of docosahexaenoic acid (DHA), docosapentaenoic acid (DPA), eicosapentaenoic acid (EPA) and arachidonic acid (ARA), a fatty acid synthase, a fatty acid desaturase, a fatty acid elongase, a protein associated with a polyketide synthase complex and a protein associated with incorporation of fatty acids into phospholipids or into triacylglycerol molecules, an omega-3 fatty acid desaturase, a polyenoic fatty acid isomerase, HMG-CoA synthase, HMG-CoA reductase, squalene synthase, phytoene synthase, phytoene desaturase, a carotenoid cyclase, a carotenoid hydroxylase, a carotenoid ketolase, vitamin E and lipoic acid, proteins associated with the isoprenoid biosynthetic pathway, and enzymes involved in host cell production of polyunsaturated fatty acids or carotenoids.

In some embodiments, a protein produced by a host cell of the invention is produced at commercial scale. Commercial scale includes production of protein from a microorganism grown in an aerated fermentor of a size ≥100 L, ≥1,000 L, ≥10,000 L or ≥100,000 L. In some embodiments, the commercial scale production is done in an aerated fermentor with agitation.

In some embodiments, a protein produced by a host cell of the invention can accumulate within the cell or can be secreted from the cell, e.g., into the culture medium as a soluble protein.

In some embodiments, a protein produced by the invention is recovered from the cell, from the culture medium, or fermentation medium in which the cell is grown. In some embodiments, the protein is a secreted protein that is recovered from the culture media as a soluble protein. In some embodiments, the protein is a secreted protein comprising a signal peptide.

In some embodiments, a protein produced by the invention comprises a targeting signal directing its retention in the endoplasmic reticulum, directing its extracellular secretion, or directing it to other organelles or cellular compartments. In some embodiments, the protein comprises a signal peptide. In some embodiments, the protein comprises a Na/Pi-IIb2 transporter signal peptide or Sec1 transport protein. In some embodiments, the signal peptide comprises the amino acid sequence of SEQ ID NO:1 or SEQ ID NO:37. In some embodiments, the protein comprising a signal peptide having the amino acid sequence of SEQ ID NO:1 or SEQ ID NO:37 is secreted into the culture medium. In some embodiments, the signal peptide is cleaved from the protein during the secretory process, resulting in a mature form of the protein.

In some embodiments, a protein produced by a host cell of the invention is glycosylated. In some embodiments, the glycosylation pattern of the protein produced by the invention more closely resembles mammalian glycosylation patterns than proteins produced in yeast or *E. coli*. In some embodiments, the protein produced by a Labyrinthulomycota host cell of the invention comprises a N-linked glycosylation pattern. Glycosylated proteins used for therapeutic purposes are less likely to promote anti-glycoform immune responses when their glycosylation patterns are similar to glycosylation patterns found in a subject organism. Conversely, glycosylated proteins having linkages or sugars that are not characteristic of a subject organism are more likely to be antigenic. Effector functions can also be modulated by specific glycoforms. For example, IgG can mediate pro- or anti-inflammatory reactions in correlation with the absence or presence, respectively, of terminal sialic acids on Fc region glycoforms (Kaneko et al, *Science* 313(5787):670-3 (2006)).

The present invention is further directed to a method of producing a recombinant protein, the method comprising culturing a recombinant Labyrinthulomycota host cell of the invention under conditions sufficient to express a polynucleotide sequence encoding the protein. In some embodiments, the recombinant protein is secreted from the host cell and is recovered from the culture medium. In some embodiments, a protein that is secreted from the cell comprises a secretion signal peptide. Depending on the vector and host system used for production, recombinant proteins of the present invention can remain within the recombinant cell, can be secreted into the fermentation medium, can be secreted into a space between two cellular membranes, or can be retained on the outer surface of a cell membrane. As used herein, the phrase "recovering the protein" refers to collecting fermentation medium containing the protein and need not imply additional steps of separation or purification. Proteins produced by the method of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing, and differential solubilization. In some embodiments, proteins produced by the method of the present invention are isolated in "substantially pure" form. As used herein, "substantially pure" refers to a purity that allows for the effective use of the protein as a commercial product. In some embodiments, the recombinant protein accumulates within the cell and is recovered from the cell. In some embodiments, the host cell of the method is a thraustochytrid. In some embodiments, the host cell of the method is a *Schizochytrium* or a *Thraustochytrium*. In some embodiments, the recombinant protein is a therapeutic protein, a food enzyme, or an industrial enzyme. In some embodiments, the recombinant Labyrinthulomycota host cell is a *Schizochytrium* and the recombinant protein is a therapeutic protein that comprises a secretion signal sequence.

In some embodiments, a recombinant vector of the invention is a targeting vector. As used herein, the phrase "targeting vector" refers to a vector that is used to deliver a particular nucleic acid molecule into a recombinant cell, wherein the nucleic acid molecule is used to delete or inactivate an endogenous gene within the host cell (i.e., used for targeted gene disruption or knock-out technology). Such a vector is also known as a "knock-out" vector. In some embodiments, a portion of the targeting vector has a nucleic acid sequence that is homologous to a nucleic acid sequence of a target gene in the host cell (i.e., a gene which is targeted to be deleted or inactivated). In some embodiments, the nucleic acid molecule inserted into the vector (i.e., the insert) is homologous to the target gene. In some embodiments, the nucleic acid sequence of the vector insert is designed to bind to the target gene such that the target gene and the insert undergo homologous recombination, whereby the endogenous target gene is deleted, inactivated, or attenuated (i.e., by at least a portion of the endogenous target gene being mutated or deleted).

Isolated Nucleic Acid Molecules

The present invention is also directed to isolated nucleic acid molecules or polynucleotide sequences that can be used to regulate gene expression and/or direct protein secretion in recombinant host cells. The nucleic acid sequences described herein include promoters, termination sequences, and nucleic acid sequences encoding signal peptides, and can be utilized to regulate the transcription and/or secretion of homologous or heterologous proteins.

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrases "nucleic acid sequence" or "polynucleotide sequence" primarily refers to the sequence of nucleotides on the nucleic acid molecule, the phrases are used interchangeably, especially with respect to a nucleic acid molecule, polynucleotide sequence, or a nucleic acid sequence that is capable of encoding a protein. In some embodiments, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on sequence, function, and/or the biological activity of the encoded peptide or protein.

A nucleic acid sequence complement of a promoter sequence, terminator sequence, signal peptide sequence, or any other sequence of the invention refers to the nucleic acid sequence of the nucleic acid strand that is complementary to the strand with the promoter sequence, terminator sequence, signal peptide sequence, or any other sequence of the invention. It will be appreciated that a double-stranded DNA that contains a sequence of the invention comprises a single-strand DNA and its complementary strand having a sequence that is a complement to the single-strand DNA. As such, nucleic acid molecules of the present invention can be either double-stranded or single-stranded, and include those nucleic acid molecules that form stable hybrids under "stringent" hybridization conditions with a sequence of the invention, and/or with a complement of a sequence of the invention. Methods to deduce a complementary sequence are known to those skilled in the art.

The term "protein" includes single-chain polypeptide molecules as well as multiple-polypeptide complexes where individual constituent polypeptides are linked by covalent or non-covalent means. The team "polypeptide" includes peptides of two or more amino acids in length, typically having more than 5, 10, or 20 amino acids.

The novel nucleic acid molecules of the present invention can be utilized in any microorganism in which they are functional. In some embodiments, the nucleic acid molecules are utilized in recombinant microorganisms of the phylum Labyrinthulomycota. In some embodiments, the recombinant nucleic acid molecules are utilized in recombinant microorganisms of the order Thraustochytriales. In some embodiments, the recombinant nucleic acid molecules are utilized in *Schizochytrium* or *Thraustochytrium* microorganisms. As used herein, a recombinant microorganism has a genome which is modified (i.e., mutated or changed) from its normal (i.e., wild-type or naturally occurring) form using recombinant technology. A recombinant microorganism according to the present invention can include a microorganism in which nucleic acid molecules have been inserted, deleted, or modified (i.e., mutated, e.g., by insertion, deletion, substitution, and/or inversion of nucleotides), in such a manner that such modification or modifications provide the desired effect within the microorganism. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist in the recombinant microorganism, and therefore the protein does not exist in the recombinant microorganism), a mutation in the gene which results in incomplete or no translation of the protein (e.g., the protein is not expressed), or a mutation in the gene which decreases or abolishes the natural function of the protein (e.g., a protein is expressed which has decreased or no activity (for example, enzymatic activity or action). Genetic modifications which result in an increase in gene expression or function can be referred to as amplification, overproduction, overexpression, activation, enhancement, addition, or up-regulation of a gene.

Promoters

The present invention is also directed to novel regulatory control elements that are promoters. A promoter of the invention is a region of DNA that directs transcription of an associated coding region.

In some embodiments, the promoter is from a microorganism of the phylum Labyrinthulomycota. In some embodiments, the promoter is from a thraustochytrid including, but not limited to: the microorganism deposited as SAM2179 (named "*Ulkenia* SAM2179" by the depositor), a microorganism of the genus *Ulkenia* or *Thraustochytrium*, or a *Schizochytrium*. *Schizochytrium* include, but are not limited to, *Schizochytrium aggregatum, Schizochytrium limacinum, Schizochytrium* sp. (S31) (ATCC 20888), *Schizochytrium* sp. (S8) (ATCC 20889), *Schizochytrium* sp. (LC-RM) (ATCC 18915), *Schizochytrium* sp. (SR 21), deposited *Schizochytrium* strain ATCC 28209, and deposited *Schizochytrium* strain IFO 32693.

A promoter of the invention can have promoter activity at least in a thraustochytrid, and includes full-length promoter sequences and functional fragments thereof, fusion sequences, and homologues of a naturally occurring promoter. Restriction enzymes can be used to digest the nucleic acid molecules of the invention, followed by the appropriate assay to determine the minimal sequence required for promoter activity. Such fragments themselves individually represent embodiments of the present invention. A homologue of a promoter differs from a naturally occurring promoter in that at least one, two, three, or several, nucleotides have been deleted, inserted, inverted, substituted and/or derivatized. A homologue of a promoter can retain activity as a promoter, at least in a thraustochytrid, although the activity can be increased, decreased, or made dependant upon certain stimuli. The promoters of the invention can comprise one or more sequence elements that confer developmental and tissue-specific regulatory control or expression.

In some embodiments, an isolated nucleic acid molecule of the invention comprises a PUFA PKS OrfC promoter ("PKS OrfC promoter"). A PKS OrfC promoter of the invention is a region of DNA that is naturally located upstream (towards the 5' region) of the OrfC coding region and that directs OrfC transcription. In some embodiments, the PKS OrfC promoter has a polynucleotide sequence represented by SEQ ID NO:3. In some embodiments, an isolated nucleic acid molecule of the invention comprises a polynucleotide sequence that is at least about 65%, at least about 70%, at least about 75%, at least about 80%, at least about 85%, at least about 90%, at least about 95%, at least about 96%, at least about 97%, at least about 98%, or at least about 99% identical to SEQ ID NO:3, wherein the polynucleotide sequence has promoter activity (i.e., has basal promoter transcriptional activity, at least for a PUFA PKS OrfC sequence), at least in a thraustochytrid. The homology (or % identity) can be found over a sequence of at least 10, at least 20, at least 30, at least 40, at least 50, at least 100, at least 200, at least 300, at least 400, at least 500, at least 1000, at least 1500 nucleotides, or over the entire sequence.

The present invention is also directed to an isolated nucleic acid molecule comprising a polynucleotide sequences that hybridizes to SEQ ID NO:3 or that hybridizes to a polynucleotide sequence that is at least 95% identical to SEQ ID NO:3. In some embodiments, the isolated nucleic acid molecule comprises a polynucleotide sequence that is fully complementary to SEQ ID NO:3 or to a polynucleotide sequence that is at least 95% identical to SEQ ID NO:3. In some embodiments, a PKS OrfC promoter of the present invention includes a PKS OrfC promoter homologue that is sufficiently similar to a naturally occurring PKS OrfC promoter sequence that the nucleic acid sequence of the homologue is capable of hybridizing under moderate, high, or very high stringency conditions (described below) to the complement of the nucleic acid sequence of the naturally occurring PKS OrfC promoter. In some embodiments, a PUFA PKS OrfC promoter sequence of the invention hybridizes under moderate, high or very high stringency conditions to the complement of SEQ ID NO:3.

In some embodiments, the promoter of the invention comprises the OrfC promoter of pCL0001 as deposited in ATCC Accession No. PTA-9615.

In some embodiments, an isolated nucleic acid molecule of the invention comprises an EF1 short promoter ("EF1 short" or "EF1-S" promoter) or EF1 long promoter ("EF1 long" or "EF1-L" promoter). An EF1 short or long promoter of the invention is a region of DNA that is naturally located upstream (towards the 5' region) of the EF1 coding region and that directs EF1 transcription. In some embodiments, the EF1 short promoter has a polynucleotide sequence represented by SEQ ID NO:42. In some embodiments, the EF1 long promoter has a polynucleotide sequence represented by SEQ ID NO:43. In some embodiments, an isolated nucleic acid molecule of the invention comprises a polynucleotide sequence that is at least about 65%, at least about 70%, at least about 75%, at least about 80%, at least about 85%, at least about 90%, at least about 95%, at least about 96%, at least about 97%, at least about 98%, or at least about 99% identical to SEQ ID NO:42 or SEQ ID NO:43, wherein the polynucleotide sequence has promoter activity (i.e., has basal promoter transcriptional activity, at least for an EF1 short or long promoter sequence, respectively), at least in a thraustochytrid. The homology (or % identity) can be found over a sequence of at least 10, at least 20, at least 30, at least 40, at least 50, at least 100, at least 200, at least 300, at least 400, or at least 500 nucleotides, or over the entire sequence.

The present invention is also directed to an isolated nucleic acid molecule comprising a polynucleotide sequence that hybridizes to SEQ ID NO:42 and/or SEQ ID NO:43 or that hybridizes to a polynucleotide sequence that is at least 95% identical to SEQ ID NO:42 and/or SEQ ID NO:43. In some embodiments, the isolated nucleic acid molecule comprises a polynucleotide sequence that is fully complementary to SEQ ID NO:42 or SEQ ID NO:43 or to a polynucleotide sequence that is at least 95% identical to SEQ ID NO:42 or SEQ ID NO:43. In some embodiments, an EF1 short or EF1 long promoter of the present invention includes an EF1 short or long promoter homologue that is sufficiently similar to a naturally occurring EF1 short and/or long promoter sequence, respectively, that the nucleic acid sequence of the homologue is capable of hybridizing under moderate, high, or very high stringency conditions (described below) to the complement of the nucleic acid sequence of the naturally occurring EF1 short and/or long promoter, respectively. In some embodiments, an EF1 short and/or long promoter sequence of the invention hybridizes under moderate, high or very high stringency conditions to the complement of SEQ ID NO:42 and/or SEQ ID NO:43, respectively.

In some embodiments, the promoter of the invention comprises the EF1 long promoter of pAB0018 as deposited in ATCC Accession No. PTA-9616.

In some embodiments, an isolated nucleic acid molecule of the invention comprises a 60S short promoter ("60S short" or "60S-S" promoter) or 60S long promoter ("60S long" or "60S-L" promoter). A 60S short or long promoter of the invention is a region of DNA that is naturally located upstream (towards the 5' region) of the 60S coding region and that directs 60S transcription. In some embodiments, the 60S short promoter has a polynucleotide sequence represented by SEQ ID NO:44. In some embodiments, the 60S long promoter has a polynucleotide sequence represented by SEQ ID NO:45. In some embodiments, an isolated nucleic acid molecule of the invention comprises a polynucleotide sequence that is at least about 65%, at least about 70%, at least about 75%, at least about 80%, at least about 85%, at least about 90%, at least about 95%, at least about 96%, at least about 97%, at least about 98%, or at least about 99% identical to SEQ ID NO:44 or SEQ ID NO:45, wherein the polynucleotide sequence has promoter activity (i.e., has basal promoter transcriptional activity, at least for an 60S short or long promoter sequence, respectively), at least in a thraustochytrid. The homology (or % identity) can be found over a sequence of at least 10, at least 20, at least 30, at least 40, at least 50, at least 100, at least 200, at least 300, at least 400, or at least 500 nucleotides, or over the entire sequence.

The present invention is also directed to an isolated nucleic acid molecule comprising a polynucleotide sequence that hybridizes to SEQ ID NO:44 and/or SEQ ID NO:45 or that hybridizes to a polynucleotide sequence that is at least 95% identical to SEQ ID NO:44 and/or SEQ ID NO:45. In some embodiments, the isolated nucleic acid molecule comprises a polynucleotide sequence that is fully complementary to SEQ ID NO:44 and/or SEQ ID NO:45 or to a polynucleotide sequence that is at least 95% identical to SEQ ID NO:44 and/or SEQ ID NO:45. In some embodiments, a 60S short or 60S long promoter of the present invention includes a 60S short or 60S long promoter homologue that is sufficiently similar to a naturally occurring 60S short or 60S long promoter sequence, respectively, that the nucleic acid sequence of the homologue is capable of hybridizing under moderate, high, or very high stringency conditions (described below) to the complement of the nucleic acid sequence of the naturally occurring 60S short and/or 60S long promoter, respectively. In some embodiments, a 60S short and/or 60S long promoter sequence of the invention hybridizes under moderate, high or very high stringency conditions to the complement of SEQ ID NO:44 and/or SEQ ID NO:45, respectively.

In some embodiments, the promoter of the invention comprises the 60S long promoter of pAB0011 as deposited in ATCC Accession No. PTA-9614.

In some embodiments, an isolated nucleic acid molecule of the invention comprises a Sec1 promoter ("Sec1 promoter"). A Sec1 promoter of the invention is a region of DNA that is naturally located upstream (towards the 5' region) of the Sec1 coding region and that directs Sec1 transcription. In some embodiments, the Sec1 promoter has a polynucleotide sequence represented by SEQ ID NO:46. In some embodiments, an isolated nucleic acid molecule of the invention comprises a polynucleotide sequence that is at least about 65%, at least about 70%, at least about 75%, at least about 80%, at least about 85%, at least about 90%, at least about 95%, at least about 96%, at least about 97%, at least about 98%, or at least about 99% identical to SEQ ID NO:46, wherein the polynucleotide sequence has promoter activity (i.e., has basal promoter transcriptional activity, at least for a Sec1 sequence), at least in a thraustochytrid. The homology (or % identity) can be found over a sequence of at least 10, at least 20, at least 30, at least 40, at least 50, at least 100, at least 200, at least 300, at least 400, or at least 500 nucleotides, or over the entire sequence.

The present invention is also directed to an isolated nucleic acid molecule comprising a polynucleotide sequence that hybridizes to SEQ ID NO:46 or that hybridizes to or a polynucleotide sequence that is at least 95% identical to SEQ ID NO: 46. In some embodiments, the isolated nucleic acid molecule comprises a polynucleotide sequence that is fully complementary to SEQ ID NO:46 or to a polynucleotide sequence that is at least 95% identical to SEQ ID NO:46. In some embodiments, a Sec1 promoter of the present invention includes a Sec1 promoter homologue that is sufficiently similar to a naturally occurring Sec1 promoter sequence that the nucleic acid sequence of the homologue is capable of hybridizing under moderate, high, or very high stringency conditions (described below) to the complement of the nucleic acid sequence of the naturally occurring Sec1 promoter. In some embodiments, a Sec1 promoter sequence of the invention hybridizes under moderate, high or very high stringency conditions to the complement of SEQ ID NO:46.

In some embodiments, the promoter of the invention comprises the Sec1 promoter of pAB0022 as deposited in ATCC Accession No. PTA-9613.

Terminators

The present invention is also directed to novel regulatory control elements that are transcription terminators. A terminator region of the invention is a section of genetic sequence that marks the end of a gene sequence in genomic DNA for transcription.

In some embodiments, the terminator region is from a microorganism of the phylum Labyrinthulomycota. In some embodiments, the terminator region is from a thraustochytrid. In some embodiments, the terminator region is from a *Schizochytrium* or a *Thraustochytrium*. *Schizochytrium* include, but are not limited to, *Schizochytrium aggregutum*, *Schizochytrium limacinum*, *Schizochytrium* sp. (S31) (ATCC 20888), *Schizochytrium* sp. (S8) (ATCC 20889), *Schizochytrium* sp. (LC-RM) (ATCC 18915), *Schizochytrium* sp. (SR 21), deposited strain ATCC 28209, and deposited strain IFO 32693.

A terminator region of the invention can have terminator activity at least in a thraustochytrid and includes full-length terminator sequences and functional fragments thereof, fusion sequences, and homologues of a naturally occurring terminator region. A homologue of a terminator differs from a naturally occurring terminator in that at least one or a few, but not limited to one or a few, nucleotides have been deleted, inserted, inverted, substituted and/or derivatized. In some embodiments, homologues of a terminator of the invention retain activity as a terminator region at least in a thraustochytrid, although the activity can be increased, decreased, or made dependant upon certain stimuli.

In some embodiments, the present invention comprises an isolated nucleic acid molecule comprising a terminator region of a PUFA PKS OrfC gene ("PKS OrfC terminator region"). A PKS OrfC terminator region of the invention is a section of genetic sequence that marks the end of the OrfC gene sequence in genomic DNA for transcription. In some embodiments, the teiminator region has a polynucleotide sequence represented by SEQ ID NO:4. The terminator region disclosed in SEQ ID NO:4 is a naturally occurring (wild-type) terminator sequence from a thraustochytrid microorganism, and, specifically, is a *Schizochytrium* PKS OrfC terminator region and is termed "OrfC terminator element 1." In some embodiments, an isolated nucleic acid molecule of the invention comprises a polynucleotide sequence that is at least about 65%, at least about 70%, at least about 75%, at least about 80%, at least about 85%, at least about 90%, at least about 95%, at least about 96%, at least about 97%, at least about 98%, or at least about 99% identical to SEQ ID NO:4, and that functions at least as a PUFA PKS OrfC terminator region at least in a thraustochytrid. The homology (or % identity) can be found over a sequence of at least 10, at least 20, at least 30, at least 40, at least 50, at least 100, at least 150, or at least 200 nucleotides, or over the entire sequence.

The present invention is also directed to an isolated nucleic acid molecule comprising a polynucleotide sequence that hybridizes to SEQ ID NO:4 or that hybridizes to a polynucleotide sequence that is at least 95% identical to SEQ ID NO:4. In some embodiments, the isolated nucleic acid molecule comprises an isolated nucleic acid molecule comprising a polynucleotide sequence that is fully complementary to SEQ ID NO:4 or to a polynucleotide sequence that is at least 95% identical to SEQ ID NO:4. In some embodiments, a PKS OrfC terminator region of the present invention includes a PKS OrfC terminator region homologue that is sufficiently similar to a naturally occurring PUFA PKS OrfC terminator region that the nucleic acid sequence of a homologue is capable of hybridizing under moderate, high, or very high stringency conditions (described below) to the complement of the nucleic acid sequence of the naturally occurring PKS OrfC terminator region. In some embodiments, a PKS OrfC terminator region sequence hybridizes under moderate, high, or very high stringency conditions to the complement of SEQ ID NO:4.

In some embodiments, the terminator of the invention comprises the OrfC terminator region of pAB0011 as deposited in ATCC Accession No. PTA-9614.

Signal Peptides

The present invention is also directed to novel nucleic acid molecules that encode signal peptides.

In some embodiments, the invention is directed to an isolated nucleic acid molecule comprising a polynucleotide sequence encoding a signal peptide of a secreted protein from a microorganism of the phylum Labyrinthulomycota. In some embodiments, the microorganism is a thraustochytrid. In some embodiments, the microorganism is a *Schizochytrium* or a *Thraustochytrium*.

A signal peptide of the invention can have secretion signal activity in a thraustochytrid, and includes full-length peptides and functional fragments thereof, fusion peptides, and homologues of a naturally occurring signal peptide. A homologue of a signal peptide differs from a naturally occurring signal peptide in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation, and/or addition of glycosylphosphatidyl inositol). In some embodiments, homologues of a signal peptide retain activity as a signal at least in a thraustochytrid, although the activity can be increased, decreased, or made dependant upon certain stimuli.

In some embodiments, the isolated nucleic acid molecule comprises a polynucleotide sequence encoding a Na/Pi-IIb2 transporter protein signal peptide. A Na/Pi-IIb2 transporter protein signal peptide can have signal targeting activity at least for a Na/Pi-IIb2 transporter protein at least in a thraustochytrid, and includes full-length peptides and functional fragments thereof, fusion peptides, and homologues of a naturally occurring Na/Pi-IIb2 transporter protein signal peptide. In some embodiments, the Na/Pi-IIb2 transporter protein signal peptide has an amino acid sequence represented by SEQ ID NO:1. In some embodiments, the Na/Pi-IIb2 transporter protein signal peptide has an amino acid sequence represented by SEQ ID NO:15. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:1 or SEQ ID NO:15, wherein the polynucleotide sequence encodes an amino acid sequence that functions as a signal peptide, at least for a Na/Pi-IIb2 transporter protein, at least in a thraustochytrid. In some embodiments, the isolated nucleic acid molecule comprises a polynucleotide sequence encoding an isolated amino acid sequence comprising a functional fragment of SEQ ID NO:1 or SEQ ID NO:15 that functions as a signal peptide, at least for a Na/Pi-IIb2 transporter protein, at least in a thraustochytrid. In some embodiments, the isolated nucleic acid molecule comprises SEQ ID NO:2. In some embodiments, the isolated nucleic acid molecule comprises a polynucleotide sequence that hybridizes to any of: (i) SEQ ID NO:2; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:2; (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:1, and (vi) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:15. In some embodiments, the isolated nucleic acid molecule comprises a polynucleotide sequence that is fully complementary to any of: (i) SEQ ID NO:2, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:2, (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:1, and (vi) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:15.

The present invention is also directed to an isolated polypeptide comprising a Na/Pi-IIb2 transporter signal peptide amino acid sequence. In some embodiments, the isolated polypeptide comprises an amino acid sequence selected from the group consisting of: (i) SEQ ID NO:1, (ii) SEQ ID NO:15, and (iii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:1 or SEQ ID NO:15 that functions as a signal sequence, at least for a Na/Pi-IIb2 transporter, at least in a thraustochytrid. In some embodiments, the isolated polypeptide comprises the first 20, 21, 22, 23, 24, 25, 26, 27, 28, 29, 30, 31, 32, 33, 34 or 35 amino acid residues of SEQ ID NO:15 (i.e., SEQ ID NO:15 wherein the last 1, 2, 3, 4, 5, 6, 7, 8, 9, 10, 11, 12, 13, 14, 15, 16, 17, or 18 amino acids at the C-terminal end of this sequence are deleted). The 18 amino acids located at the C-terminal end of SEQ ID NO:15 are predicted to be part of the mature Na/Pi transporter protein and the cleavage site of the signal sequence is predicted to occur between amino acid residues 35 and 36 of SEQ ID NO:15. However, a signal peptide that includes up to all 18 amino acids of the mature Na/Pi transporter protein (i.e., the last 18 amino acid residues of SEQ ID NO:15) can be employed and is contemplated by the present invention. According to the present invention, an isolated polypeptide is a polypeptide that has been removed from its natural milieu (i.e., that has been subject to human manipulation) and can include purified proteins, purified peptides, partially purified proteins, partially purified peptides, recombinantly produced proteins or peptides, and synthetically produced proteins or peptides, for example. As such, "isolated" does not reflect the extent to which the polypeptide has been purified. In some embodiments, an isolated Na/Pi-IIb2 transporter signal peptide of the present invention is produced recombinantly.

In some embodiments, the isolated nucleic acid molecule comprises a polynucleotide sequence encoding an alpha-1,6-mannosyltransferase (ALG12) signal peptide. An ALG12 signal peptide can have signal targeting activity at least for an ALG12 protein, at least in a thraustochytrid, and includes full-length peptides and functional fragments thereof, fusion peptides, and homologues of a naturally occurring ALG12 signal peptide. In some embodiments, the ALG12 signal peptide has an amino acid sequence represented by SEQ ID NO:59. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:59, wherein the polynucleotide sequence encodes an amino acid sequence that functions as a signal peptide, at least for an ALG12 protein, at least in a thraustochytrid. In some embodiments, the isolated nucleic acid molecule comprises a polynucleotide sequence encoding an isolated amino acid sequence comprising a functional fragment of SEQ ID NO:59 that functions as a signal peptide at least for an ALG12 protein, at least in a thraustochytrid. In some embodiments, the isolated nucleic acid molecule comprises SEQ ID NO:60. In some embodiments, the isolated nucleic acid molecule comprises a polynucleotide sequence that hybridizes to any of: (i) SEQ ID NO:60; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:60; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:59. In some embodiments, the isolated nucleic acid molecule comprises a polynucleotide sequence that is fully complementary to any of: (i) SEQ ID NO:60, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:60, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:59.

The present invention is also directed to an isolated polypeptide comprising a ALG12 signal peptide amino acid sequence. In some embodiments, the isolated polypeptide comprises an amino acid sequence selected from the group consisting of: (i) SEQ ID NO:59 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:59 that functions as a signal sequence, at least for an ALG12 protein, at least in a thraustochytrid. In some embodiments, the isolated polypeptide comprises the first 24, 25, 26, 27, 28, 29, 30, 31, or 32 amino acid residues of SEQ ID NO:59. In some embodiments, an isolated ALG12 signal peptide of the present invention is produced recombinantly.

In some embodiments, the isolated nucleic acid molecule comprises a polynucleotide sequence encoding a binding immunoglobulin protein (BiP) signal peptide. A BiP signal peptide can have signal targeting activity at least for a BiP protein, at least in a thraustochytrid, and includes full-length peptides and functional fragments thereof, fusion peptides, and homologues of a naturally occurring BiP signal peptide. In some embodiments, the BiP signal peptide has an amino acid sequence represented by SEQ ID NO:61. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:61, wherein the polynucleotide sequence encodes an amino acid sequence that functions as a signal peptide, at least for a BiP protein, at least in a thraustochytrid. In some embodiments, the isolated nucleic acid molecule comprises a polynucleotide sequence encoding an isolated amino acid sequence comprising a functional fragment of SEQ ID NO:61 that functions as a signal peptide at least for a BiP protein, at least in a thraustochytrid. In some embodiments, the isolated nucleic acid molecule comprises SEQ ID NO:62. In some embodiments, the isolated nucleic acid molecule comprises a polynucleotide sequence that hybridizes to any of: (i) SEQ ID NO:62; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:62; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:61. In some embodiments, the isolated nucleic acid molecule comprises a polynucleotide sequence that is fully complementary to any of: (i) SEQ ID NO:62, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:62, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:61.

The present invention is also directed to an isolated polypeptide comprising a BiP signal peptide amino acid sequence. In some embodiments, the isolated polypeptide comprises an amino acid sequence selected from the group consisting of: (i) SEQ ID NO:61 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:61 that functions as a signal sequence, at least for an BiP protein, at least in a thraustochytrid. In some embodiments, the isolated polypeptide comprises the first 23, 24, 25, 26, 27, 28, 29, 30, or 31 amino acid residues of SEQ ID NO:61. In some embodiments, an isolated BiP signal peptide of the present invention is produced recombinantly.

In some embodiments, the isolated nucleic acid molecule comprises a polynucleotide sequence encoding an alpha-1,3-glucosidase (GLS2) signal peptide. A GLS2 signal peptide can have signal targeting activity at least for a GLS2 protein, at least in a thraustochytrid, and includes full-length peptides and functional fragments thereof, fusion peptides, and homologues of a naturally occurring GLS2 signal peptide. In some embodiments, the GLS2 signal peptide has an amino acid sequence represented by SEQ ID NO:63. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:63, wherein the polynucleotide sequence encodes an amino acid sequence that functions as a signal peptide, at least for a GLS2 protein, at least in a thraustochytrid. In some embodiments, the isolated nucleic acid molecule comprises a polynucleotide sequence encoding an isolated amino acid sequence comprising a functional fragment of SEQ ID NO:63 that functions as a signal peptide at least for a GLS2 protein, at least in a thraustochytrid. In some embodiments, the isolated nucleic acid molecule comprises SEQ ID NO:64. In some embodiments, the isolated nucleic acid molecule comprises a polynucleotide sequence that hybridizes to any of: (i) SEQ ID NO:64; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:64; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:63. In some embodiments, the isolated nucleic acid molecule comprises a polynucleotide sequence that is fully complementary to any of: (i) SEQ ID NO:64, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:64, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:63.

The present invention is also directed to an isolated polypeptide comprising a GLS2 signal peptide amino acid sequence. In some embodiments, the isolated polypeptide comprises an amino acid sequence selected from the group consisting of: (i) SEQ ID NO:63 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:63 that functions as a signal sequence, at least for an GLS2 protein, at least in a thraustochytrid. In some embodiments, the isolated polypeptide comprises the first 30, 31, 32, 33, 34, 35, 36, 37, or 38 amino acid residues of SEQ ID NO:63. In some embodiments, an isolated GLS2 signal peptide of the present invention is produced recombinantly.

In some embodiments, the isolated nucleic acid molecule comprises a polynucleotide sequence encoding an alpha-1,3-1,6-mannosidase-like signal peptide. A alpha-1,3-1,6-mannosidase-like signal peptide can have signal targeting activity at least for an alpha-1,3-1,6-mannosidase-like protein, at least in a thraustochytrid, and includes full-length peptides and functional fragments thereof, fusion peptides, and homologues of a naturally occurring alpha-1,3-1,6-mannosidase-like signal peptide. In some embodiments, the alpha-1,3-1,6-mannosidase-like signal peptide has an amino acid sequence represented by SEQ ID NO:65. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:65, wherein the polynucleotide sequence encodes an amino acid sequence that functions as a signal peptide, at least for an alpha-1,3-1,6-mannosidase-like protein, at least in a thraustochytrid. In some embodiments, the isolated nucleic acid molecule comprises a polynucleotide sequence encoding an isolated amino acid sequence comprising a functional fragment of SEQ ID NO:65 that functions as a signal peptide at least for an alpha-1,3-1,6-mannosidase-like protein, at least in a thraustochytrid. In some embodiments, the isolated nucleic acid molecule comprises SEQ ID NO:66. In some embodiments, the isolated nucleic acid molecule comprises a polynucleotide sequence that hybridizes to any of: (i) SEQ ID NO:66; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:66; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:65. In some embodiments, the isolated nucleic acid molecule comprises a polynucleotide sequence that is fully complementary to any of: (i) SEQ ID NO:66, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:66, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:65.

The present invention is also directed to an isolated polypeptide comprising a alpha-1,3-1,6-mannosidase-like signal peptide amino acid sequence. In some embodiments, the isolated polypeptide comprises an amino acid sequence selected from the group consisting of: (i) SEQ ID NO:65 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:65 that functions as a signal sequence, at least for an alpha-1,3-1,6-mannosidase-like; at least in a thraustochytrid. In some embodiments, the isolated polypeptide comprises the first 24, 25, 26, 27, 28, 29, 30, 31, 32, 33, or 34 amino acid residues of SEQ ID NO:65. In some embodiments, an isolated alpha-1,3-1,6-mannosidase-like signal peptide of the present invention is produced recombinantly.

In some embodiments, the isolated nucleic acid molecule comprises a polynucleotide sequence encoding an alpha-1,3-1,6-mannosidase-like #1 signal peptide. An alpha-1,3-1,6-mannosidase-like #1 signal peptide can have signal targeting activity at least for an alpha-1,3-1,6-mannosidase-like #1 protein, at least in a thraustochytrid, and includes full-length peptides and functional fragments thereof, fusion peptides, and homologues of a naturally occulting alpha-1,3-1,6-mannosidase-like #1 signal peptide. In some embodiments, the alpha-1,3-1,6-mannosidase-like #1 signal peptide has an amino acid sequence represented by SEQ ID NO:67. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:67, wherein the polynucleotide sequence encodes an amino acid sequence that functions as a signal peptide, at least for an alpha-1,3-1, 6-mannosidase-like #1 polypeptide; at least in a thraustochytrid. In some embodiments, the isolated nucleic acid molecule comprises a polynucleotide sequence encoding an isolated amino acid sequence comprising a functional fragment of SEQ ID NO:67 that functions as a signal peptide at least for an alpha-1,3-1,6-mannosidase-like #1 protein, at least in a thraustochytrid. In some embodiments, the isolated nucleic acid molecule comprises SEQ ID NO:68. In some embodiments, the isolated nucleic acid molecule comprises a polynucleotide sequence that hybridizes to any of: (i) SEQ ID NO:68; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:68; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:67. In some embodiments, the isolated nucleic acid molecule comprises a polynucleotide sequence that is fully complementary to any of: (i) SEQ ID NO:68, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:68, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:67.

The present invention is also directed to an isolated polypeptide comprising a alpha-1,3-1,6-mannosidase-like #1 signal peptide amino acid sequence. In some embodiments, the isolated polypeptide comprises an amino acid sequence selected from the group consisting of: (i) SEQ ID NO:67 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:67 that functions as a signal sequence, at least for an alpha-1,3-1,6-mannosidase-like #1 protein, at least in a thraustochytrid. In some embodiments, the isolated polypeptide comprises the first 23, 24, 25, 26, 27, 28, or 29 amino acid residues of SEQ ID NO:67. In some embodiments, an isolated alpha-1,3-4,6-mannosidase-like #1 signal peptide of the present invention is produced recombinantly.

In some embodiments, the isolated nucleic acid molecule comprises a polynucleotide sequence encoding an alpha-1,2-mannosidase-like signal peptide. An alpha-1,2-mannosidase-like signal peptide can have signal targeting activity at least for an alpha-1,2-mannosidase-like protein, at least in a thraustochytrid, and includes full-length peptides and functional fragments thereof, fusion peptides, and homologues of a naturally occurring alpha-1,2-mannosidase-like signal peptide. In some embodiments, the alpha-1,2-mannosidase-like signal peptide has an amino acid sequence represented by SEQ ID NO:69. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:69, wherein the polynucleotide sequence encodes an amino acid sequence that functions as a signal peptide, at least for an alpha-1,2-mannosidase-like protein, at least in a thraustochytrid. In some embodiments, the isolated nucleic acid molecule comprises a polynucleotide sequence encoding an isolated amino acid sequence comprising a functional fragment of SEQ ID NO:69 that functions as a signal peptide at least for an alpha-1,2-mannosidase-like protein, at least in a thraustochytrid. In some embodiments, the isolated nucleic acid molecule comprises SEQ ID NO:70. In some embodiments, the isolated nucleic acid molecule comprises a polynucleotide sequence that hybridizes to any of: (i) SEQ ID NO:70; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:70; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:69. In some embodiments, the isolated nucleic acid molecule comprises a polynucleotide sequence that is fully complementary to any of: (i) SEQ ID NO:70, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:70, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:69.

The present invention is also directed to an isolated polypeptide comprising a alpha-1,2-mannosidase-like signal peptide amino acid sequence. In some embodiments, the isolated polypeptide comprises an amino acid sequence selected from the group consisting of: (i) SEQ ID NO:69 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:69 that functions as a signal sequence, at least for an alpha-1,2-mannosidase-like protein, at least in a thraustochytrid. In some embodiments, the isolated polypeptide comprises the first 26, 27, 28, 29, 30, 31, 32, 33, 34, 35, or 36 amino acid residues of SEQ ID NO:69. In some embodiments, an isolated alpha-1,2-mannosidase-like signal peptide of the present invention is produced recombinantly.

In some embodiments, the isolated nucleic acid molecule comprises a polynucleotide sequence encoding a beta-xylosdiase-like signal peptide. A beta-xylosdiase-like signal peptide can have signal targeting activity at least for a beta-xylosdiase-like protein, at least in a thraustochytrid, and includes full-length peptides and functional fragments thereof, fusion peptides, and homologues of a naturally occurring beta-xylosdiase-like signal peptide. In some embodiments, the beta-xylosdiase-like signal peptide has an amino acid sequence represented by SEQ ID NO:71. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:71, wherein the polynucleotide sequence encodes an amino acid sequence that functions as a signal peptide, at least for a beta-xylosdiase-like protein, at least in a thraustochytrid. In some embodiments, the isolated nucleic acid molecule comprises a polynucleotide sequence encoding an isolated amino acid sequence comprising a functional fragment of SEQ ID NO:71 that functions as a signal peptide at least for a beta xylosdiase-like protein, at least in a thraustochytrid. In some embodiments, the isolated nucleic acid molecule comprises SEQ ID NO:72. In some embodiments, the isolated nucleic acid molecule comprises a polynucleotide sequence that hybridizes to any of: (i) SEQ ID NO:72; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:72; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:71. In some embodiments, the isolated nucleic acid molecule comprises a polynucleotide sequence that is fully complementary to any of: (i) SEQ ID NO:72, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:72, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:71.

The present invention is also directed to an isolated polypeptide comprising a beta-xylosdiase-like signal peptide amino acid sequence. In some embodiments, the isolated polypeptide comprises an amino acid sequence selected from the group consisting of: (i) SEQ ID NO:71 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:71 that functions as a signal sequence, at least for a beta-xylosdiase-like protein, at least in a thraustochytrid. In some embodiments, the isolated polypeptide comprises the first 24, 25, 26, 27, 28, 29, or 30 amino acid residues of SEQ ID NO:71. In some embodiments, an isolated beta-xylosdiase-like signal peptide of the present invention is produced recombinantly.

In some embodiments, the isolated nucleic acid molecule comprises a polynucleotide sequence encoding a carotene synthase signal peptide. A carotene synthase signal peptide can have signal targeting activity at least for a carotene synthase protein, at least in a thraustochytrid, and includes full-length peptides and functional fragments thereof, fusion peptides, and homologues of a naturally occurring carotene synthase signal peptide. In some embodiments, the carotene synthase signal peptide has an amino acid sequence represented by SEQ ID NO:73. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:73, wherein the polynucleotide sequence encodes an amino acid sequence that functions as a signal peptide, at least for a carotene synthase protein, at least in a thraustochytrid. In some embodiments, the isolated nucleic acid molecule comprises a polynucleotide sequence encoding an isolated amino acid sequence comprising a functional fragment of SEQ ID NO:73 that functions as a signal peptide at least for a carotene synthase protein; at least in a thraustochytrid. In some embodiments, the isolated nucleic acid molecule comprises SEQ ID NO:74. In some embodiments, the isolated nucleic acid molecule comprises a polynucleotide sequence that hybridizes to any of: (i) SEQ ID NO:74; (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:74; and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:73. In some embodiments, the isolated nucleic acid molecule comprises a polynucleotide sequence that is fully complementary to any of: (i) SEQ ID NO:74, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:74, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:73.

The present invention is also directed to an isolated polypeptide comprising a carotene synthase signal peptide amino acid sequence. In some embodiments, the isolated polypeptide comprises an amino acid sequence selected from the group consisting of: (i) SEQ ID NO:73 and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:73 that functions as a signal sequence, at least for a carotene synthase protein, at least in a thraustochytrid. In some embodiments, the isolated polypeptide comprises the first 15, 16, 17, 18, 19, 20, 21, 29, 30, 31, 32, 33 or 34 amino acid residues of SEQ ID NO:73. In some embodiments, an isolated carotene synthase signal peptide of the present invention is produced recombinantly.

In some embodiments, the isolated nucleic acid molecule comprises a polynucleotide sequence encoding a Sec1 protein ("Sec1") signal peptide. A Sec1 signal peptide can have secretion signal activity at least for a Sec1 protein at least in a thraustochytrid, and includes full-length peptides and functional fragments thereof, fusion peptides, and homologues of a naturally occurring Sec1 signal peptide. In some embodiments, the Sec1 signal peptide is represented by SEQ ID NO:37. In some embodiments, an isolated nucleic acid molecule of the invention comprises a polynucleotide sequence encoding an amino acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:37, wherein the polynucleotide sequence encodes an amino acid sequence that functions as a signal peptide at least for a Sec1 protein, at least in a thraustochytrid. In some embodiments, the isolated nucleic acid molecule comprises a polynucleotide sequence encoding an isolated amino acid sequence comprising a functional fragment of SEQ ID NO:37 that functions as a signal peptide, at least for a Sec1 protein, at least in a thraustochytrid. In some embodiments, the isolated nucleic acid molecule comprises SEQ ID NO:38. In some embodiments, the isolated nucleic acid molecule comprises a polynucleotide sequence that hybridizes to any of: (i) SEQ ID NO:38, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:38, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:37. In some embodiments, the isolated nucleic acid molecule comprises a polynucleotide sequence that is fully complementary to any of: (i) SEQ ID NO:38, (ii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:38, and (iii) a polynucleotide sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to a nucleic acid sequence that encodes SEQ ID NO:37.

The present invention is also directed to an isolated polypeptide comprising a Sec1 signal peptide amino acid sequence. In some embodiments, the isolated polypeptide comprises an amino acid sequence selected from the group consisting of: (i) SEQ ID NO:37, and (ii) an amino acid sequence at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO:37 that functions as a signal sequence, at least for a Sec1 transporter, at least in a thraustochytrid. In some embodiments, the isolated polypeptide comprises an amino acid sequence comprising the first 18 or 19 amino acid residues of SEQ ID NO:37 (i.e., SEQ ID NO:37, wherein the last 1 or 2 amino acids at the C-terminal end of this sequence are deleted). In some embodiments, an isolated Sec1 signal peptide of the present invention is produced recombinantly.

In some embodiments, an isolated nucleic acid molecule of the present invention comprises an OrfC promoter, EF1 short promoter, EF1 long promoter, 60S short promoter, 60S long promoter, Sect promoter, PKS OrfC terminator region, sequence encoding a Na/Pi-IIb2 transporter protein signal peptide, or sequence encoding a Sec1 transport protein signal peptide of the present invention that is operably linked to the 5' end of a nucleic acid sequence encoding a protein. The present invention also encompasses recombinant vectors (including, but not limited to, expression vectors), expression cassettes, and host cells comprising an OrfC promoter, EF1 short promoter, EF1 long promoter, 60S short promoter, 60S long promoter, Sec1 promoter, PKS OrfC terminator region, sequence encoding a Na/Pi-IIb2 transporter protein signal peptide, or sequence encoding a Sec1 transport protein signal peptide of the present invention that is operably linked to the 5' end of a nucleic acid sequence encoding a protein.

Recombinant vectors (including, but not limited to expression vectors), expression cassettes, host cells, and microorganisms comprising any of the above-described isolated nucleic acid molecules of the present invention (e.g., nucleic acid molecules comprising an OrfC promoter, EF1 short promoter, EF1 long promoter, 60S short promoter, 60S long promoter, Sec1 promoter, PKS OrfC terminator region, sequence encoding a Na/Pi-IIb2 transporter protein signal peptide, or sequence encoding a Sec1 transport protein signal peptide) are also encompassed by the present invention, as are methods of introducing the vectors and/or expression cassettes into the host cells and recombinant microorganisms. Suitable vectors and expression cassettes can be selected or constructed so as to contain appropriate regulatory sequences, terminator fragments, polyadenylation sequences, enhancer sequences, marker genes, and other sequences as appropriate. Additional details regarding the vectors, expression cassettes, and host cells are set forth herein.

As used herein, unless otherwise specified, reference to a percent (%) identity (and % identical) refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (see, for example, Altschul, S., et al., *Nucleic Acids Res.* 25:3389-3402 (1997), incorporated herein by reference in its entirety); (2) a BLAST 2 alignment using the parameters described below; (3) and/or PSI-BLAST (Position-Specific Iterated BLAST) with the standard default parameters. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described, for example, in Tatusova and Madden, *FEMS Microbiol. Lett.* 174:247-250 (1999), incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. In some embodiments, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties gap x_dropoff (50) expect (10) word size (11) filter (on).

For blastp, using 0 BLOSUM62 matrix:
Open gap (11) and extension gap (1) penalties
gap x_dropoff (50) expect (10) word size (3) filter (on).

As used herein, hybridization conditions refer to standard hybridization conditions under which nucleic acid molecules are used to identify similar nucleic acid molecules. See, for example, Sambrook J. and Russell D. (2001) Molecular cloning: A laboratory manual, 3rd ed. Cold Spring Harbor Laboratory Press, Cold Spring Harbor, N.Y., incorporated by reference herein in its entirety. In addition, formulae to calculate the appropriate hybridization and wash conditions to achieve hybridization permitting varying degrees of mismatch of nucleotides are disclosed, for example, in Meinkoth et al., Anal. Biochem. 138, 267-284 (1984), incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., for example, to calculate the appropriate hybridization and wash conditions to achieve these particular levels of nucleotide mismatch. Such conditions will vary, depending on whether DNA:RNA or DNA:DNA hybrids are being totaled. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), between about 28° C. and about 40° C. (more stringent), and between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., between about 38° C. and about 50° C., and between about 45° C. and about 55° C., with similarly stringent wash conditions. These values are based on calculations of a melting temperature for molecules larger than about 100 nucleotides, 0% formamide, and a G+C content of about 40%. Alternatively, $T_m$ can be calculated empirically as set forth in Sambrook et al. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Having generally described this invention, a further understanding can be obtained by reference to the examples provided herein. These examples are for purposes of illustration only and are not intended to be limiting.

Example 1

Construction of the *Schizochytrium* Protein Expression Vector pSchizE a. Construction of p07074#6:

The pSP73 vector (Promega, acc#X65333) was digested with XbaI and mung bean nuclease, and then purified and ligated to create the vector p070604#3. p070604#3 was then further digested with SphI, HpaI, and mung bean nuclease and then purified and religated to create the vector p070704#6.

b. Construction of pSchiz1:

pTUBzeo11-2 vector, as disclosed in WO02/083869, was digested with BamHI to release a 1122 base pair (bp) fragment containing the *Schizochytrium* α-tubulin promoter, the ble gene, and an SV40 terminator region. This fragment was gel purified and ligated into vector pYES2/CT (Invitrogen), which had been previously digested with BamHI. The resulting construct was then digested with SmaI, SphI, and mung bean nuclease in order to release a 540 bp fragment containing the α-tubulin promoter. The fragment was ligated into pUC19 (Genbank Accession No. L09137) that had been previously digested with BamHI, SmaI, and mung bean ligase, creating pSchiz1.

c. Construction of pSchiz2:

In a separate reaction, PCR was used to generate an amplicon encoding the SV40 terminator from pTUBzeo11-2 using the following primers, which incorporate NcoI and PciI restriction sites (shown in italics) for ligation:

```
Primer S4termF:
5'-GATCCCATGGCACGTGCTACG      (SEQ ID NO: 16)

Primer S4termR:
5'-GGCAACATGTATGATAAGATAC    (SEQ ID NO: 17)
```

The resulting amplicon was digested with NcoI and PciI to expose the sticky ends. This 265 bp fragment was then ligated into pSchiz1, which had been previously digested with NcoI. The resulting plasmid, termed pSchiz2, contained the α-tubulin promoter followed by the SV40 terminator.

d. Construction of pSchiz3:

In a separate reaction, PCR was used to amplify the multiple cloning site (MCS) from pYES2/CT using the following primers designed to add a SmaI site (shown in italics) to either end:

```
                                        (SEQ ID NO: 18)
    Primer C2mcsSmaF:    5'-GATCCCCGGGTTAAGCTTGGT (SEQ ID NO: 19)
    Primer C2mcsSmaR:    5'-ACTGGGGCCCGTTTAAACTC
```

The resulting MCS amplicon was then digested with SmaI and ligated into pSchiz2, which had been previously digested with NcoI and mung bean nuclease. The resulting vector, termed pSchiz3, contained the alpha tubulin promoter, the SV40 terminator, and the pYES2/CT MCS.

e. Construction of pSchiz0.5#4

PCR was used with the following primers and pSchiz3 as a template to generate an amplicon encoding the MCS cassette consisting of the α-tubulin promoter, the pYES2/CT MCS, and the SV40 terminator region.

```
Primer 5'tubMCS_BglII:
                                          (SEQ ID NO: 20)
5'-GACTAGATCTCAATTTTAGGCCCCCCACTGACCG Primer 3'SV40MCS_Sal:
                                          (SEQ ID NO: 21)
5'-GACTGTCGACCATGTATGATAAGATACATTGATG
```

These primers were designed to add BglII and SalI restriction sites (shown in italics) to the ends of the MCS cassette amplicon. The resulting PCR fragment was digested with BglII and SalI and ligated into p070704#6, which had also been previously digested with BglII and SalI, to generate pSchiz0.5#4.

f. Construction of pSchizE

PCR was used to generate a 4776 bp amplicon encoding the ALS gene (including its promoter and terminator regions) using the vector pMON50203, as described in U.S. Pat. No. 7,001,772, as a template. The following primers, which contain NdeI and BglII restriction sites (shown in italics), were used for this PCR reaction:

```
Primer 5'ALSproNde3:
                                          (SEQ ID NO: 22)
5'-GACTCATATGGCCCAGGCCTACTTTCAC Primer 3'ALStermBglII:
                                          (SEQ ID NO: 23)
5'GACTAGATCTGGGTCAAGGCAGAAGAATTCCGCC
```

The resulting ALS amplicon was then digested with BglII and NdeI. pSchiz0.5#4 was likewise digested with BglII and NdeI and the larger, 3171 bp band was gel purified and ligated to the purified ALS PCR amplicon. The resulting vector, termed pSchizE, was verified by sequencing and contained the ALS gene (including the promoter and terminator region) followed by an expression cassette that contained the *Schizochytrium* α-tubulin promoter, the pYES2/CT MCS, and the SV40 terminator region (see FIG. 5).

Example 2

Construction of the *Schizochytrium* Protein Expression Vector pSchiz-sG

Figure 6:
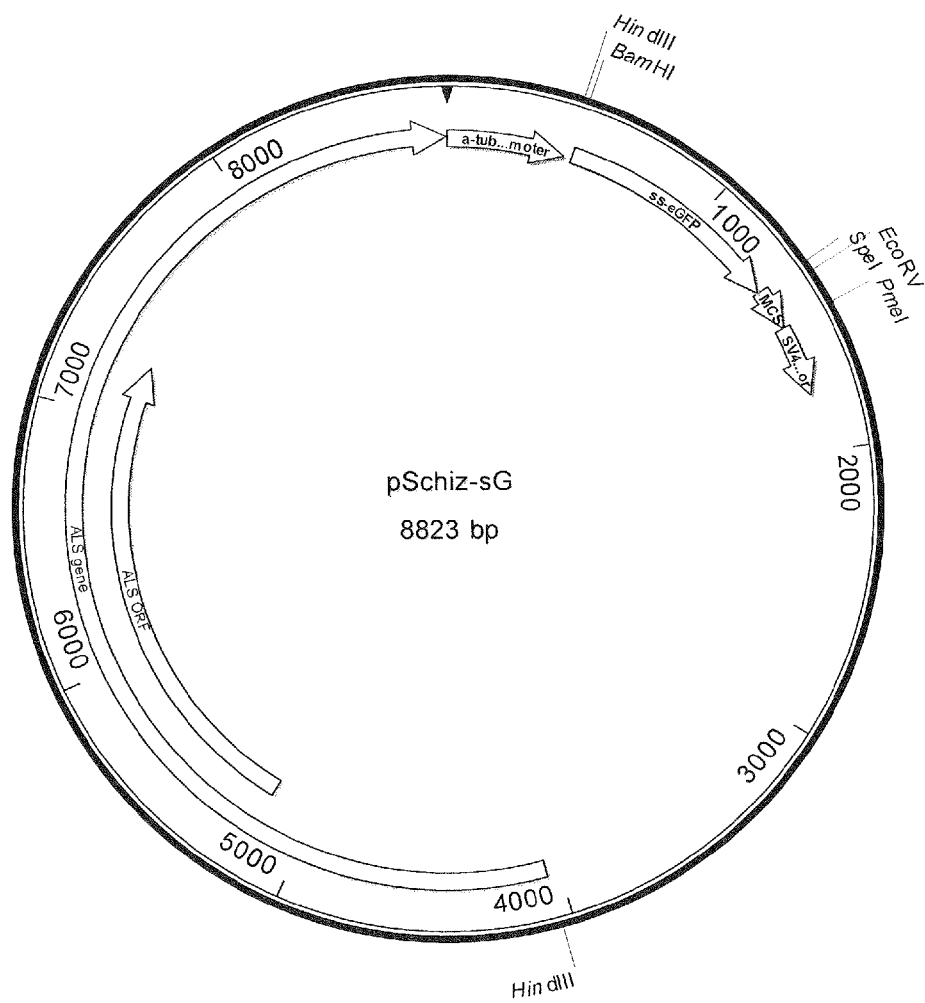
FIG. 6 shows a plasmid map of pSchiz-sG, also termed pC00001.

Expression and secretion of eGFP was achieved using pSchiz-sG (see FIG. 6). This plasmid is also teimed pC00001 and was deposited at the American Type Culture Collection, Patent Depository, 10801 University Boulevard, Manassas, Va. 20110-2209, on Nov. 18, 2008, and given ATCC Accession No. PTA-9617. This vector contains (i) the *Schizochytrium* α-tubulin promoter sequence followed by (ii) a sequence encoding the *Schizochytrium* Na/Pi transporter signal sequence with a fragment of the N-terminal portion of the mature transporter protein attached (SEQ ID NO:15), fused to the eGFP-encoding sequence followed by (iii) the remainder of the MCS and (iv) the SV40 terminator region. This vector also contains the *Schizochytrium* ALS gene as a selectable marker. The vector was constructed as described below.

The sequence chosen to encode the signal peptide (SEQ ID NO:2) was from a Na/Pi transporter isolated from a *Schizochytrium* EST library. The nucleotide sequences encoding the signal peptide and eGFP were fused by PCR using the eGFP-containing plasmid pPha-T1-eGFP (Apt et al., *J. Cell Sci.* 115:4061-4069 (2002)), and 3 primers designed to add the signal sequence. The first PCR reaction employed the eGfp containing plasmid as the template, a small primer at the 3' end of eGfp (primer sec.Gfp3'Spe, which contained a SpeI site, shown in italics below), and a 100 bp primer that flanked the 5° end of eGfp and the 3° end of the signal sequence (primer sec.Gfp5'1b, sec). The primer sequences were as follows:

```
Primer sec.Gfp5'1b:
                                          (SEQ ID NO: 24)
5'-TACTGGTTCCTTGTCGGCCTCGCCCTTCTCGGCGAT

GGCTTCAAGGTCATCGCCGGTGACTCCGCCGGTACGCTCTTCATGGTGAG

CAAGGGCGAGG

Primer sec.Gfp3'Spe:
                                          (SEQ ID NO: 25)
5'-CGTCACTAGTTTACTTGTACAGCTCGTCCATGCC
```

In the second PCR reaction, the amplicon product of first PCR was used as a template. The same 3' primer was used along with a second 100 bp 5' primer (sec.Gfp5'Bam) that incorporated the remainder of the signal sequence. The second 5' primer sequence contained a BamHI site (shown in italics below) and was as follows:

```
Primer sec.Gfp5'Bam:
                                          (SEQ ID NO: 26)
5'-TAATGGATCCATGGCCAACATCATGGCC

AACGTCACGCCCCAGGGCGTCGCCAAGGGCTTTGGCCTCTTTGTCGGCGT

GCTCTTCTTTCTCTACTGGTTCCTTGT
```

The resulting PCR product from this second PCR reaction contained BamHI and SpeI sites for cloning.

The amplicon of the second PCR reaction and pSchizE were both digested with BamHI and SpeI and ligated to each other to create the vector pSchiz-sG.

Example 3

Construction of the *Schizochytrium* Protein Expression Vector pSchiz-sGr

The pSchiz-sGr vector comprises an α-tubulin promoter, an eGFP nucleotide sequence with a sequence encoding an ER retention signal, an SV40 terminator region, and a mutated ALS selectable marker.

The common ER retention signal amino acid sequence HDEL was back-translated and the sequence encoding this retention signal (SEQ ID NO:14) was fused to eGFP by PCR using pSchiz-sG from Example 2 as a template. The oligonucleotide primers were designed to include the HDEL-encoding sequence (reverse complement underlined in the ss.eGfpHELD3'RV primer sequence below) in frame with a stop codon (shown boxed), plus a BamHI site (shown in italics) in one primer and an EroRV site (italicized) in the other primer.

```
Primer ss.eGfpHELD3'RV:
                                        (SEQ ID NO: 27)
5'-CCTGATATCTTACAACTCGTCGTGGTTGTACAGCTCGTCC Primer sec.Gfp5'Bam2:
                                        (SEQ ID NO: 28)
5'-TAATGGATCCATGGCCAACATCATGGCCAACGTCACGCCC

CAGGGCGTCGCCAAGGGCTTTGGCCTCTTTGTCGGCGTGCTCT

TCTTTCTCTACTGGTTCCTTGT
```

Figure 7:
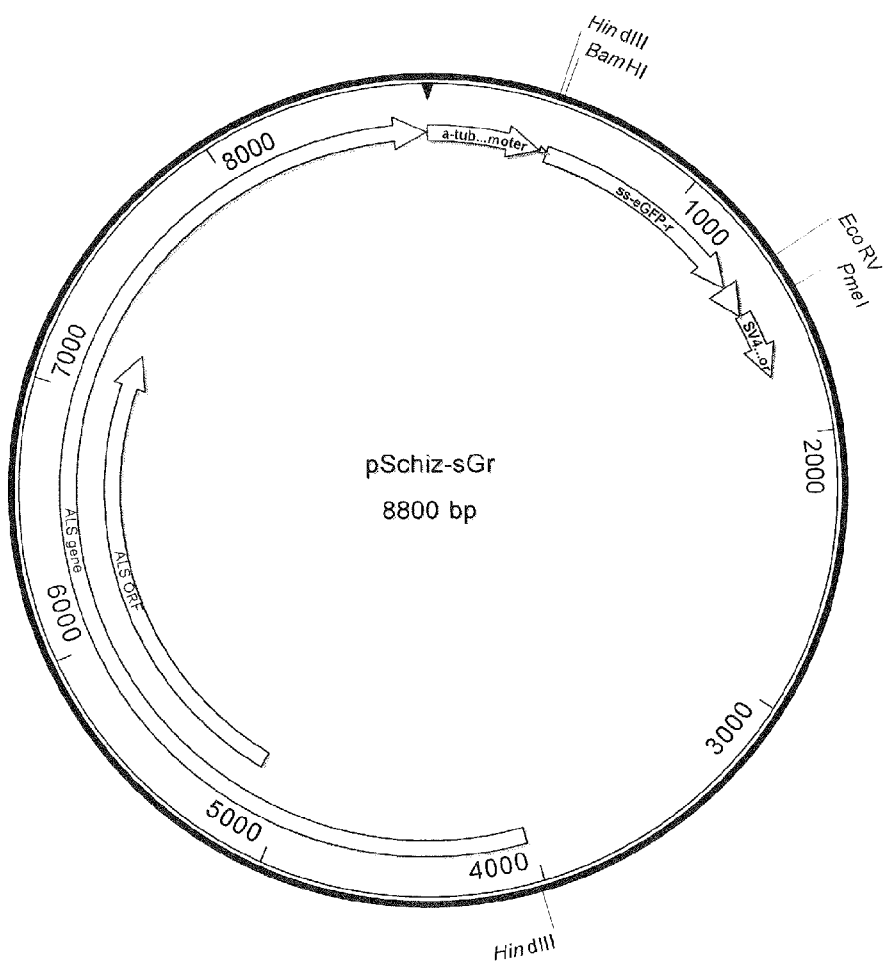
FIG. 7 shows a plasmid map of pSchiz-sGr.

The resulting PCR product was digested with BamHI and EcoRV and ligated to the larger fragment that resulted from digesting pSchizE (described in Example 1) with BamHI and EcoRV. The resulting vector was named pSchiz-sGr (see FIG. 7).

Example 4

Construction of the *Schizochytrium* Protein Expression Vector pSchiz-cG

As a comparative control, the pSchiz-cG vector was constructed to express eGFP in a fashion such that the fluorescent protein would accumulate in the cell cytoplasm. The pSchiz-cG plasmid comprises a *Schizochytrium* OrfC promoter, a polynucleotide sequence encoding eGFP, an SV40 terminator region, and a mutated *Schizochytrium* ALS selectable marker.

First, a 2000 bp sequence upstream of *Schizochytrium* ORFC was PCR amplified with the following primers from genomic DNA of *Schizochytrium* sp. ATCC 20888:

```
                                        (SEQ ID NO: 29)
Primer prREZ15:   5'-CGGTACCCGCGAATCAAGAAGGTAGGC (SEQ ID NO: 30)
Primer prREZ16:   5'-CGGATCCCGTCTCTGCCGCTTTTTCTT
```

The prREZ15 and prREZ16 primers contained the KpnI and the BamHI sequence, respectively (italicized). The resulting amplicon was digested with BamHI and KpnI and gel purified.

Next, a 1985 bp sequence downstream of *Schizochytrium* ORFC was PCR amplified with the following primers from genomic DNA of *Schizochytrium* sp. ATCC 20888:

```
                                        (SEQ ID NO: 31)
Primer prREZ17: 5'-CGGATCCGAAAGTGAACCTTGTCCTAACCC (SEQ ID NO: 32)
Primer prREZ18: 5'-CTCTAGACAGATCCGCACCATCGGCCG
```

The prREZ17 and prREZ18 primers contained the BamHI sequence and the XbaI sequence, respectively (italicized). The resulting amplicon was digested with BamHI and XbaI and gel purified.

The vector pBluescript SK(+) (Stratagene, acc# X52328) was next digested with KpnI and XbaI and gel purified. This vector and the two amplicons generated above were all ligated simultaneously to produce the vector pREZ22.

The vector pSchizE (Example 1) was then digested with BamHI and treated with mung bean nuclease, column purified, digested with XbaI, and then gel-purified. PCR with the following primers was then performed to generate an amplicon containing the eGFP coding region (using the template pPha-T1-eGFP):

```
Primer 5'eGFP_kpn:
                                        (SEQ ID NO: 33)
5'-GACTGGTACCATGGTGAAGCAAGGGCGAGGAG Primer 3'eGFP_xba:
                                        (SEQ ID NO: 34)
5'-GACTTCTAGATTACTTGTACAGCTCGTCCATGCC
```

This amplicon was then digested with XbaI and ligated to the fragment of pSchizE described above to create the vector pSchizE-eGFP.

PCR was then used with pREZ22 as a template to generate an amplicon encoding the promoter of ORFC. The following primers, each containing a KpnI restriction sequence (shown in italics), were used for this PCR:

```
Primer 5'ORFCproKpn-2:
                                        (SEQ ID NO: 35)
5'-GATCGGTACCGGTGTTCTTTGTTTTGATTTCT Primer 3'ORFCproKpn-2:
                                        (SEQ ID NO: 36)
5'-GATCGGTACCGTCTCTGCCGCTTTTTCTTTA
```

Figure 8:
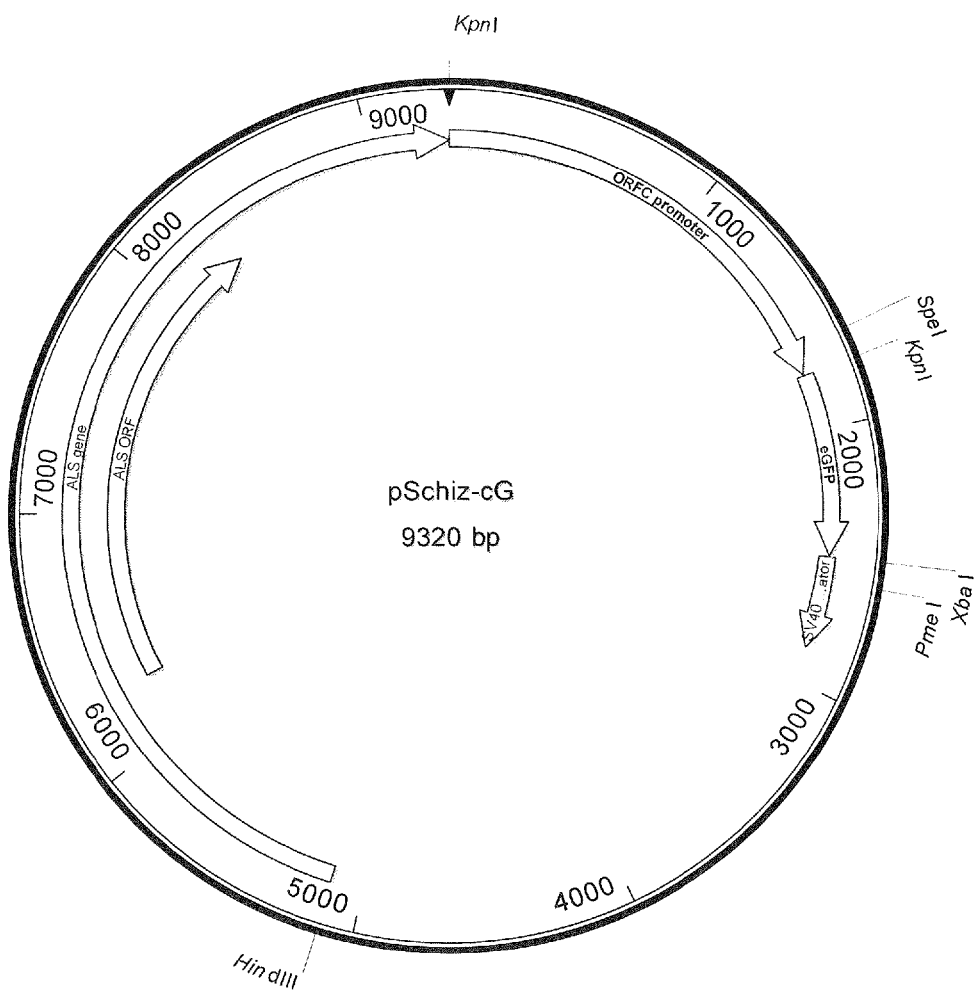
FIG. 8 shows a plasmid map of pSchiz-cG.

This amplicon was then digested with KpnI. The pSchizE-eGFP vector was then also digested with KpnI, generating two fragments. The larger fragment (7554 bp) was gel purified and ligated to the KpnI-digested amplicon above to produce the pSchiz-eG vector, which contained the *Schizochytrium* ORFC promoter sequence followed by the eGFP sequence and an SV40 terminator region (see FIG. 8).

Example 5

Transformation of *Schizochytrium* and Subsequent Protein Expression

Unless indicated otherwise, all vectors and constructs were propagated in *E. coli* UltraMax DH5-α FT chemically competent cells (Invitrogen, Carlsbad, Calif.) for plasmid purification using Qiagen kits appropriate for a given scale of culture (Valencia, Calif.).

Cultures of *Schizochytrium* sp. ATCC number 20888 were grown in M2B medium consisting of 10 g/L glucose, 0.8 g/L $(NH_4)_2SO_4$, 5 g/L $Na_2SO_4$, 2 g/L $MgSO_4.7H_2O$, 0.5 g/L $KH_2PO_4$, 0.5 g/L KCl, 0.1 g/L $CaCl_2.2H_2O$, 0.1 M MES (pH 6.0), 0.1% PB26 metals, and 0.1% PB26 Vitamins (v/v). PB26 vitamins consisted of 50 mg/mL vitamin B12, 100 µg/mL thiamine, and 100 µg/mL Ca-pantothenate. PB26 metals were adjusted to pH 4.5 and consisted of 3 g/L $EeSO_4.7H_2O$, 1 g/L $MnCl_2.4H_2O$, 800 mg/mL $ZnSO_4.7H_2O$, 20 mg/mL $CoCl_2.6H_2O$, 10 mg/mL $Na_2MoO_4.2H_2O$, 600 mg/mL $CuSO_4.5H_2O$, and 800 mg/mL $NiSO_4.6H_2O$. PB26 stock solutions were filter-sterilized separately and added to the broth after autoclaving. Glucose, $KH_2PO_4$, and $CaCl_2.2H_2O$ were each autoclaved separately from the remainder of the broth ingredients before mixing to prevent salt precipitation and carbohydrate caramelizing. All medium ingredients were purchased from Sigma Chemical (St. Louis, Mo.). Cultures of *Schizochytrium* were grown to log phase and transformed with a Biolistic™ particle bombarder (Bio-Rad, Hercules, Calif.) using the vectors pSchiz-E1 (Example 1), pSchiz-sG (Example 2), pSchiz-sGr (Example 3), or pSchiz-cG (Example 4). The Biolistic™ transformation procedure was essentially the same as described previously (see Apt et al., *J. Cell. Sci.* 115(Pt 21):4061-9 (1996) and U.S. Pat. No. 7,001,772). Primary transformants were selected on solid M2B media containing 20 g/L agar (VWR, West Chester, Pa.), 10 µg/mL Sulfometuron methyl (SMM) (Chem Service, Westchester, Pa.) after 2-6 days of incubation at 27° C. All primary transformants were manually transferred to fresh M2B plates with SMM.

Primary transformant colonies were analyzed by fluorescence and light microscopy. Primary transformant colonies were also used to inoculate 50 mL of M2B-SMM liquid media. After incubation at 27° C. for 2-5 days, cultures were harvested by centrifugation at 5500×g for 15 minutes. Cell-free supernatants were concentrated 100-fold using Centriprep™ gravity concentrators (Millipore, Billerica, Mass.) and cell pellets were washed in water and frozen in liquid nitrogen before being resuspended in twice the pellet weight of lysis buffer (consisting of 50 mM sodium phosphate (pH 7.4), 1 mM EDTA, 5% glycerol, and 1 mM fresh Phenylmethylsulphonylfluoride) and twice the pellet weight of 0.5 mm glass beads (Sigma, St. Louis, Mo.). Cell pellet mixtures were then lysed by vortexing at 4° C. in a multi-tube vortexer (VWR, Westchester, Pa.) at maximum speed for 3 hours (h). Cell lysates were then centrifuged at 5500×g for 10 minutes at 4° C. The supernatants were retained and re-centrifuged at 5500×g for 10 minutes at 4° C. The resulting supernatant is defined herein as "cell-free extract." Proteins of both cell-free supernatants and cell-free extracts were quantified with a Bradford assay kit (Sigma, St. Louis, Mo.) and, before loading onto 4-12% polyacrylamide Bis-Tris gels (Bio-Rad, Hercules, Calif.), were boiled as a mixture with XT sample buffer according to the manufacturer's instructions (Bio-Rad, Hercules, Calif.).

SDS-PAGE gels were either stained with Coomassie dye or transferred to PVDF by western blotting. After blotting, PVDF membranes were rinsed with Tris-Buffered saline (TBS) (Sigma, St. Louis, Mo.) and treated with 5% non-fat dry milk (NFDM) in TBS at room temperature for 2 hours. Primary antibodies specific to the protein of interest were diluted in 5% NFDM-TBS according to the manufacturer's instructions. If needed, this solution was removed and replaced with fresh 5% NFDM-TBS to which a secondary antibody, conjugated to alkaline phosphatase and specific to the first, was added. If a secondary antibody was not used, the primary would have been conjugated to alkaline phosphatase. Antibody-treated PVDF was then rinsed with TBS and treated with 5-bromo-4-chloro-3-indoyl-phosphate/nitroblue tetrazolium solution (BCIP/NBT) (KPL, Gaithersburg, Md.).

Figure 9:
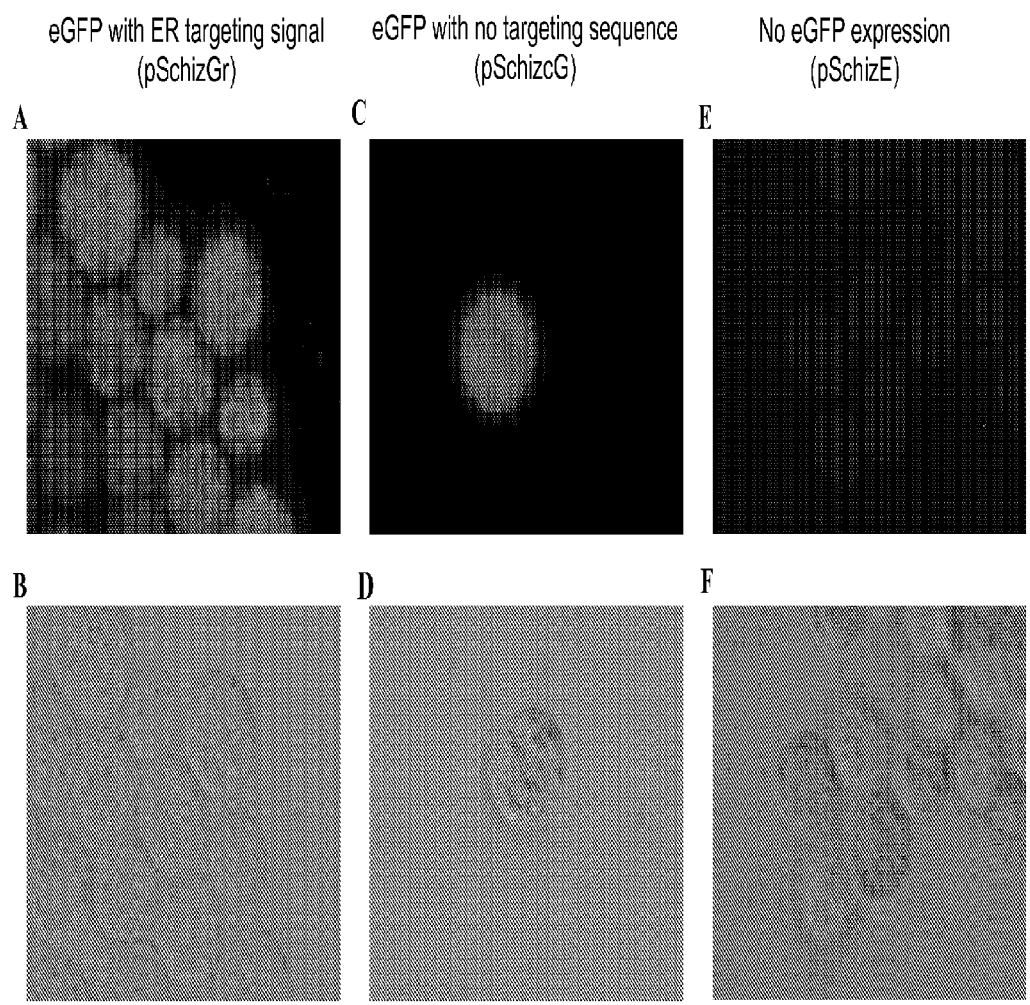
FIG. 9 shows eGFP expression in the cytoplasm and endoplasmic reticulum (ER) of *Schizochytrium* cells.
Figure 10:
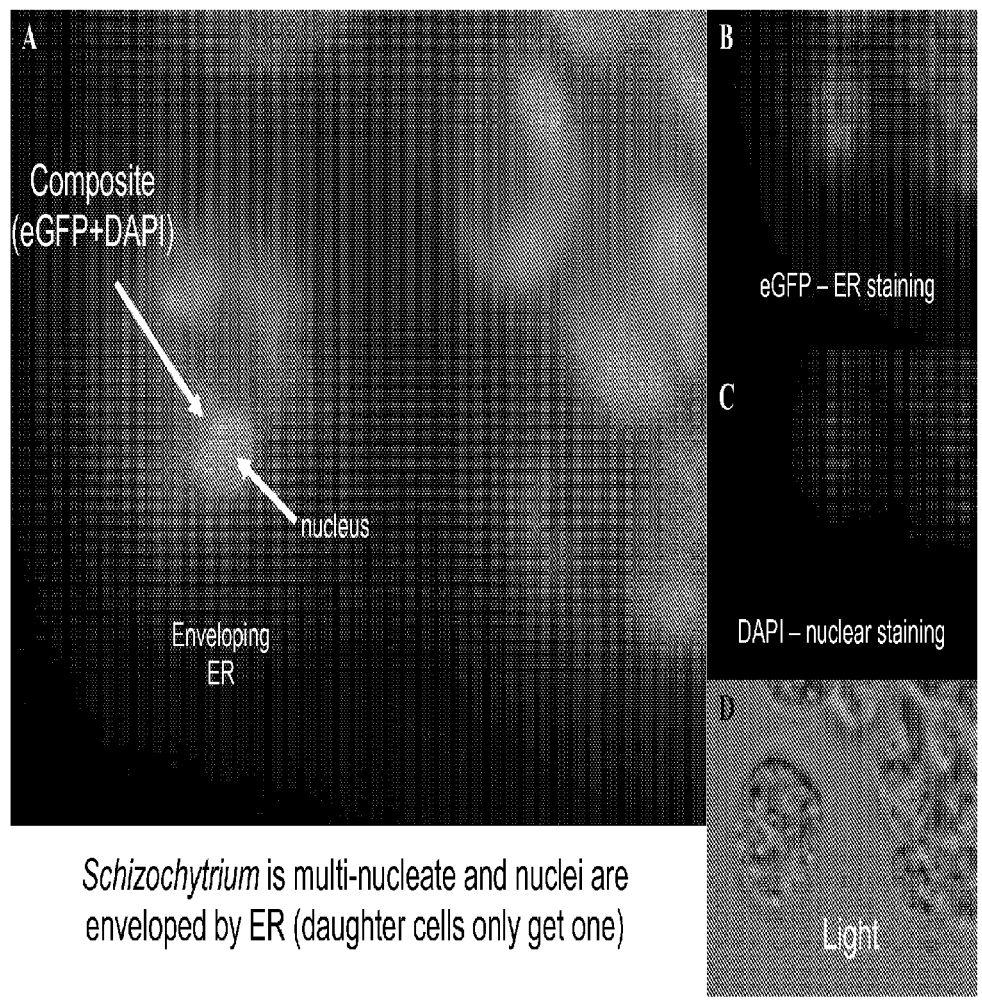
FIG. 10A shows composite fluorescence localization of ER-targeted eGFP and the nucleic acid-specific stain 4',6-diamidino-2-phenylindole (DAPI) in *Schizochytrium* cells transformed with pSchiz-sGr.
FIGS. 10B and 10C show the eGFP—ER staining and DAPI—nuclear staining, respectively, used in making the composite micrograph.
FIG. 10D shows the light micrograph of the same field. As indicated in FIG. 10A, ER membranes envelop each nucleus of a cell, and each cell can contain multiple nuclei. The relevant features of one nucleus in one cell are indicated.
Figure 11:
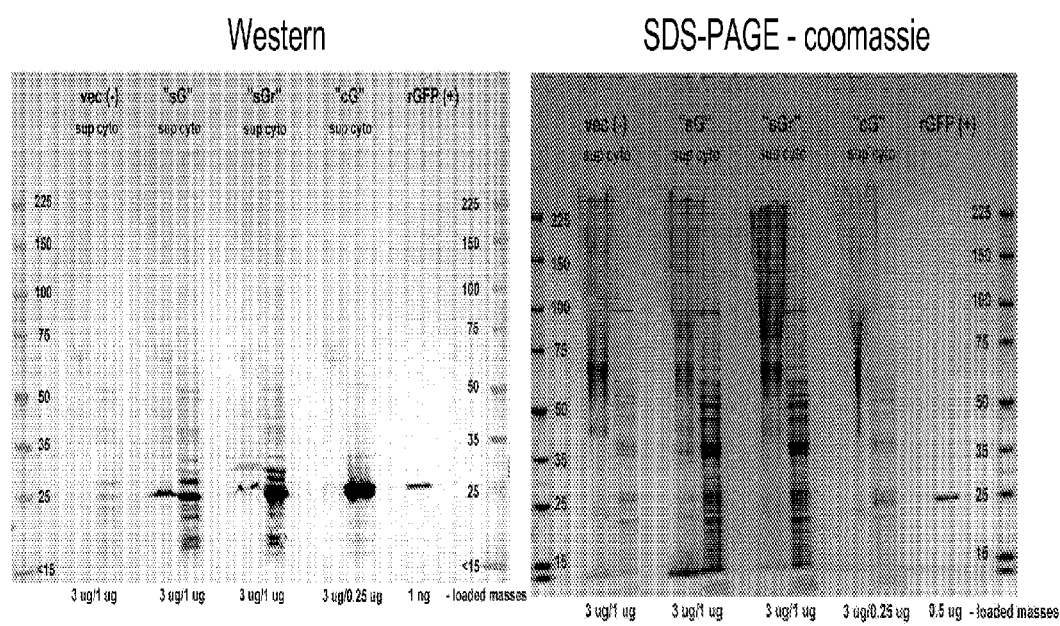
FIG. 11 shows a Western blot and corresponding Coomassie-stained SDS-PAGE gel of cell-free supernatant and cell-free extract samples from four *Schizochytrium* transformant clones. "sup" and "cyto" refer to cell-free supernatants and cell-free extracts, respectively. "sG" refers to samples from cells transformed with pSchiz-sG. "sGr" refers to samples from cells transformed with pSchiz-sGr. "cG" refers to samples from cells transformed with pSchiz-cG. "vec (−)" refers to samples from cells transformed with pSchiz-E10. "GFP (+)" refers to purified recombinant GFP standard (Clontech, Mountain View, Calif.). The gels were loaded with 3 μg of cell-free supernatant protein and 1 μg of cell-free extract protein samples. An empty lane is found between each pair of samples, the recombinant GFP standard, and the molecular weight markers.

As shown in FIG. 9, *Schizochytrium* transformed with pSchizGr exhibited eGFP localization in the ER (see also FIG. 10), while *Schizochytrium* transformed with pSchizcG displayed eGFP throughout the cytoplasm. *Schizochytrium* transformed with pSchizE (empty vector control) displayed no expression of eGFP. As shown in FIG. 11, eGFP was detected in the cell-free supernatant samples (i.e., extracellularly) as well as in the cell-fee extract for *Schizochytrium* transformed with pSchiz-sG. *Schizochytrium* transformed with pSchiz-sGr contained eGFP in the cell-fee extract and, to a lesser extent, in the cell-free supernatant. Finally, *Schizochytrium* transformed with pSchizeG contained eGFP almost exclusively in the cell-fee extract.

Example 6

Identification of Sec1 Signal Peptide

The genome sequence of *Schizochytrium* was previously generated, assembled, and formatted for BLAST searching using industry standard techniques. Supernatant from a culture of *Schizochytrium*, grown under N-replete conditions, was concentrated and run on SDS-PAGE. Major secreted protein bands were excised from the gel and used for amino acid sequencing. By BLAST comparison of the obtained amino acid sequences to the *Schizochytrium* genome (algorithm—tBLASTn, Low Complexity filtering—off, Expect—1000, matrix—PAM30, Ungapped Alignment—on), the corresponding ORF was identified. The 5' portion of the ORF was analyzed using the SignalP algorithm. See, e.g., Bendsten et al., *J. Mol. Biol.* 340: 783-795 (2004); Nielsen and Krogh, *Proc. Int. Conf. Intell. Syst. Mol. Biol.* 6:122-130 (1998); Nielsen et al., *Protein Engineering* 12:3-9 (1999); Emanuelsson et al., *Nature Protocols* 2:953-971 (2007). The 5' region of the Sec1 protein was identified as a secretion signal according to this analysis. See FIG. 12 (comprising SEQ ID NO:37) and FIG. 13 (SEQ ID NO:38).

Example 7

Construction of the *Schizochytrium* Vector pSchiz-Cpt

The pSchiz-Cpt vector contains the OrfC promoter and terminator and the ALS selectable marker. Briefly, this vector was constructed by first digesting the pSchizE plasmid with KpnI/XbaI and gel purifying the resulting 6.89 kb fragment. This digestion also resulted in the removal of the tubulin promoter and most of the polylinker from the pSchizE plasmid; the ALS coding sequence remained intact. Into the resulting 6.8 kb SchizE backbone was ligated a 4 kb KpnI/XbaI fragment containing 2 kb sequence upstream of *Schizochytrium* OrfC plus 2 kb of sequence downstream of *Schizochytrium* OrfC with a BamHI site separating the upstream and downstream segments. The 4 kb KpnI/XbaI fragment was excised from plasmid pREZ22 (see Example 4). The ligation of the 6.8 kb pSchizE backbone and the 4 kb KpnI/XbaI fragment resulted in pSchiz-Cpt.

Example 8

Construction of the *Schizochytrium* Protein Expression Vector pSchizCpt-s1eGFP

Figure 14:
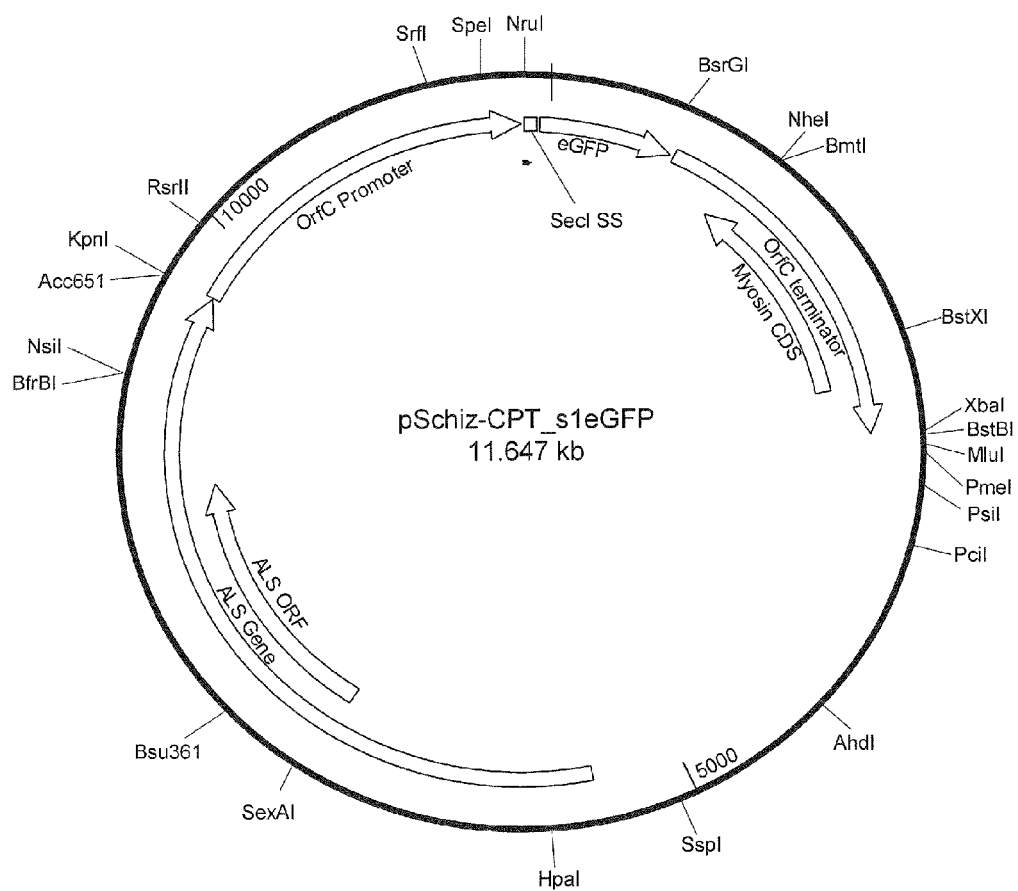
FIG. 14 shows a plasmid map of pSchiz-Cpt-sleGFP, also termed pCL0001.

The pSchizCpt-s1eGFP plasmid comprises a *Schizochytrium* OrfC promoter, a Sect signal sequence preceding a sequence encoding eGFP, and OrfC terminator and a mutated *Schizochytrium* ALS selectable marker sequence. See FIG. 14. This plasmid is also termed pCL0001 and was deposited at the American Type Culture Collection, Patent Depository, 10801 University Boulevard, Manassas, Va. 20110-2209, on Nov. 18, 2008 and given ATCC Accession No. PTA-9615.

Example 9

Expression and Secretion of eGFP by *Schizochytrium* in Fermentors

Cells of *Schizochytrium* were transformed with pSchizCpt-s1eGFP (see Example 8) as described in Example 5. Cell lines resistant to SMM were isolated on M2B agar plates and transferred into M2B liquid culture (containing 10 µg/ml SMM) in shake flasks and incubated at 27.5° C. with shaking at 150 rpm. After cultivation for 72-168 h cultures were harvested by centrifugation (5000×g for 10 min) and the cell-free supernatant concentrated (approximately 250 fold) using Centriprep and Microcon concentrators (MWCO 10000). Samples (1-7 µl) were run on SDS-PAGE and the separated proteins transferred onto PVDF membrane. The blocked and washed membranes were probed with rabbit anti-eGFP IgG (Biovision) and reacting protein bands were visualized by probing with an alkaline phosphatase conjugated goat anti-rabbit IgG (fc) (Promega) and treatment with BCIP/NBT reagent. Cell lines expressing the highest amount of eGFP were selected.

One of the high producing cell lines was cultivated in 2.0 L (working volume) fermentors. Baffled inoculum flasks contained 150 ml of HD1 medium and were incubated at 29.5° C. for 24-48 h with shaking at 200 rpm. The inoculum culture was used to inoculate the fermentor containing: 50 g/L glucose, 13.62 g/L $Na_2SO_4$, 0.72 g/L $K_2SO_4$, 0.56 g/L KCl, 2.27 g/L $MgSO_4.7H_2O$, 1.8 g/L $KH_2PO_4$, 17.5 g/L $(NH_4)_2SO_4$, 0.19 g/L $CaCl_2.2H_2O$, 51.5 mg $FeSO_4.7H_2O$, 3.1 g/L $MnCl_2.4H_2O$, 6.2 g/L $ZnSO_4.7H_2O$, 0.04 mg $CoCl_2.6H_2O$, 0.04 mg $Na_2MoO_4$, 2.07 g/L $CuSO_4.5H_2O$, 2.07 g/L $NiSO_4.6H_2O$, 9.75 mg thiamine, 0.16 mg vitamin B12, and 3.33 mg calcium pantothenate. During cultivation the temperature was 29.5° C., the $dO_2$% was controlled at 20%, the glucose concentration was maintained at between 15-20 g/L once the initial level fell within this range and the pH was maintained at 6.5. Samples were aseptically removed at intervals for analysis.

Figure 15:
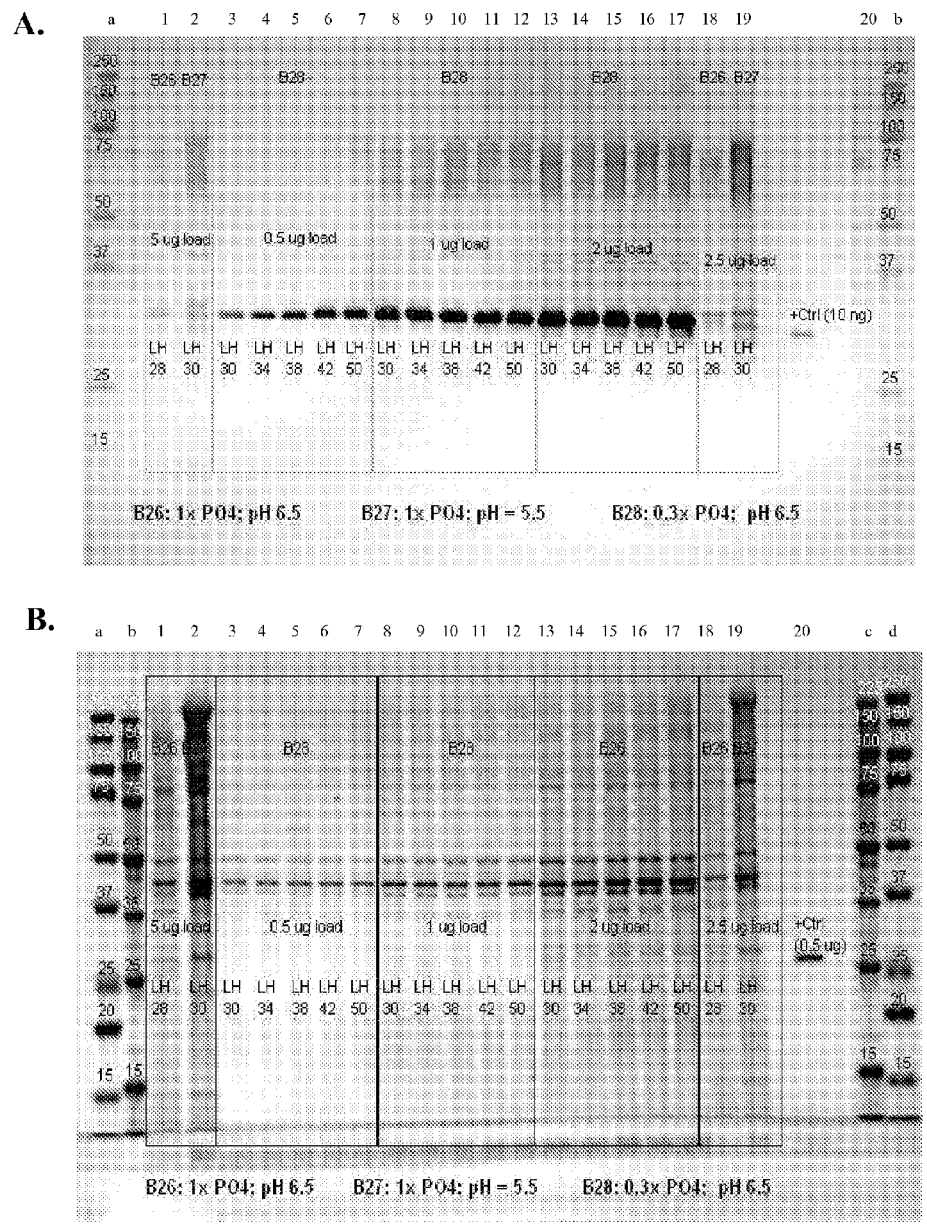
FIG. 15A shows a Western blot for secreted eGFP protein and FIG. 15B shows a corresponding Coomassie-stained SDS-PAGE gel from three cultures of *Schizochytrium* grown under different fermentation conditions ("B26," "B27," or "B28" fermentation conditions, as defined in FIG. 15). Lanes 1-19 were loaded with the indicated amounts of protein. LH=fermentation time in hours. Lane 20 in FIG. 15A was loaded with 10 ng and lane 20 in FIG. 15B was loaded with 0.5 μg of a purified recombinant GFP standard; the eGFP bands from *Schizochytrium* are slightly larger than the control band because they contain a linker sequence.

Unconcentrated samples of cell-free supernatants (containing 0.5-5.0 µg total protein) were separated by SDS-PAGE and the proteins transferred to PVDF membrane. Blocked and washed membranes were probed for secreted eGFP as described above. See FIG. 15.

Example 10

Figure 16:
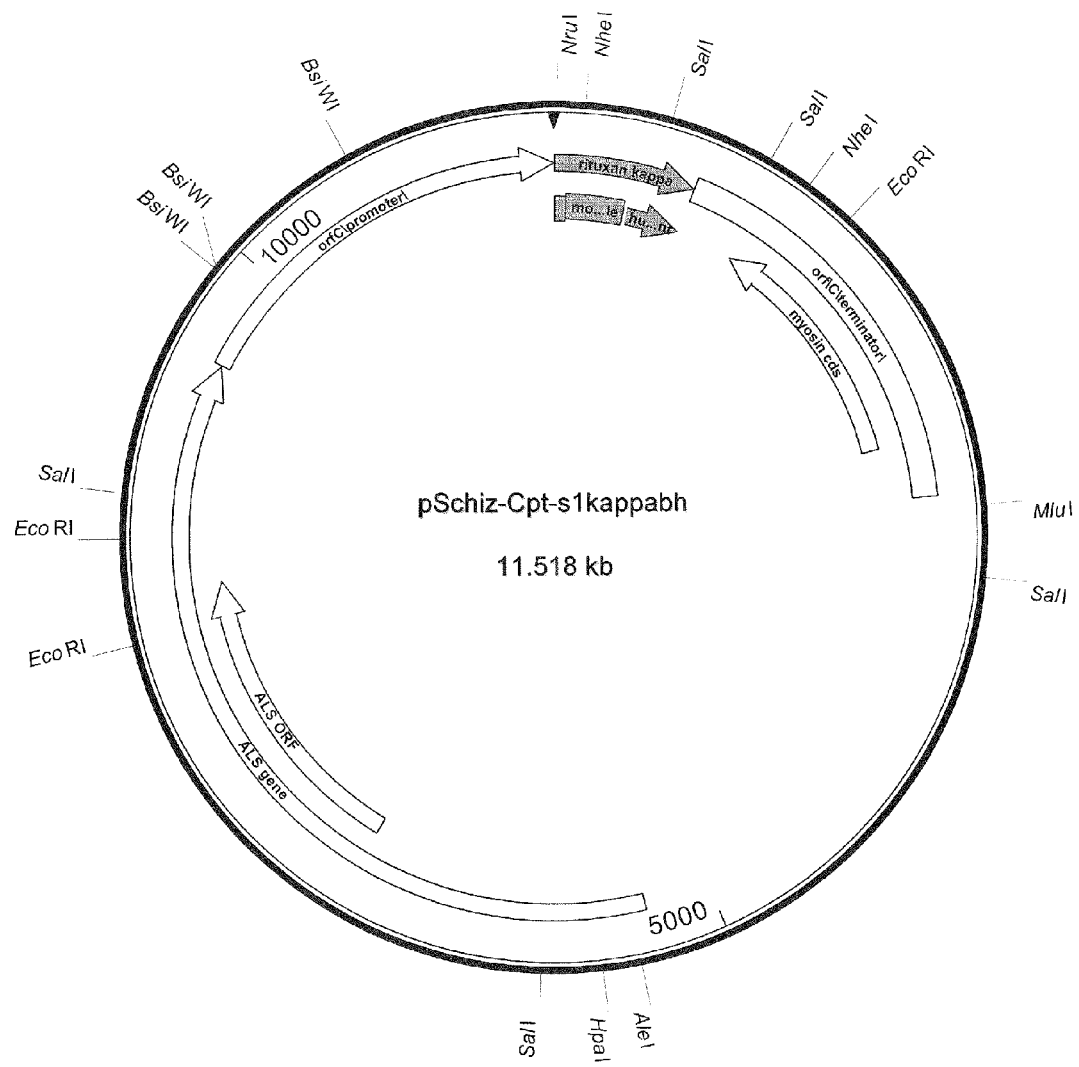
FIG. 16 shows a plasmid map of pSchiz-Cpt-slkappabh.

Construction of the *Schizochytrium* Protein Expression Vector pSchizCpt-s1kappabh The pSchizCpt-s1kappabh plasmid comprises a *Schizochytrium* OrfC promoter, a Sec1 signal sequence preceding a polynucleotide sequence encoding an IgG kappa subunit, and OrfC terminator region and a mutated *Schizochytrium* ALS selectable marker sequence (see FIG. 16). The expression vector was made as follows:

The resynthesized (codon-optimized) gene encoding the kappa chain of an IgG, produced from the corresponding amino acid sequence by Blue Heron Biotechnologies using the codon usage table of FIG. 42, with a 5' Sec1 secretion signal sequence was cloned into the plasmid pSchiz-Cpt between the orfC promoter and the orfC terminator. Briefly, the vector pSchiz-Cpt was digested with BamHI and alkaline phosphatase according the enzyme manufacturer's instruction (New England Biolabs). This was ligated to an amplicon digested with BglII (NEB) and which was created using the following primers:

```
Primer 5'ss-X Bgl long:
                                        (SEQ ID NO: 39)
GACTagatctATGAAGTTCGCGACCTCG Primer 3'ritx_kap_bh_Bgl:
                                        (SEQ ID NO: 40)
gactagatctTCAGCACTCACCGCGGTTAAAGG
``` and a template provided by Blue Heron Biotechnologies which harbored a synthetic optimized DNA molecule containing the polynucleotide sequence for the Sec1 signal peptide followed by the kappa polynucleotide sequence (SEQ ID NO:41). Resulting bacterial transformant colonies were screened for vector inserts, appropriately aligned for expression. One clone (designated pSchizCPT-s1kappabh) was picked for further analysis, confirmation of sequence, and for transformation of *Schizochytrium*.

Example 11

Expression and Secretion of Antibody Subunit Kappa by *Schizochytrium*

Generation of Transformant Cell Lines

*Schizochytrium* sp. ATCC 20888 was cultivated in 250 ml shake flasks containing 50 ml of M2B medium at 27° C. for 24 h. The absorbance was measured at 600 nm and a volume equivalent to 1 ml of a culture with an absorbance value of 1 was centrifuged at 8,000×g for 5 min. The cell pellet was suspended in 100 µl of M2B and spread on a M2B agar plate in a 2 cm diameter circle.

The area of plate containing the spread *Schizochytrium* cells was bombarded with pSchizCptS1kappa (linearized with XbaI) coated M10 beads at a pressure of 1100 Psi.

After bombardment, the M2B plate was incubated for 16 h at 27° C. and colonies growing in the center of the *Schizochytrium* spread plate picked and spread on M2B plates containing 10 µg/ml SMM. After 24 to 72 h, twenty colonies were picked and inoculated into 5 ml M2B containing 10 mg/ml SMM in a 25 ml culture tube. The culture tubes were incubated at 27° C. at 135 rpm for 72 h.

Detection of Kappa Expression

Ten of the most turbid shake flask cultures from above were selected for expression analysis. 50 ml of M2B containing 10 µg/ml SMM in 250 ml flasks were inoculated with 0.5 ml from a tube culture. The cultures were incubated at 27° C. with shaking at 135 rpm for 24 hours, after which the cell pellet and cell-free supernatant were separated by centrifugation at 5500×g for 10 min.

The cell pellet was suspended in 40 ml $dH_2O$, centrifuged at 5500×g for 10 min then suspended in twice its wet weight of extraction buffer. Twice the pellet wet weight of glass beads were added and the tubes shaken for 3 hours at 4° C. The resulting cell homogenate was centrifuged at 5000×g for 10 min and the supernatant retained as the cell-free extract.

The cell-free supernatant was concentrated from approx 50 ml to >200 µl using Centriprep and Microcon concentrators (Amicon) with a 10000 MW cut off.

3 µg of protein (cell-fee extract and concentrated cell-free supernatant) for each selected transformant were run on 4-12% Bis Tris SDS PAGE (xt criterion, BioRad) with MOPS running buffer at 200 V for approximately 45 min (until the dye front had just run off bottom of gel). Protein bands were transferred to PVDF membrane using Nupage transfer buffer at 70 V for 90 min. Membranes were blocked with 5% (w/v) milk powder, in TBS containing 0.1% Tween 20 and antibody subunit kappa was localized via a Western Blot using alkaline phosphatase conjugated anti-human kappa IgG (Sigma). Positive bands were visualized with BCIP/NBT Phosphatase Substrate (KPL).

Figure 17:
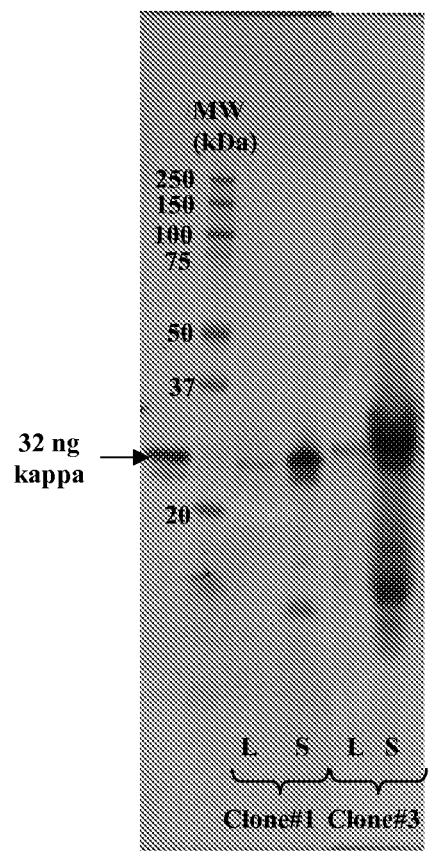
FIG. 17 shows a Western blot for secretion of a kappa antibody subunit by *Schizochytrium*. L=cell-free extract; S=cell-free supernatant.

Antibody subunit kappa was clearly detectable predominantly in the cell-free supernatants from shake flask cultures cultivated as described above (see FIG. 17). Appearance of the kappa protein in the cell-free supernatant and with a MW indistinguishable from the authentic kappa standard was consistent with the kappa subunit being secreted and undergoing appropriate post-translational modification (cleavage of the Sec1 secretion signal).

Example 12

Expression of Antibody Subunit Kappa by *Schizochytrium* in Fermentors

Cultivation

The two clones (1 and 3) that appeared to express the highest amount of extra-cellular kappa subunit were cultivated in 2.0 L (working volume) fermentors. Baffled inoculum flasks contained 150 ml of HD1 medium and were incubated at 29.5° C. for 24-48 hours with shaking at 200 rpm. The inoculum culture was used to inoculate the fermentor containing: 50 g/L glucose, 13.62 g/L Na$_2$SO$_4$, 0.72 g/L K$_2$SO$_4$, 0.56 g/L KCl, 2.27 g/L MgSO$_4$.7H$_2$O, 1.8 g/L KH$_2$PO$_4$, 17.5 g/L (NH$_4$)$_2$SO$_4$, 0.19 g/L CaCl$_2$.2H$_2$O, 51.5 mg FeSO$_4$.7H$_2$O, 3.1 g/L MnCl$_2$.4H$_2$O, 6.2 g/L ZnSO$_4$.7H$_2$O, 0.04 mg CoCl$_2$.6H$_2$O, 0.04 mg Na$_2$MoO$_4$, 2.07 g/L CuSO$_4$.5H$_2$O, 2.07 g/L NiSO$_4$.6H$_2$O, 9.75 mg thiamine, 0.16 mg vitamin B12, and 3.33 mg calcium pantothenate. During cultivation the temperature was 29.5° C., the dO$_2$% was controlled at 20%, the glucose concentration was maintained at between 15-20 g/L once the initial level fell within this range and the pH was maintained at 6.5. Samples were aseptically removed at intervals for analysis.

Detection of Kappa Expression

Cell-free supernatants were analyzed without concentration, the total protein was determined using the method of Bradford (Sigma Bradford Reagent) with BSA as a protein standard. Western analysis to confirm kappa subunit expression was carried out as described for the shake flask cultures above.

Figure 18:
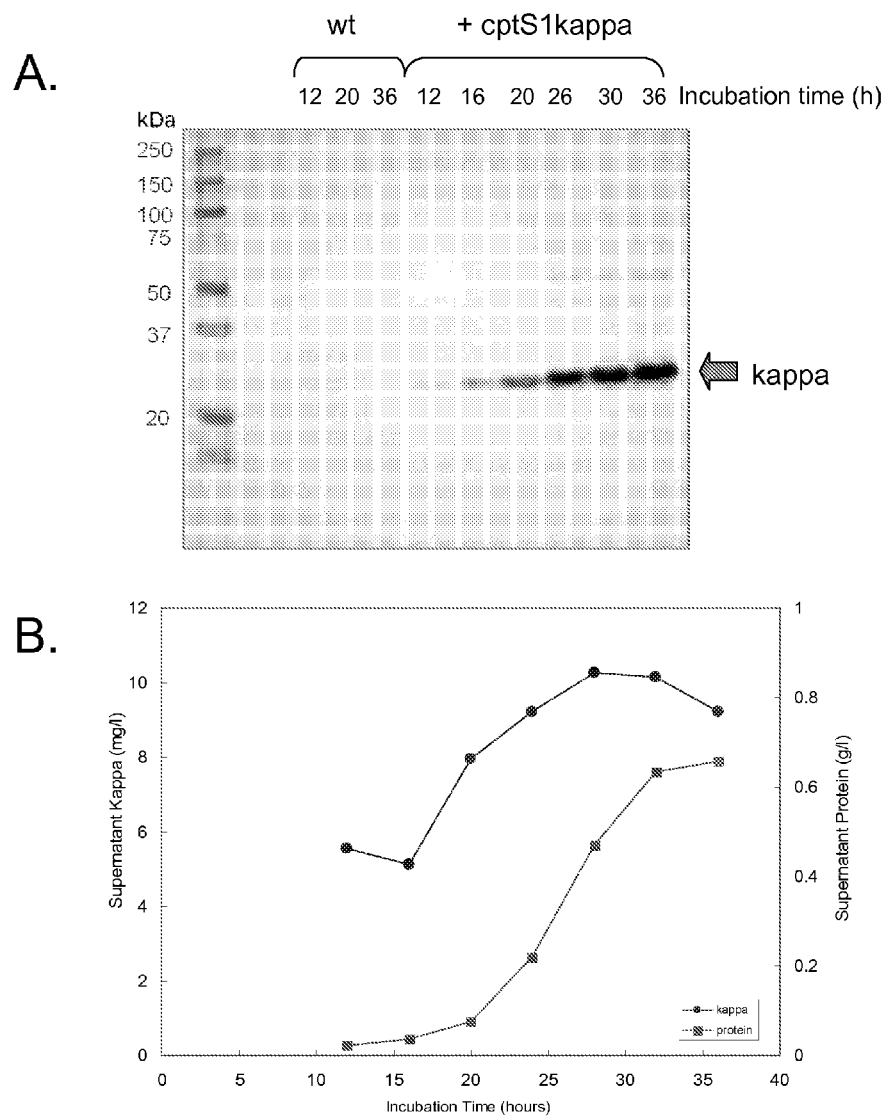
FIG. 18A shows a Western blot for expression of the kappa antibody subunit. The incubation time at which the culture supernatant sample was obtained is indicated at the top of FIG. 18A. "wt" refers to "wild-type" (i.e., non-transformed) *Schizochytrium*. "+cptS1kappa" refers to *Schizochytrium* transformed with a vector containing a codon-optimized gene encoding a human kappa antibody fragment, an ORFC promoter and terminator, and a sequence encoding a Sec1 signal peptide.
FIG. 18B shows the accumulation of total protein (assayed according to Bradford) and antibody chain kappa (assayed via ELISA) in the culture supernatant of *Schizochytrium* transformed with cptS1kappa.

Quantification of kappa expression was carried out using a Human Kappa-B+F Elisa Quantification Kit (Bethyl Laboratories Inc.) and a Fluoro Omega plate reader (BMG Labtech), both according to manufacturer's instructions. See FIG. 18.

Example 13

Construction of the pAB0011 Expression Vector

Using gDNA extracted from *Schizochytrium* sp. ATCC 20888 as a template, PCRs were conducted with the following primers to create an amplicon 2015 bp in length:

```
                                     (SEQ ID NO: 47)
5' 60S-807:      TCGATTTGCGGATACTTGCTCACA (SEQ ID NO: 48)
3' 60S-2821:     GACGACCTCGCCCTTGGACAC
```

The amplicon was gel purified and used as a template for subsequent PCR with the following primers:

```
5' 60Sp-1302-Kpn:
                                     (SEQ ID NO: 49)
GACTggtaccTTTTTCCGCTCTGCATAATCCTAA 3' 60Sp-Bam:
                                     (SEQ ID NO: 50)
GACTggatccTTGGCTTTTTCTTTCTTGTTGC
```

Figure 24:
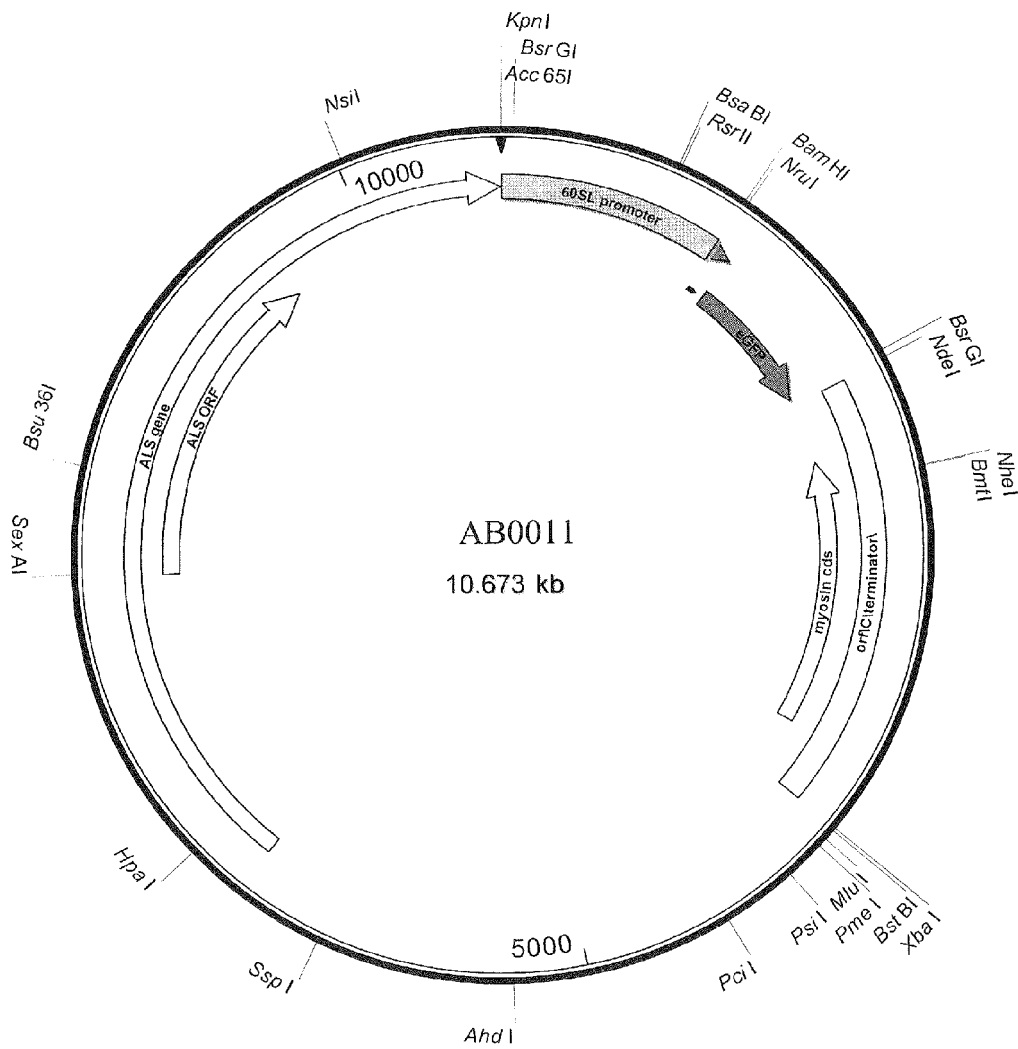
FIG. 24 shows a plasmid map of pAB0011.

The resulting 1017 bp amplicon was purified, digested with KpnI and BamHI, and ligated to pSchiz-CPT(+)-s1GFP(6h), which had been previously purified and digested with KpnI and BamHI. Ligation products were used to transform *E. coli*, and plasmids were purified and screened by restriction digests from resulting colonies. One plasmid clone (#4.1), with the expected restriction digest pattern and including the 60S long promoter, was verified by Sanger sequencing and designated pAB0011 for transformations of *Schizochytrium*. See FIG. 24. The vector pAB0011 was deposited at the American Type Culture Collection, Patent Depository, 10801 University Boulevard, Manassas, Va. 20110-2209, on Nov. 18, 2008, and given ATCC Accession No. PTA-9614.

Example 14

Construction of the pAB0018 Expression Vector

Using gDNA extracted from *Schizochytrium* sp. ATCC 20888 as a template, PCRs were conducted with the following primers to create an amplicon 2268 bp in length:

```
                                     (SEQ ID NO: 51)
5' EF1-68:       CGCCGTTGACCGCCGCTTGACTCT (SEQ ID NO: 52)
3' EF1-2312:     CGGGGGTAGCCTCGGGGATGGACT
```

This amplicon was gel purified and used as a template for subsequent PCR with the following primers:

```
5' EF1-54-Kpn:
                                     (SEQ ID NO: 53)
GACTggtaccTCTTATCTGCCTCGCGCCGTTGAC 3' EF1-1114-Bam:
                                     (SEQ ID NO: 54)
GACTggatccCTTGCTTGCTAGTAGTCGCTTTCGAAC
```

Figure 25:
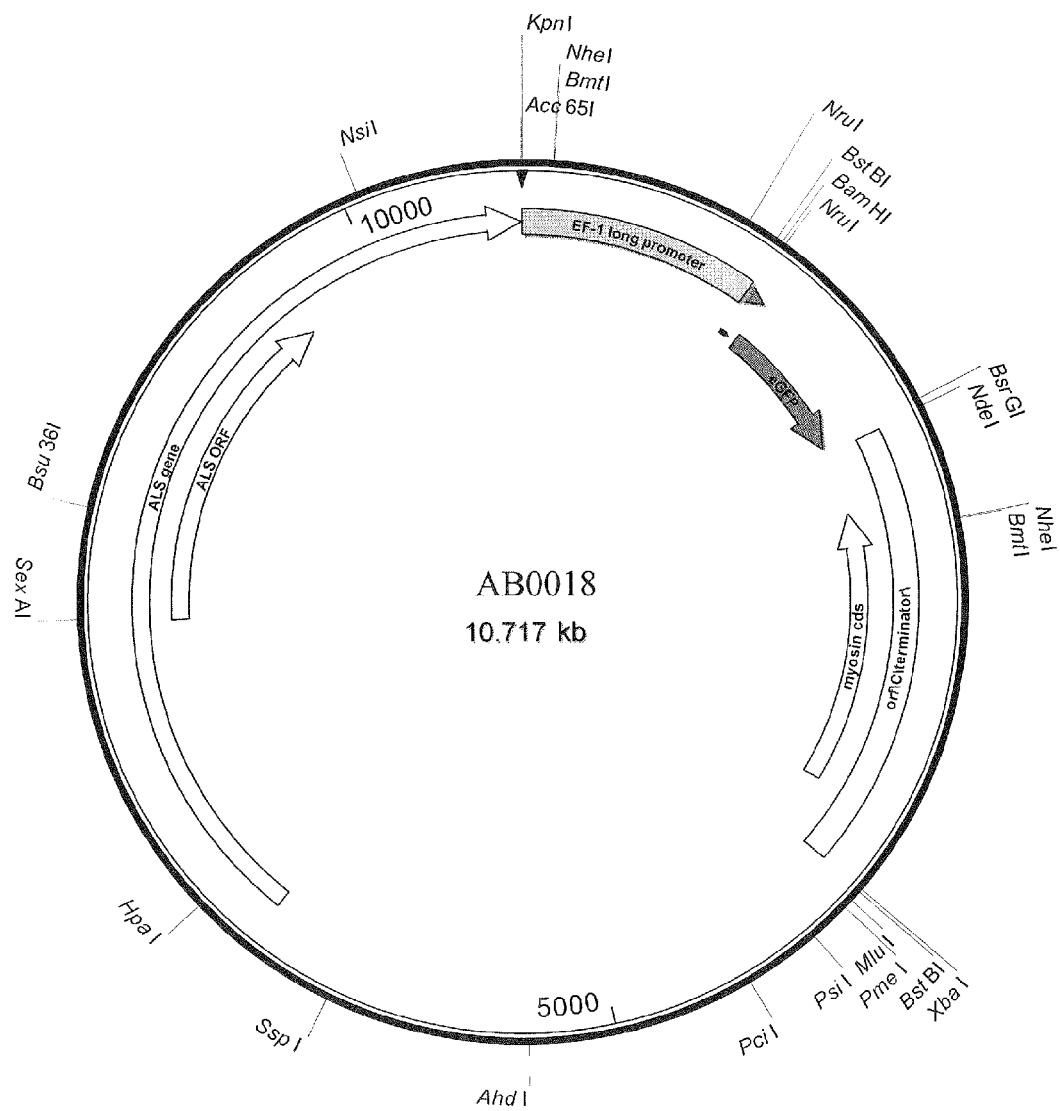
FIG. 25 shows a plasmid map of pAB0018.

The resulting 1060 bp amplicon was purified, digested with KpnI and BamHI, and ligated to pSchiz-CPT(+)-s1GFP(6h), which had been previously purified and digested with KpnI and BamHI. Ligation products were used to transform *E. coli*, and plasmids were purified and screened by restriction digests from resulting colonies. One plasmid clone (#6.1), with the expected restriction digest pattern and containing the EF-1 long promoter, was verified by Sanger sequencing and designated pAB0018 for transformations of *Schizochytrium*. See FIG. 25. The vector pAB0018 was deposited at the American Type Culture Collection, Patent Depository, 10801 University Boulevard, Manassas, Va. 20110-2209, on Nov. 18, 2008, and given ATCC Accession No. PTA-9616.

Example 15

Construction of the pAB0022 Expression Vector

Cell-free supernatants of *Schizochytrium* cultures were analyzed by SDS-PAGE and from this a single protein band, designated Sec1p (for Sec1 protein), was selected for purification to homogeneity. Peptide fragment sequences of this protein were identified using mass spectroscopic techniques and correlated to conceptual translations of a *Schizochytrium* whole genome sequence using BLAST algorithms (tBLASTn, Ungapped alignment, low complexity filtering OFF, Expect=10000, Matrix=PAM30) (ftp://ncbi.nlm.nih.gov/blast). One open reading frame encoding all of the peptide sequences was identified and designated Sec1g (for Sec1 gene). Putative promoter sequences, upstream of the start ATG were also identified and synthesized (Blue Heron Biotechnologies). A vector containing the synthetic Sec1 g promoter was used as a template for PCR with the following primers:

```
                                     (SEQ ID NO: 55)
5' Sec1P-kpn:    GACTggtaccCCGTCCTTGACGCCTTCGC (SEQ ID NO: 56)
3' Sec1P-bam:    GACTggatccGATGAGTAATGGACGATCTTC
```

Figure 26:
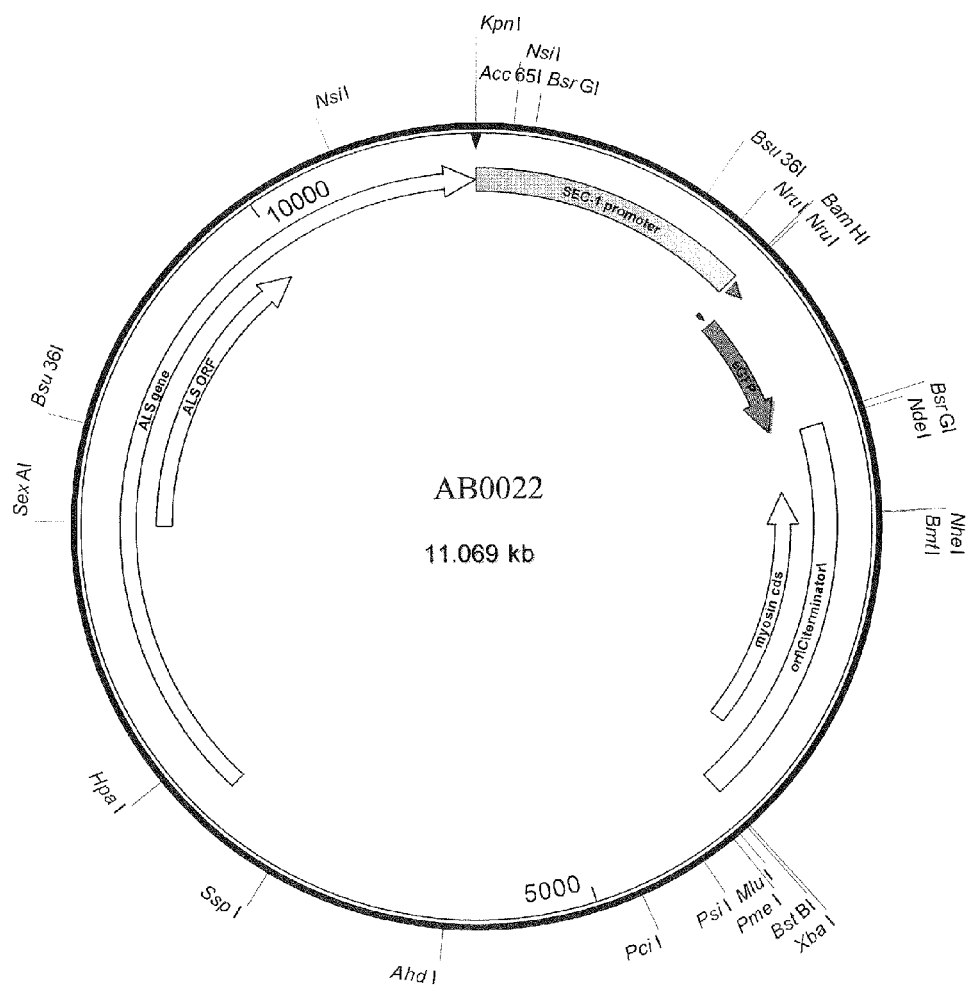
FIG. 26 shows a plasmid map of pAB0022.

The resulting 1438 bp amplicon was purified, digested with KpnI and BamHI, and ligated to pSchiz-CPT(+)-s1GFP(6h), which had been previously purified and digested with KpnI and BamHI. Ligation products were used to transform *E. coli*, and plasmids were purified and screened by restriction digests from resulting colonies. One plasmid clone (#8.1), with the expected restriction digest pattern and containing the Sec1 promoter, was verified by Sanger sequencing and designated pAB0022 for transformations of *Schizochytrium*. See FIG. 26. The vector pAB0022 was deposited at the American Type Culture Collection, Patent Depository, 10801 University Boulevard, Manassas, Va. 20110-2209, on Nov. 18, 2008, and given ATCC Accession No. PTA-9613.

Example 16

Transcription of Heterologous Genes

Promoters for genes encoding Elongation Factor 1 (EF1) and the 60S ribosomal unit were selected as promoters for the transcription of heterologous genes in *Schizochytrium*. The genome sequence of *Schizochytrium* was searched and genes showing homology with published sequences for both genes were identified. Two versions (one short and one long) for each promoter were cloned via PCR.

The promoter driving expression of the SEC1 gene was also selected as a promoter for transcription of heterologous genes in *Schizochytrium*. Because the SEC1 gene encodes the only native secreted and glycosylated protein so far identified in *Schizochytrium* cultures, this promoter could time expression of heterologous proteins to the growth phase most suitable for the production of secreted glycosylated proteins.

The vector cpt(+), containing the S1eGFP construct (i.e., the eGFP gene with the SEC1 secretion signal at the N-terminus, expression driven by the OrfC promoter—vector CL0001) was modified to excise the OrfC promoter and replace this element with one of the following sequences:

EF1 promoter (short version)=EF1-S from vector AB0015
EF1 promoter (long version)=EF1-L from vector AB0018
60S promoter (short version)=60S-S from vector AB0010
60S promoter (long version)=60S-L from vector AB0011
SEC1 promoter=Sec1 from vector AB0022

*Schizochytrium* sp. 20888 was transformed with each of the 5 vectors via particle bombardment as previously described. Ten viable cell lines for each transformation were selected at random for analysis. Transformation with CL0001 was carried out as a control for each of the 5 vectors. Five viable cells lines for transformation with CL0001 were selected at random for analysis.

Transformant cell lines were cultivated in 250 ml shake flasks containing 50 ml M2B for 72 h at 29.5° C. with continuous shaking at 200 rpm. The biomass was removed by centrifugation at 5000×g for 10 min, and the cell-free supernatant was concentrated to ≈1 ml using Centriprep concentrators (MWCO 10000). The protein concentration of the cell-free supernatant samples was measured using the method of Bradford.

Aliquots of cell-free supernatants were separated on SDS acrylamide gels (XT Criterion) under reducing conditions and the separated protein bands were transferred onto PVDF membrane. eGFP was detected using an AP-conjugated anti-eGFP antibody and visualized using NCIP/NBT Reagent.

The maximum amount of concentrated supernatant (7 μl) was separated in each lane to determine which of the cell lines expressed and secreted eGFP (Table 1). Although the level of eGFP expression varied between promoters and between cell lines for individual promoters, 33 cell lines (from the 55 cell lines analyzed for the 6 promoters compared) were shown to express eGFP (data not shown).

TABLE 1

Number of cell lines from each transformation expressing detectable quantities of secreted eGFP

| Promoter | OrfC (CL0001) | EF1-S AB0015 | EF1-L AB0018 | 60S-S AB0010 | 60S-L AB0011 | SEC1 AB0022 |
|---|---|---|---|---|---|---|
| # expressing eGFP/total # analyzed | 2/5 | 6/10 | 5/10 | 6/10 | 6/10 | 8/10 |

While not all cell lines expressed secreted eGFP, at least approximately half of the cell lines did produce detectable levels of eGFP and each promoter was capable of directing expression of eGFP.

Figure 27:
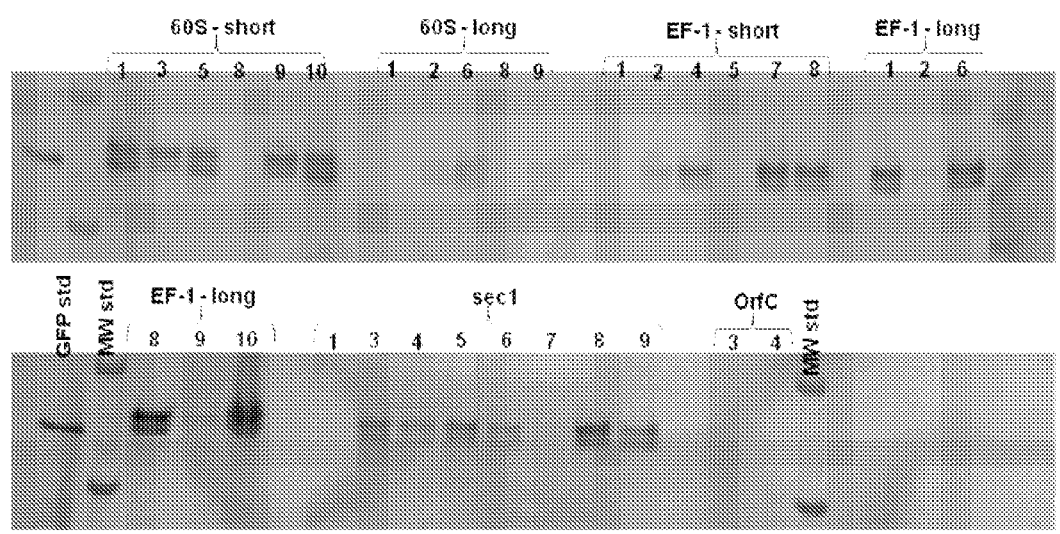
FIG. 27 shows a Western blot for eGFP in cell-free supernatant samples taken from cultures of *Schizochytrium* transformed with expression vectors containing the eGFP gene driven by the EF1 promoter (short version), EF1 promoter (long version), 60S promoter (short version), 60S promoter (long version), SEC1 promoter, and OrfC promoter, respectively.

The cell lines that were found to express and secrete eGFP were further analyzed in order to compare the relative promoter strengths. Proteins from the cell-free supernatant of each culture determined to express eGFP were loaded onto SDS acrylamide gels and were normalized to 1 μg per lane. The proteins were separated by electrophoresis, and the separated proteins were transferred to PVDF membrane and probed for eGFP using the AP conjugated anti-eGFP antibody as described above. See FIG. 27. The amounts of supernatant protein loaded in the initial screen for eGFP was approximately ten-fold greater than used in the experiment that generated FIG. 27. As such, the heterologous eGFP protein is not apparent in all lanes of FIG. 27 as it was below the level of detection for some samples at the protein levels loaded for the experiment. At a loading of 1 μg protein/lane, the expression of secreted eGFP from the OrfC promoter was below detectable limits. However, the expression/secretion of eGFP driven by all of the other promoters was detectable in at least some of the cell lines generated. This demonstrated that all of the selected promoters, EF1, 60S, and SEC1, were "strong" promoters in comparison with the OrfC promoter. In particular, the expression of secreted eGFP in certain cell lines from the EF1-L transformants was visibly greater than for any of the other promoter constructs, indicating that this promoter was the strongest of the promoters tested.

Figure 28:
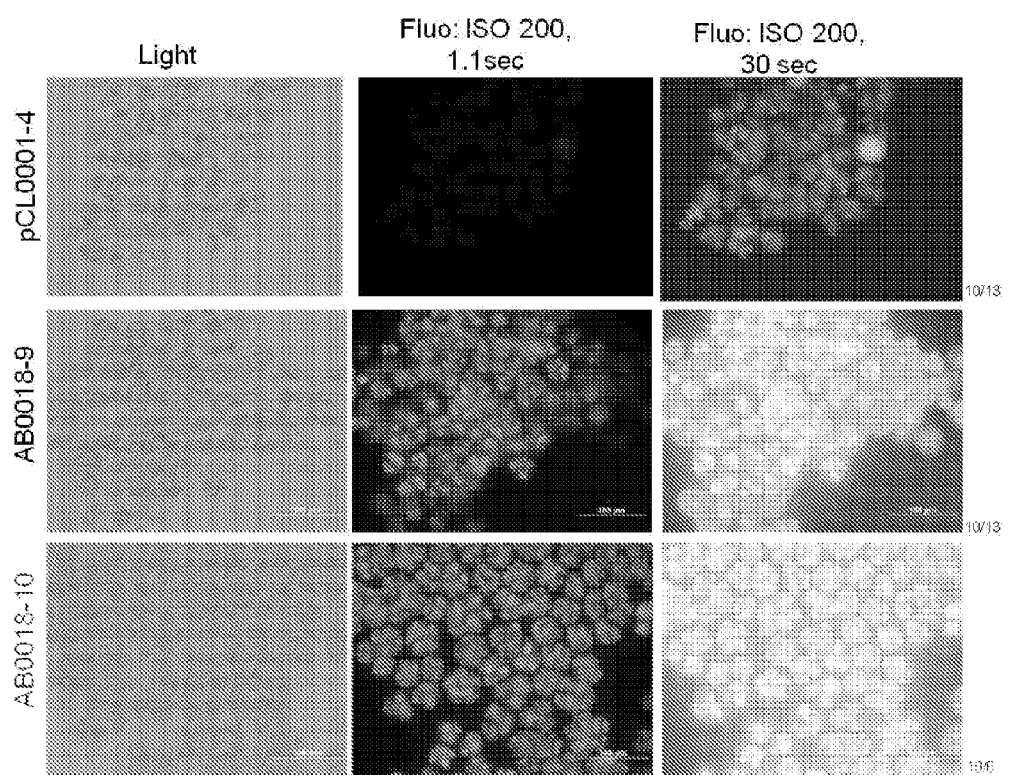
FIG. 28 shows fluorescence microscopy of transformant cell lines associated with eGFP expression driven by either the OrfC promoter (pCL0001-4) or the EFI-L promoter (AB0018-9 and -10).

Confirmation of the strength of the EF1-L promoter was obtained by observing the expression in the EF1-L transformant cell lines AB0018-9 and AB0018-10 in comparison with a typical OrfC transformant, CL0001-4, under fluorescence microscopy. See FIG. 28. Whereas the CL0001-4 cell line exhibited modest fluorescence (Fluo:ISO 200 1.1 sec panes) the AB0018-9 and AB0018-10 cell lines exhibited pronounced fluorescence, indicating substantial accumulation of intracellular eGFP.

Example 17

Glycosylation Profiles in *Schizochytrium*

Figure 29:
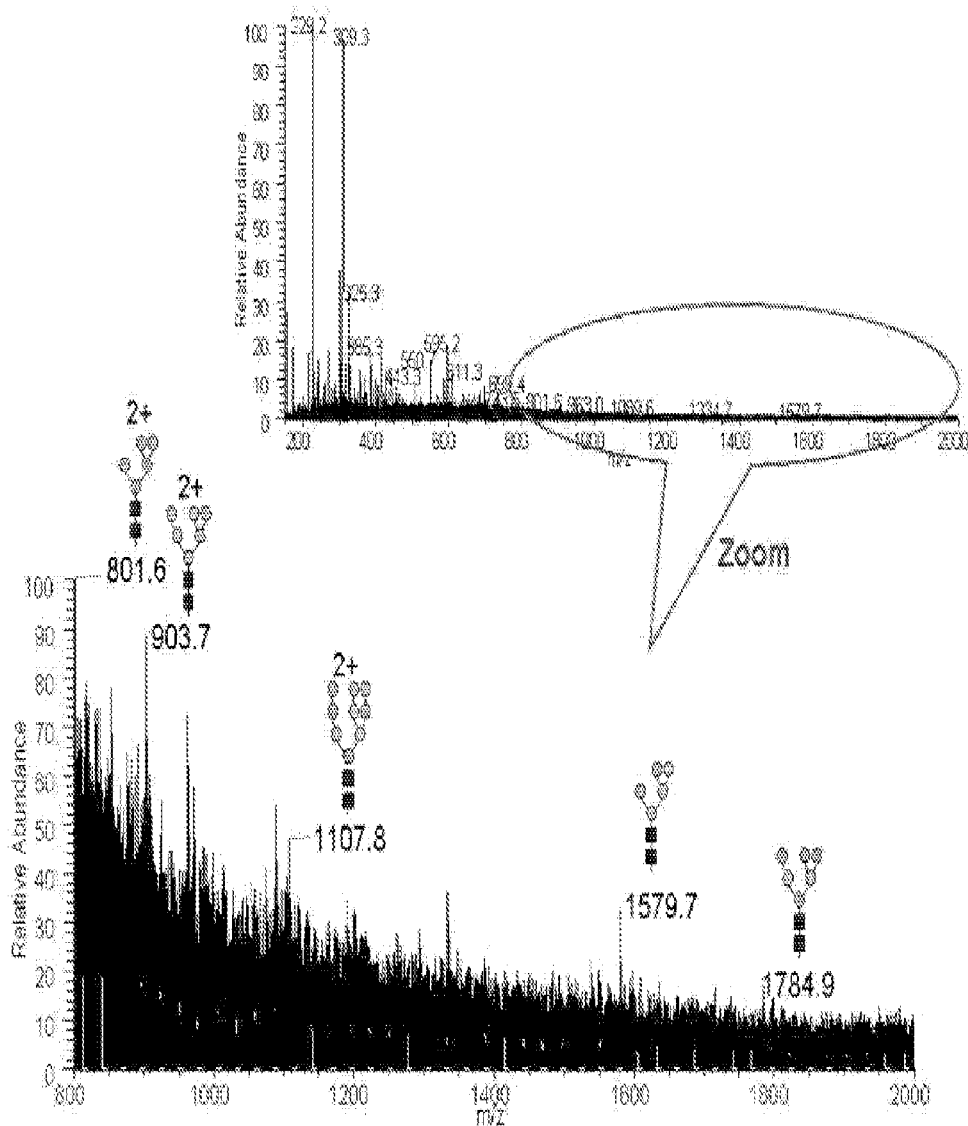
FIG. 29 shows N-glycan structures detected on native *Schizochytrium* secreted proteins as determined by NSI-full MS analysis of permethylated N-glycans.
Figure 30:
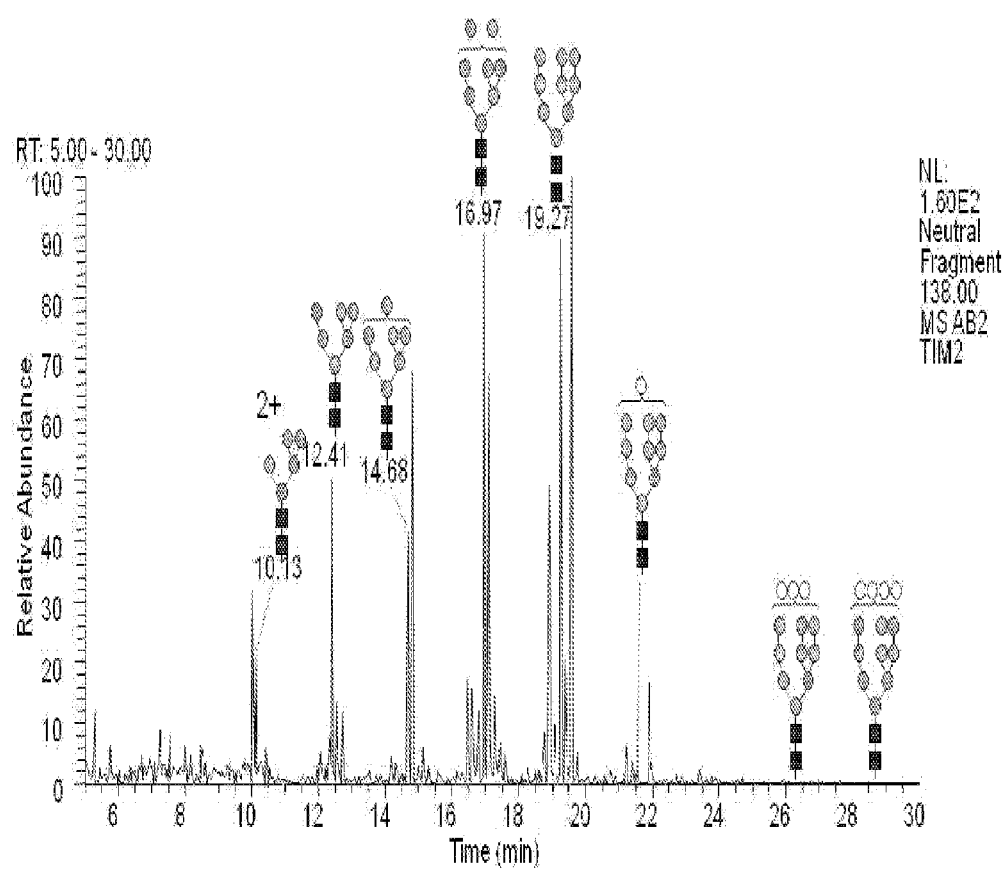
FIG. 30 shows N-glycan structures detected on native *Schizochytrium* secreted proteins as determined by NSI-Total Ion Mapping of permethylated N-glycans.

The N-glycosylation of native *Schizochytrium* proteins was determined. *Schizochytrium* was found to share steps in common with the glycosylation pathway of mammals and insects and was not observed to utilize the hypermannosylation pathway characteristic of yeast. FIG. 29 and FIG. 30 show glycan structures detected by mass spectrometry analysis of *Schizochytrium* secreted proteins. In particular, characteristic peaks were observed for $GlcNAc_2Man_5$ at m/z 1580, $GlcNAc_2Man_6$ at m/z 1785, and $GlcNAc_2Man_7$ at m/z 1991.

Example 18

Transformation of *Schizochytrium* by Electroporation

*Schizochytrium* sp. ATCC 20888 cells were grown in M50-20 media (see U.S. Publ. No. 2008/0022422) on a shaker at 200 rpm for 48 h at 29° C. The cells were diluted at 1:100 into fresh media and grown overnight. The cells were centrifuged and resuspended in 1 M mannitol and 10 mM $CaCl_2$ (pH 5.5) to a final concentration of 2 $OD_{600}$ units. 5 mL of cells were mixed with 0.25 mg/mL Protease XIV (Sigma Chemical) and incubated on a shaker for 4 h. The cells were washed twice with 10% ice cold glycerol and resuspended in 500 µL of cold 10% glycerol. 90 µL was aliquoted in to a prechilled 0.2 cm gap electro-cuvettes (Biorad 165-2086). 10 µl of DNA (1-5 µg) was added to the cuvette, mixed gently, and held on ice. Cells were electroporated with a recombinant vector at 200 ohms (resistance), 25 µF, and a voltage ranging from 0 V to 500 V (for a 0.1 cm cuvette gap distance) or 500 V (for a 0.2 cm cuvette gap distance). 0.5 mL of media was added immediately to the cuvette. The cells were then transferred to 4.5 mL of M50-20 media and incubated for 2-3 h at 100 rpm on a shaker. The cells were centrifuged and resuspended in 0.5 mL of media and plated onto 2-5 M2B plates with appropriate selection (if needed) and incubated at 29° C.

Table 2 shows the number of *Schizochytrium* sp. ATCC 20888 transformants generated after pretreatment with different enzyme combinations (parameters of 300 V and 0.1 cm cuvette gap distance).

Table 3 shows the number of *Schizochytrium* sp. ATCC 20888 transformants generated after pretreatment with different enzyme combinations and voltages (0.1 cm cuvette gap distance).

Table 4 shows the number of *Schizochytrium* sp. ATCC 20888 transformants generated using different electroporation cuvette gap distances. The cells were pretreated with 0.25 mg/mL Protease XIV.

Table 5 shows the number of *Schizochytrium* sp. ATCC 20888 transformants generated using different electroporation voltages. Cells were pretreated with 0.1 mg/mL Snail Acetone Powder+0.25 mg/mL Protease XIV (0.1 cm cuvette gap distance).

TABLE 2

*Schizochytrium* transformants generated after pretreatment with different enzyme combinations

| Treatment | # of transformants |
|---|---|
| None | 0 |
| 0.1 mg/mL Snail Acetone Powder + 0.25 mg/mL Protease XIV | 450 |
| Snail Acetone Powder, before addition of Protease XIV | 225 |
| 0.1X Sulfatase + Protease XIV | 240 |
| 0.1X β-Glucuronidase + Protease XIV | 430 |
| 0.5X Sulfatase + Protease XIV | 200 |
| 0.5X β-Glucuronidase + Protease XIV | 375 |

TABLE 3

*Schizochytrium* transformants generated after pretreatment with different enzyme combinations and voltages

| Treatment | # of transformants at 200 V | # of transformants at 250 V |
|---|---|---|
| 0.1 mg/mL Snail Acetone Powder + 0.25 mg/mL Protease XIV | 315 | 380 |
| Protease XIV | 820 | 1360 |
| 0.5X β-Glucuronidase + Protease XIV | 650 | 110 |
| 0.1X β-Glucuronidase + Protease XIV | 400 | 560 |

TABLE 4

*Schizochytrium* transformants generated using different electroporation cuvette gap distances (pretreated with 0.25 mg/mL Protease XIV)

| Cuvette gap | # of transformants |
|---|---|
| 0.1 cm (250 V) | 345 |
| 0.2 cm (500 V) | 530 |

TABLE 5

*Schizochytrium* transformants generated using different electroporation voltages (pretreated with 0.1 mg/mL Snail Acetone Powder + 0.25 mg/mL Protease XIV)

| | Voltage (V) | | | | | | |
|---|---|---|---|---|---|---|---|
| | 0 | 100 | 150 | 200 | 300 | 400 | 500 |
| # of transformants | 0 | 4 | 490 | 1320 | 794 | 156 | 100 |

Example 19

Expression of Invertase in *Schizochytrium*

The vector pAB0018 was digested with BamHI and NdeI resulting in two fragments of 838 bp and 9879 bp in length. The 9879 bp fragment was fractionated by standard electrophoretic techniques in an agar gel, purified using commercial DNA purification kits, and ligated to a sequence (SEQ ID NO:57) comprising a polynucleotide sequence encoding the native secretion signal of the Sec1 protein of *Schizochytrium* followed by a synthetic sequence encoding the mature invertase protein (SUC2) of *Saccharomyces cerevisiae*, which was codon-optimized for expression in *Schizochytrium* (see FIG. 42). A fusion sequence containing the sequences encoding the Sec1 signal peptide and the *Saccharomyces cerevisiae* invertase protein was inserted into the *Schizochytrium* vector pSchiz, followed by digestion with BamHI and NdeI to yield SEQ ID NO:57.

Figure 31:
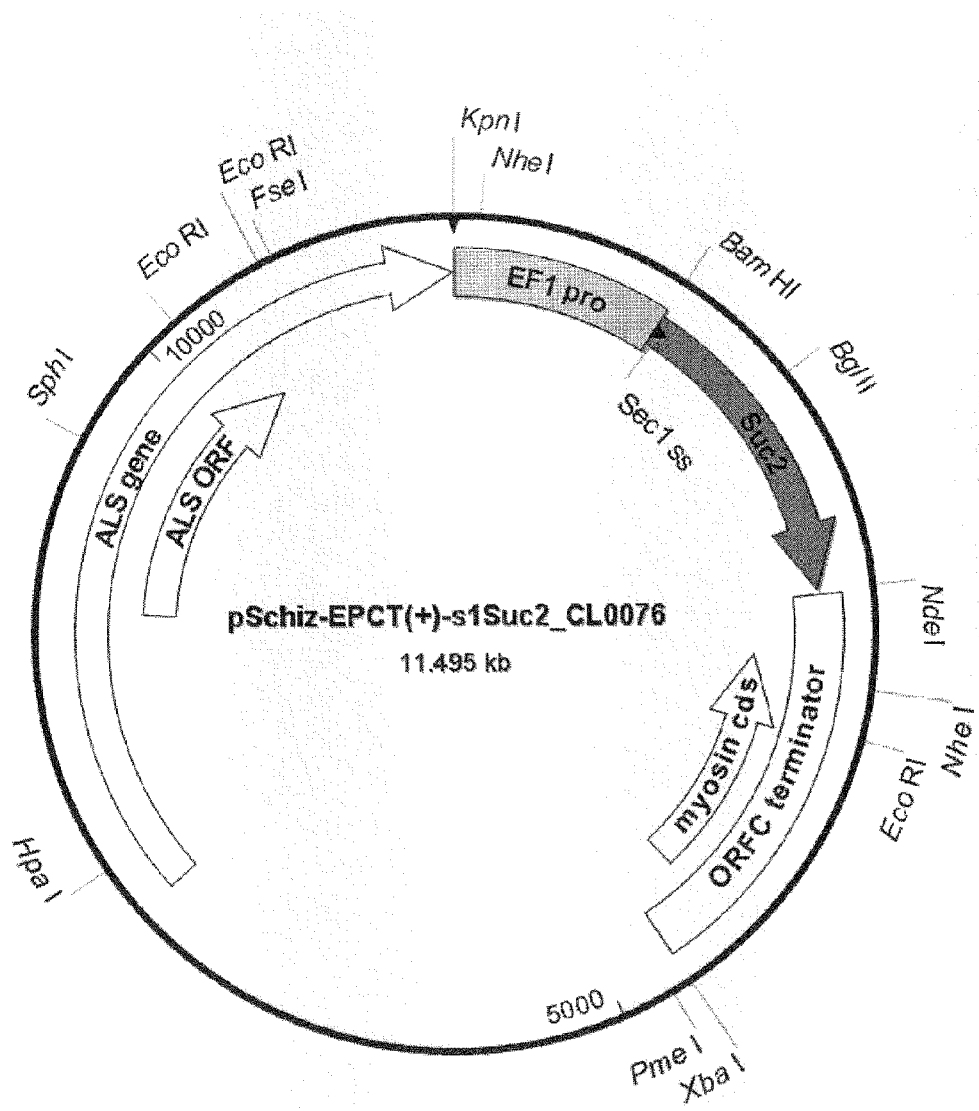
FIG. 31 shows a plasmid map of pSchiz-EPCT(+)-s1Suc2_CL0076, also termed pCL0076.
Figure 32:
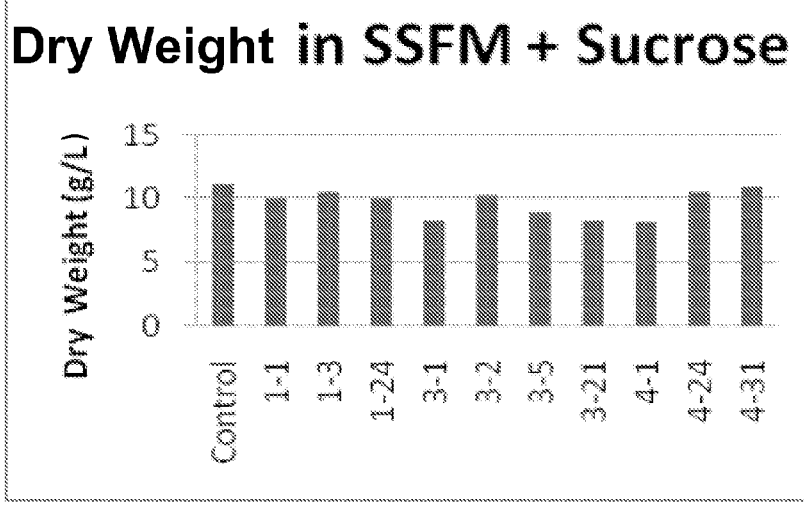
FIG. 32 shows dry weight (g/L) of cell pellets from cultures of *Schizochytrium* sp. ATCC 20888 transformed with pCL0076 grown on sucrose-SSFM. The transformants are referred to as 1-1, 1-3, 1-24, 3-1, 3-2, 3-5, 3-21, 4-1, 4-24, and 4-31. "Control" refers to wild-type *Schizochytrium* sp. ATCC 20888 cells grown on glucose-SSFM.
Figure 33:
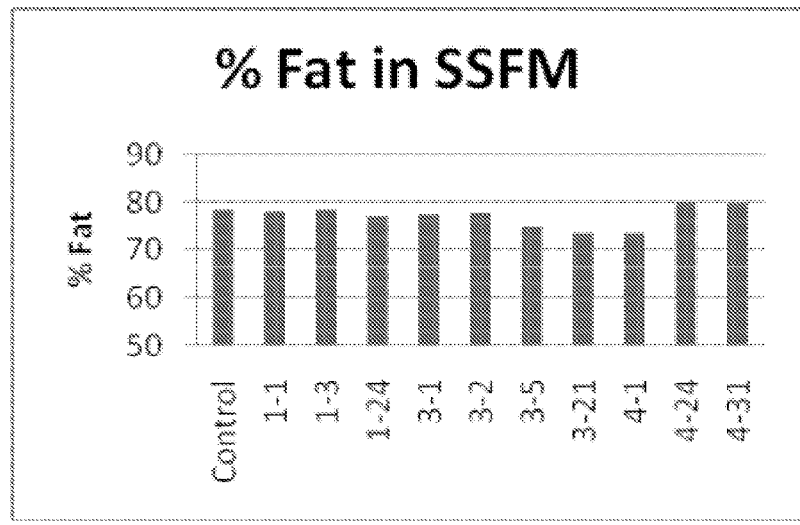
FIG. 33 shows fat content (expressed as % weight of the dry biomass) in cell pellets from cultures of *Schizochytrium* sp. ATCC 20888 transformed with pCL0076 grown on sucrose-SSFM. The transformants are referred to as 1-1, 1-3, 1-24, 3-1, 3-2, 3-5, 3-21, 4-1, 4-24, and 4-31. "Control" refers to wild-type *Schizochytrium* sp. ATCC 20888 cells grown on glucose-SSFM.
Figure 34:
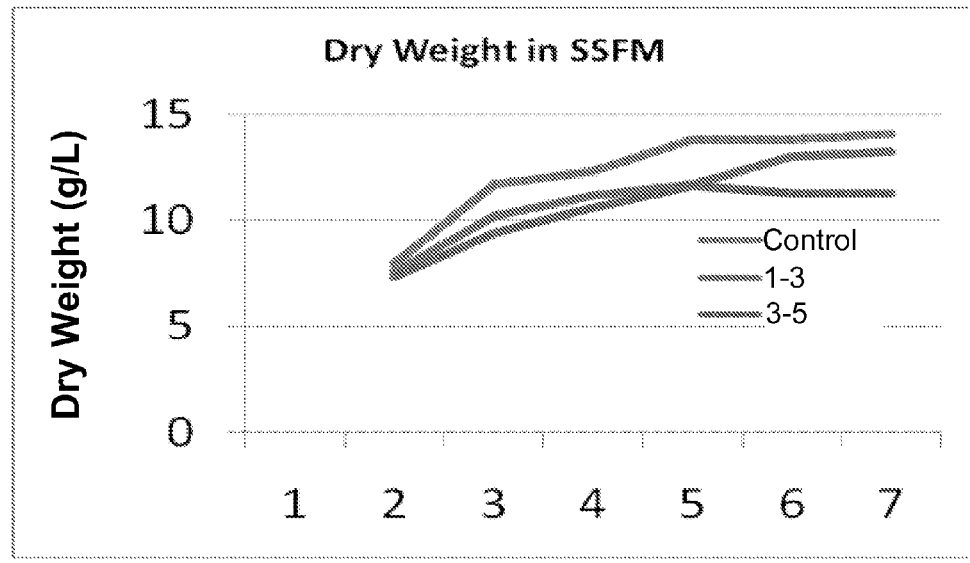
FIG. 34 shows dry weight (g/L) of cell pellets measured over time for cultures of *Schizochytrium* sp. ATCC 20888 transformed with pCL0076 grown on sucrose-SSFM. The transformants are referred to as 1-3 and 3-5. "Control" refers to wild-type *Schizochytrium* sp. ATCC 20888 cells grown on glucose-SSFM.
Figure 35:
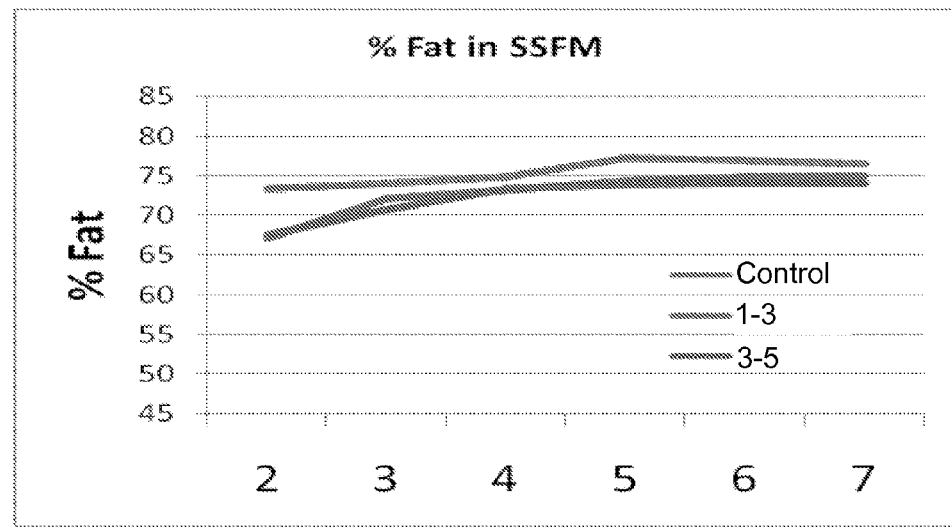
FIG. 35 shows fat content (expressed as % weight of the dry biomass) in cell pellets from cultures of two transformants grown on sucrose-SSFM. The transformants are referred to as 1-3 and 3-5. "Control" refers to wild-type *Schizochytrium* sp. ATCC 20888 cells grown on glucose-SSFM.
Figure 36:
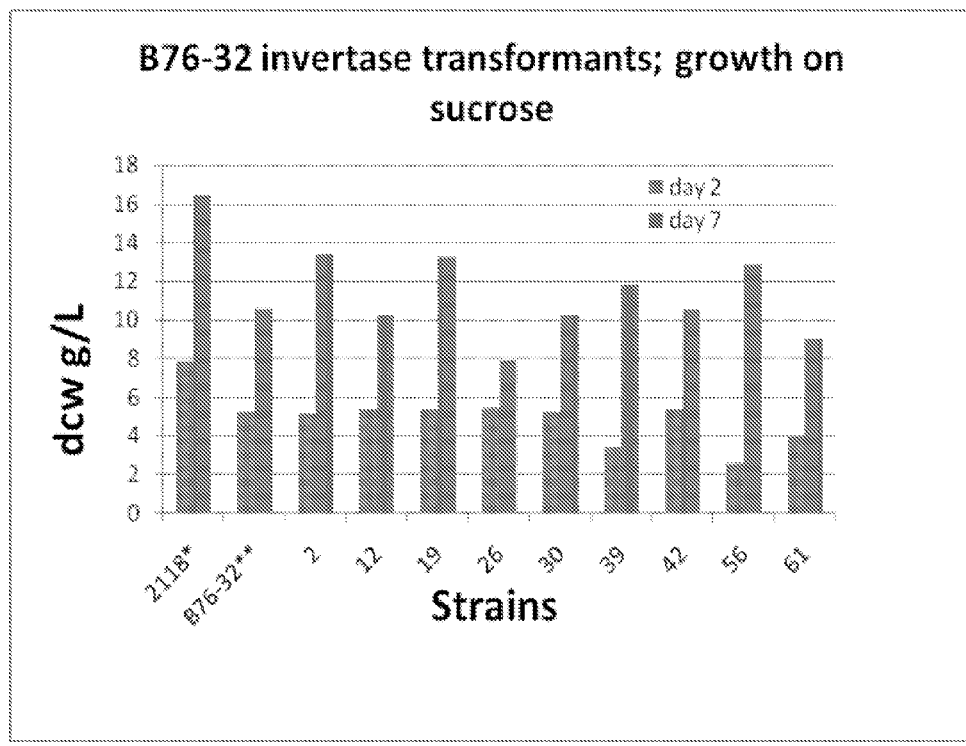
FIG. 36 shows dry weight (g/L) of cell pellets from cultures of *Schizochytrium* strain B76-32 transformed with pCL0076 and harvested after either 2 days or 7 days of growth in sucrose-SSFM. "2118*" refers to a sub-isolate of wild-type *Schizochytrium* sp. ATCC 20888 cells grown on glucose-SSFM. "B76-32**" refers to the B76-32 parent strain grown on glucose-SSFM.
Figure 37:
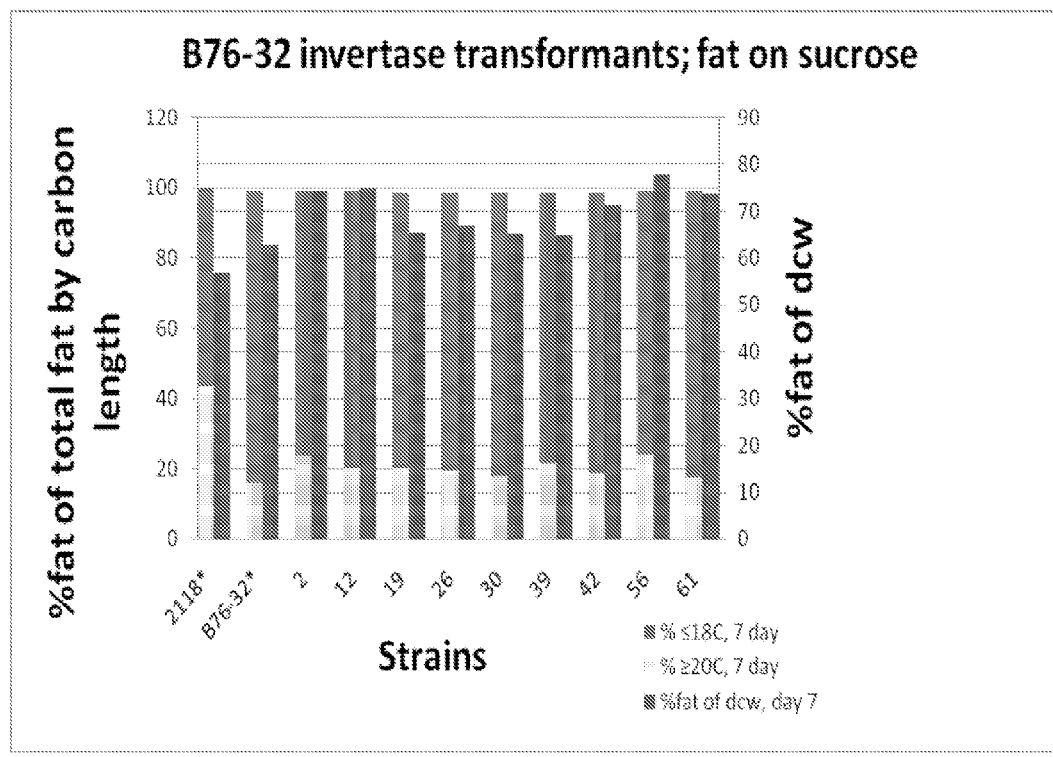
FIG. 37 shows fat content of cell pellets from cultures of *Schizochytrium* strain B76-32 transformed with pCL0076 and harvested after either 2 days or 7 days of growth in sucrose-SSFM. The rightmost column for each sample shows fat content as % weight of the dry biomass. The leftmost column for each sample shows % of total fat composed of acyl groups with 18 or fewer carbons (light grey) or 20 or more carbons (medium grey). "2118*" refers to a sub-isolate of wild-type *Schizochytrium* sp. ATCC 20888 cells grown on glucose-SSFM. "B76-32**" refers to the B76-32 parent strain grown on glucose-SSFM.

The ligation product was used to transform a commercially supplied strain of competent DH5α *E. coli* cells (Invitrogen) using the manufacturer's protocol. Several of the resulting clones were propagated and their plasmids were extracted and purified. These plasmids were then screened by restriction digests or PCR to confirm that the ligation generated the expected plasmid vectors. One such plasmid vector resulting from a ligation with SEQ ID NO:57 was verified by Sanger sequencing and was designated pCL0076 (SEQ ID NO:58). See FIG. 31.

Cultures of *Schizochytrium* sp. ATCC 20888 and a genetically modified *Schizochytrium* derivative, designated B76-32 were grown in M2B medium consisting of 10 g/L glucose, 0.8 g/L $(NH_4)_2SO_4$, 5 g/L $Na_2SO_4$, 2 g/L $MgSO_4.7H_2O$, 0.5 g/L $KH_2PO_4$, 0.5 g/L KCl, 0.1 g/L $CaCl_2.2H_2O$, 0.1 M MES (pH 6.0) 0.1% PB26 metals, and 0.1% PB26 Vitamins (v/v). PB26 vitamins consisted of 50 mg/mL vitamin B12, 100 µg/mL thiamine, and 100 µg/mL Ca-pantothenate. PB26 metals were adjusted to pH 4.5 and consisted of 3 g/L $FeSO_4.7H_2O$, 1 g/L $MnCl_2.4H_2O$, 800 mg/mL $ZnSO_4.7H_2O$, 20 mg/mL $CoCl_2.6H_2O$, 10 mg/mL $Na_2MoO_4.2H_2O$, 600 mg/mL $CuSO_4.5H_2O$, and 800 mg/mL $NiSO_4.6H_2O$. PB26 stock solutions were filter sterilized separately and added to the broth after autoclaving. Glucose, $KH_2PO_4$, and $CaCl_2.2H_2O$ were each autoclaved separately from the remainder of the broth ingredients before mixing to prevent salt precipitation and carbohydrate caramelizing. All medium ingredients were purchased from Sigma Chemical (St. Louis, Mo.). Strain B76-32 is a derivative of *Schizochytrium* sp. ATCC 20888 engineered according to U.S. Pat. No. 7,211,418 and U.S. Patent Publication Nos. 2008/0022422 and 2008/0026434.

Cultures of *Schizochytrium* sp. ATCC 20888 and B76-32 were grown to log phase and were transformed with the vector pCL0076 using electroporation with enzyme pretreatment as described below.

Electroporation with Enzyme Pretreatment—

Cells were grown in 50 mL of M50-20 media (see U.S. Publ. No. 2008/0022422) on a shaker at 200 rpm for 2 days at 30° C. The cells were diluted at 1:100 into M2B media (see following paragraph) and grown overnight (16-24 h), attempting to reach mid-log phase growth ($OD_{600}$ of 1.5-2.5). The cells were centrifuged in a 50 mL conical tube for 5 min at about 3000×g. The supernatant was removed and the cells were resuspended in 1 M mannitol, pH 5.5, in a suitable volume to reach a final concentration of 2 $OD_{600}$ units. 5 mL of cells were aliquoted into a 25 mL shaker flask and amended with 10 mM $CaCl_2$ (1.0 M stock, filter sterilized) and 0.25 mg/mL Protease XIV (10 mg/mL stock, filter sterilized; Sigma-Aldrich, St. Louis, Mo.). Flasks were incubated on a shaker at 30° C. and about 100 rpm for 4 h. Cells were monitored under the microscope to determine the degree of protoplasting, with single cells desired. The cells were centrifuged for 5 min at about 2500×g in round-bottom tubes (i.e., 14 mL Falcon™ tubes, BD Biosciences, San Jose, Calif.). The supernatant was removed and the cells were gently resuspended with 5 mL of ice cold 10% glycerol. The cells were re-centrifuged for 5 min at about 2500×g in round-bottom tubes. The supernatant was removed and the cells were gently resuspended with 500 μL of ice cold 10% glycerol, using wide-bore pipette tips. 90 μL of cells were aliquoted into a prechilled electro-cuvette (Gene Pulser® cuvette-0.1 cm gap or 0.2 cm gap, Bio-Rad, Hercules, Calif.). 1 μg to 5 μg of DNA (in less than or equal to a 10 μL volume) was added to the cuvette, mixed gently with a pipette tip, and placed on ice for 5 min. Cells were electroporated at 200 ohms (resistance), 25 μF (capacitance), and either 250V (for 0.1 cm gap) or 500V (0.2 cm gap). 0.5 mL of M50-20 media was added immediately to the cuvette. The cells were then transferred to 4.5 mL of M50-20 media in a 25 mL shaker flask and incubated for 2-3 h at 30° C. and about 100 rpm on a shaker. The cells were centrifuged for 5 min at about 2500×g in round bottom tubes. The supernatant was removed and the cell pellet was resuspended in 0.5 mL of M50-20 media. Cells were plated onto an appropriate number (2 to 5) of M2B plates with appropriate selection (if needed) and incubated at 30° C.

Transformants were selected for growth in either M2B+ SMM media or directly selected for growth on sucrose by plating onto MSFM+sucrose. For MSFM+sucrose selection, after 1-2 weeks colonies were replated with several passes onto fresh sucrose-containing media. It was determined that expression of invertase can be used as a selectable marker for thraustochytrid colonies grown on sucrose as a sole carbon source.

For the following experiments, primary transformants were selected for growth on solid M2B media containing 20 g/L agar (VWR, West Chester, Pa.) and 10 μg/mL SMM (Chem Service, Westchester, Pa.) after 2-6 days of incubation at 27° C. All primary transformants were manually transferred to fresh M2B plates with SMM. After 1 week the colonies were transferred to MSFM and 5 g/L sucrose without SMM. After 1 week the largest colonies were transferred to fresh MSFM/sucrose media plates. Ten of the *Schizochytrium* sp. ATCC 20888 transformants growing on sucrose were selected for further characterization and were designated as 1-1, 1-3, 1-24, 3-1, 3-2, 3-5, 3-21, 4-1, 4-24, and 4-31, respectively. Nine of the B76-32 transformants growing on sucrose were selected for further characterization and were designated as B76-32 #2, #12, #19, 326, #30, #39, #42, #56, and #61.

Colonies growing on sucrose (1-1, 1-3, 1-24, 3-1, 3-2, 3-5, 3-21, 4-1, 4-24, 4-31) were removed from plates using an inoculation loop and transferred into culture tubes containing 5 mL of sucrose media and grown for 4 days at 29° C. on a shaker. 2 mL of this culture was used to inoculate 50 mL of media (MSFM or SSFM) in 250 ml flasks and grown at 29° C. on a shaker at 200 rpm.

Control flasks of the parental strain *Schizochytrium* sp. ATCC 20888 were grown the same way but using glucose containing media. Cells were harvested after 7 days. Cells were centrifuged and washed with a 50% isopropanol:distilled water mixture. The pelleted cells were freeze-dried, weighed, and a fatty acid methyl esters (FAME) analysis was performed. Growth and fat content of CL0076 transformants of *Schizochytrium* sp. ATCC 20888 or B76-32 were assayed gravimetrically and by gas chromatography of derivatized oils as previously described in U.S. Publ. No. 2008/0022422, incorporated herein by reference in its entirety. Results are shown in Tables 6-9. Dry weights and fat content of pellets from shake flask cultures of transformants as well as parent strains are shown in FIGS. 32-37.

SSFM media: 50 g/L glucose or sucrose, 13.6 g/L $Na_2SO_4$, 0.7 g/L $K_2SO_4$, 0.36 g/L KCl, 2.3 g/L $MgSO_4.7H_2O$, 0.1M MES (pH 6.0), 1.2 g/L $(NH_4)_2SO_4$, 0.13 g/L monosodium glutamate, 0.056 g/L $KH_2PO_4$, and 0.2 g/L $CaCl_2.2H_2O$. Vitamins were added at 1 mL/L from a stock consisting of 0.16 g/L vitamin B12, 9.7 g/L thiamine, and 3.3 g/L Ca-pantothenate. Trace metals were added at 2 mL/L from a stock consisting of 1 g/L citric acid, 5.2 g/L $FeSO_4.7H_2O$, 1.5 g/L $MnCl_2.4H_2O$, 1.5 g/L $ZnSO_4.7H_2O$, 0.02 g/L $CoCl_2.6H_2O$, 0.02 g/L $Na_2MoO_4.2H_2O$, 1.0 g/L $CuSO_4.5H_2O$, and 1.0 g/L $NiSO_4.6H_2O$, adjusted to pH 2.5.

Modified SFM (MSFM) media: 10 g/L glucose or sucrose, 25.0 g/L NaCl, 1.0 g/L KCl, 0.2 g/L $(NH_4)_2SO_4$, 5 g/L, 5.0 g/L $MgSO_4.7H_2O$, 0.1 g/L $KH_2PO_4$, 0.3 g/L $CaCl_2.2H_2O$, 0.1 M HEPES (pH 7.0), 0.1% PB26 metals, and 0.1% PB26 Vitamins (v/v). Vitamins were added at 2 mL/L from a stock consisting of 0.16 g/L vitamin B12, 9.7 g/L thiamine, and 3.3 g/L Ca-pantothenate. Trace metals were added at 2 mL/L from a stock consisting of 1 g/L citric acid, 5.2 g/L $FeSO_4.7H_2O$, 1.5 g/L $MnCl_2.4H_2O$, 1.5 g/L $ZnSO_4.7H_2O$, 0.02 g/L $CoCl_2.6H_2O$, 0.02 g/L $Na_2MoO_4.2H_2O$, 1.0 g/L $CuSO_4.5H_2O$, and 1.0 g/L $NiSO_4.6H_2O$, adjusted to pH 2.5.

Table 6 shows the growth and fat levels of *Schizochytrium* sp. ATCC 20888 grown in MSFM with glucose, fructose, sucrose, or no added carbon source.

Table 7 shows the dry weight and % fatty acid for *Schizochytrium* sp. ATCC 20888 grown in MSFM media with glucose (control) and *Schizochytrium* sp. ATCC 20888 transformed cell lines grown in MSFM media with sucrose.

Table 8 shows the dry weight and % fatty acid for *Schizochytrium* sp. ATCC 20888 grown in SSFM media with glucose (control) and *Schizochytrium* sp. ATCC 20888 transformed cell lines grown in SSFM media with sucrose.

Table 9 shows the dry weight and % fatty acid for *Schizochytrium* B76-32 grown in SSFM media with glucose (control) and *Schizochytrium* B76-32 transformed cell lines grown in SSFM media with sucrose.

TABLE 6

Growth and fat levels of *Schizochytrium* sp. ATCC 20888 grown in MSFM with glucose, fructose, sucrose or no added carbon source.

|  | Glucose | Fructose | Sucrose | No added carbon |
|---|---|---|---|---|
| DW (g/L) | 2.84 | 2.65 | 0.16 | 0.11 |
| % FA | 66.5 | 65.3 | ND | ND |

DW = Dry Weight
FA = Fatty Acids

TABLE 7

*Schizochytrium* sp. ATCC 20888 transformed cell lines grown in MSFM media with sucrose.

|  | 20888 control | 1-1 | 1-3 | 3-2 | 3-5 | 3-21 | 4-1 | 4-24 | 4-31 |
|---|---|---|---|---|---|---|---|---|---|
| DW (g/L) | 2.94 | 2.49 | 2.79 | 2.21 | 2.60 | 2.64 | 2.44 | 3.05 | 2.24 |
| % FA | 70.87 | 70.79 | 72.36 | 67.97 | 69.78 | 71.05 | 68.84 | 73.85 | 73.66 |

DW = Dry Weight
FA = Fatty Acids

TABLE 8

*Schizochytrium* sp. ATCC 20888 transformed cell lines grown in SSFM media with sucrose.

|  | 20888 control | 1-1 | 1-3 | 1-24 | 3-1 | 3-2 | 3-5 | 3-21 | 4-1 | 4-24 | 4-31 |
|---|---|---|---|---|---|---|---|---|---|---|---|
| DW (g/L) | 11.24 | 10.04 | 10.51 | 9.99 | 8.40 | 10.29 | 9.03 | 8.34 | 8.16 | 10.63 | 10.92 |
| % FA | 78.22 | 78.20 | 76.29 | 77.10 | 77.37 | 77.71 | 74.97 | 73.44 | 73.65 | 80.05 | 79.82 |

DW = Dry Weight
FA = Fatty Acids

TABLE 9

B76-32 transformed cell lines grown in SSFM media with sucrose.

|  | B76-32 control | #2 | #12 | #19 | #26 | #30 | #39 | #42 | #56 | #61 |
|---|---|---|---|---|---|---|---|---|---|---|
| 7-day DW (g/L) | 10.56 | 13.37 | 10.21 | 13.26 | 7.88 | 10.26 | 11.81 | 10.47 | 12.84 | 8.97 |
| % FA | 62.8 | 74.3 | 75.2 | 65.4 | 66.9 | 65.1 | 64.8 | 71.4 | 77.9 | 73.7 |

DW = Dry Weight
FA = Fatty Acids

Immunoblotting—

Figure 38:
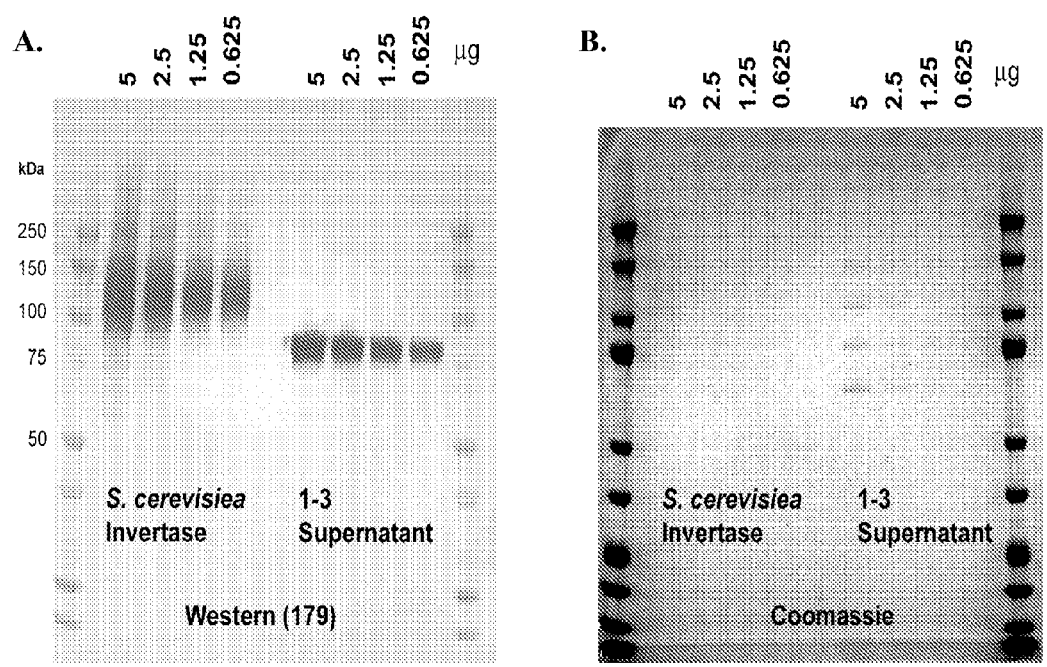
FIG. 38A shows a Western blot for invertase protein and FIG. 38B shows a corresponding Coomassie-stained SDS-PAGE gel. A *S. cerevisiae* invertase control and cell-free supernatants of a 3-day culture of pCL0076 transformant 1-3 were loaded in amounts of 5 µg, 2.5 µg, 1.25 µg, and 0.625 µg, respectively, as indicated at the top of the Western blot.

Cell-free supernatants of 50 mL shake-flask cultures grown in SSFM for 3 days (see U.S. Publ. No. 2008/0022422) were collected after cultures were centrifuged at 5000×g. Culture supernatants were used either directly for SDS-PAGE or were concentrated 50 to 100-fold using commercially available concentrators equipped with permeable membranes permitting concentration of all components heavier than 10 kDa. Total protein concentration was measured by Bradford assay (Biorad). The expression of invertase was then verified by immunoblot analysis following standard immunoblotting procedure (Sambrook et al.). Briefly, the proteins (0.625 μg to 5 μg) were separated by SDS-PAGE on a bis-tris gel (Invitrogen, Carlsbad, Calif., USA). The proteins were then stained with Coomassie blue (SimplyBlue Safe Stain, Invitrogen) or transferred onto polyvinylidene fluoride membrane and probed for the presence of invertase protein with an invertase antisera (Open Biosystems) derived from rabbits that had been injected with a pure preparation of *Saccharomyces cerevisiae* invertase (Sigma). The membrane was subsequently incubated with a mouse anti-rabbit secondary antibody coupled to alkaline phosphatase (Promega). The membrane was then treated with 5-bromo-4-chloro-3-indoyl-phosphate/nitroblue tetrazolium solution (BCIP/NBT) according to the manufacturer's instructions (KPL, Gaithersburg, Md.). An example is presented in FIG. 38. Anti-invertase immunoblot and corresponding Coomassie blue-stained gel are presented in panels A and B, respectively. Of the four major bands seen in culture supernatants of clone 1-3, only one was shown to react with anti-invertase antisera. The identity of the protein was confirmed by peptide sequence analysis.

Functional Assay—

The enzyme EC 3.2.1.26 is an invertase type of sucrase that catalyzes the hydrolysis of sucrose to fructose and glucose. Sucrase activity was measured by the rate of liberation of fructose and glucose from sucrose. The assay was performed crudely by adding sucrose to fermentation broth supernatant and the glucose/fructose content was measured by HPLC.

Figure 39A:
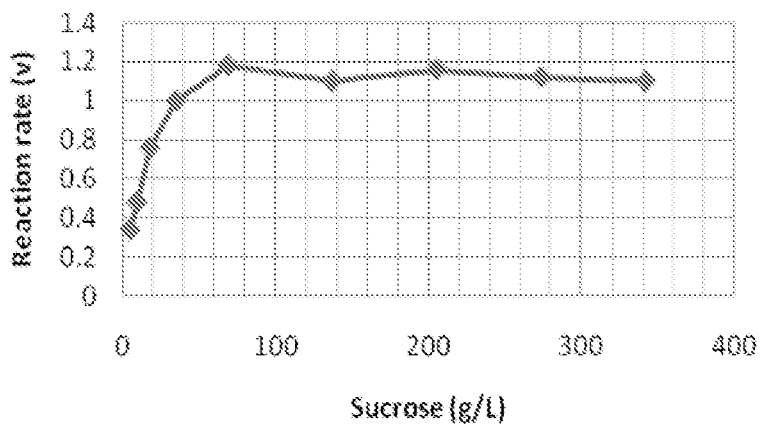
FIG. 39A shows an invertase activity assay illustrated by the reaction rate as a function of sucrose concentration.
Figure 39B:
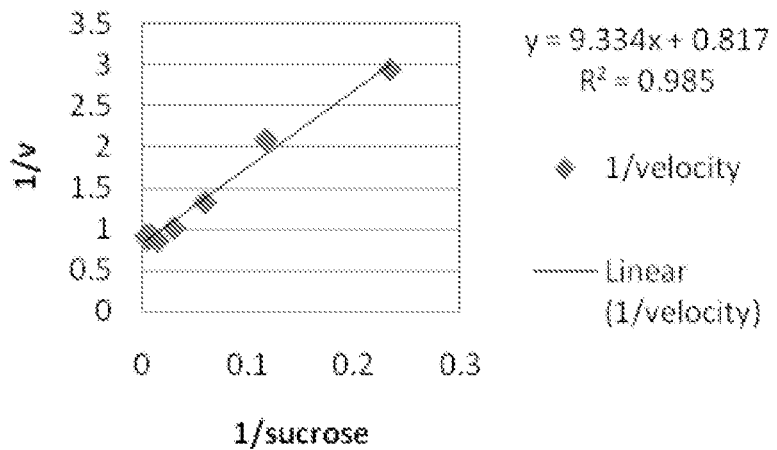
FIG. 39B shows a standard Lineweaver-Burk plot used to calculate the Km and Vmax.

*Schizochytrium* strain B76-32 #3 was grown in MSFM (with sucrose) until the OD reached about 4 in 50 mL shake flasks at 29° C. Cells were spun down for 15 min at 4500×g and invertase activity was measured in the supernatant. Invertase was assayed by adding 0.1 M sucrose to varying volumes of fermentation broth and adjusting the final volume to 1 mL. The reaction was incubated at 55° C. for 3 min. Termination of the reaction was done at 100° C. for 10 min, then frozen until analysis which consists of the determination of glucose, fructose, and sucrose by HPLC. HPLC was performed using a modified version of the process described in Liu et al., *Food Sci.* 28:293-296 (2007). Briefly, mono- and di-saccharides were separated using an HPLC with a Luna NH$_2$ column and detected using an RID (refractive index detector). Identification was carried out by comparing retention times to those of standards. Quantitation was by an external standard calibration. The reaction rate as a function of sucrose concentration is shown in FIG. 39A. The Km (33.4 mM) and Vmax (6.8 mM glucose/min) were calculated from a standard Lineweaver-Burk plot. See FIG. 39B.

Glycosylation Analysis—

Supernatant proteins were separated by SDS-PAGE on a 4-12% bis-tris gel (Invitrogen). The proteins were then stained with Coomassie blue (SimplyBlue Safe Stain, Invitrogen). The stained proteins of interest were cut from the gel and slices cut into smaller pieces (~1 mm$^3$) and destained alternately with 40 mM Ammonium bicarbonate (AmBic) and 100% acetonitrile until the color turned clear. Destained gel was reswelled in 10 mM DTT in 40 mM AmBic at 55° C. for 1 h. The DTT solution was exchanged with 55 mM Iodoacetamide (IAM) and incubated in the dark for 45 min. Incubation was followed by washing alternately with 40 mM AmBic and 100% acetonitrile twice. Dehydrated gel was reswelled with trypsin solution (trypsin in 40 mM AmBic) on ice for 45 min initially, and protein digestion was carried out at 37° C. overnight. The supernatant was transferred into another tube. Peptides and glycopeptides were extracted from the gel in series with 20% acetonitrile in 5% formic acid, 50% acetonitrile in 5% formic acid, and then 80% acetonitrile in 5% formic acid. The sample solutions were dried and combined into one tube. Extracted tryptic digest was passed through a C18 sep-pak cartridge and washed with 5% acetic acid to remove contaminants (such as salts and SDS). Peptides and glycopeptides were eluted in series with 20% isopropanol in 5% acetic acid, 40% isopropanol in 5% acetic acid, and 100% isopropanol and were dried in a speed vacuum concentrator. The dried samples were combined and then reconstituted with 50 mM sodium phosphate buffer (pH 7.5) and heated at 100° C. for 5 min to inactivate trypsin. The tryptic digest was incubated with PNGase F at 37° C. overnight to release N-glycans. After digestion, the sample was passed through a C18 sep-pak cartridge and the carbohydrate fraction was eluted with 5% acetic acid and dried by lyophilization. Released N-linked oligosaccharides were peimethylated based on the method of Anumula and Taylor, *Anal Biochem.* 203:101-108 (1992) and profiled by mass spectrometry. Mass spectrometric analysis was performed following the method developed at the Complex Carbohydrates Research Center (Aoki K et al., *J. Biol. Chem.* 282:9127-42 (2007). Mass analysis was determined by using NSI-LTQ/MS$_n$. Briefly, permethylated glycans were dissolved in 1 mM NaOH in 50% methanol and infused directly into the instrument (LTQ, Theimo Finnigan) at a constant flow rate of 0.4 µL/min. The MS analysis was performed in the positive ion mode. For total ion mapping, automated MS/MS analysis (at 35 collision energy), m/z range from 500 to 2000 was scanned in successive 2.8 mass unit windows that overlapped the preceding window by 2 mass units.

Figure 40B:
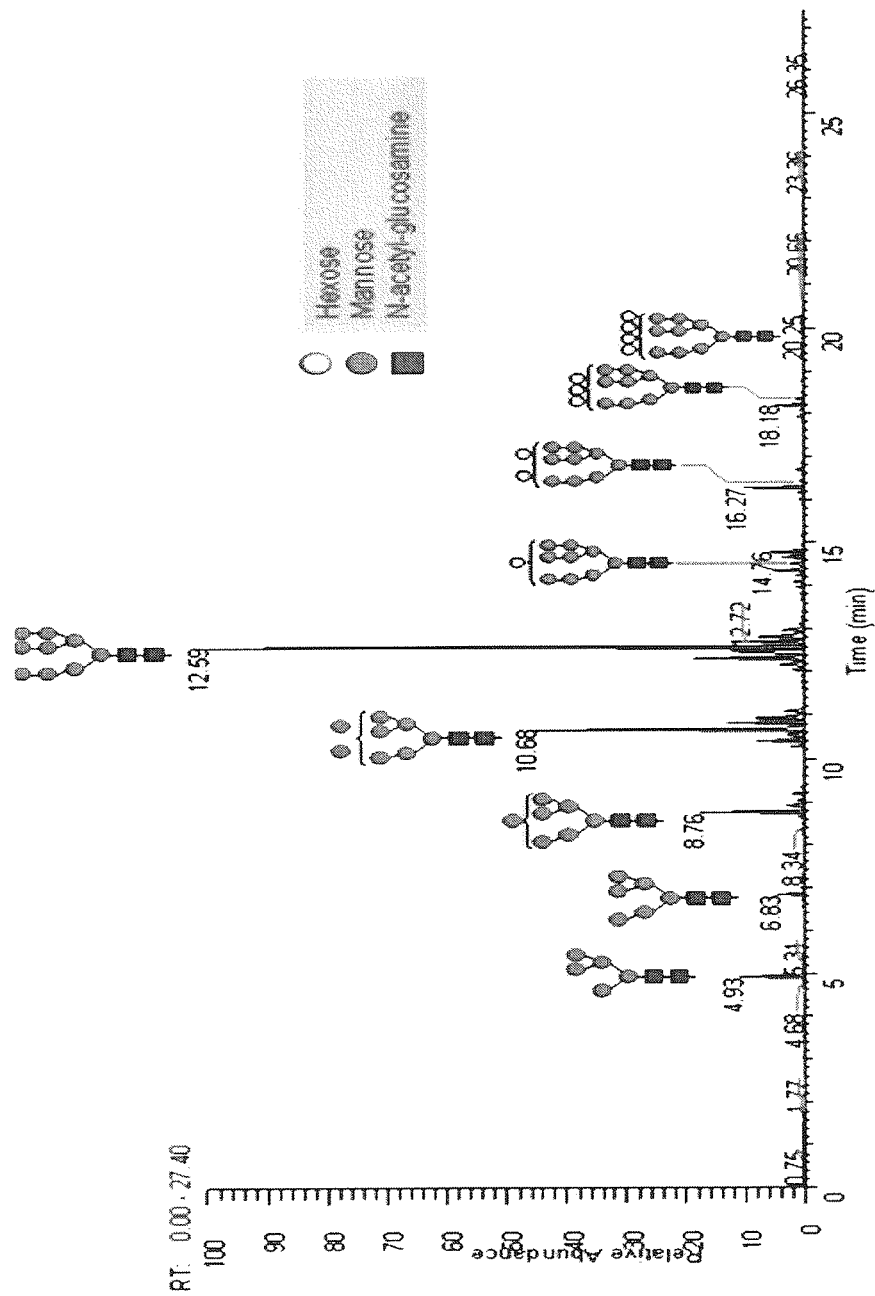
FIG. 40B shows a table of glycan species obtained by NSI-Total Ion Mapping of permethylated N-glycans.

Total ion mapping was performed to examine the presence of fragment ions indicative of glycans. All MS/MS data from m/z 500 through m/z 2000 were taken and the raw data were analyzed manually. The chromatogram and table of species obtained by NSI-total ion mapping are shown in FIG. 40A and FIG. 40B. This chromatogram was processed by the scan filter; a neutral loss of m/z 139 is characteristic of high-mannose type glycans. Total ion mapping revealed that this sample contains a series of high-mannose type glycans with long mannose chains. These results are similar to the N-glycan structures detected on native *Schizochytrium* secreted proteins, as determined by the same methodology as Example 17 (see FIG. 30).

Example 20

Expression of *Aspergillus niger* Invertase in *Schizochytrium*

Figure 43:
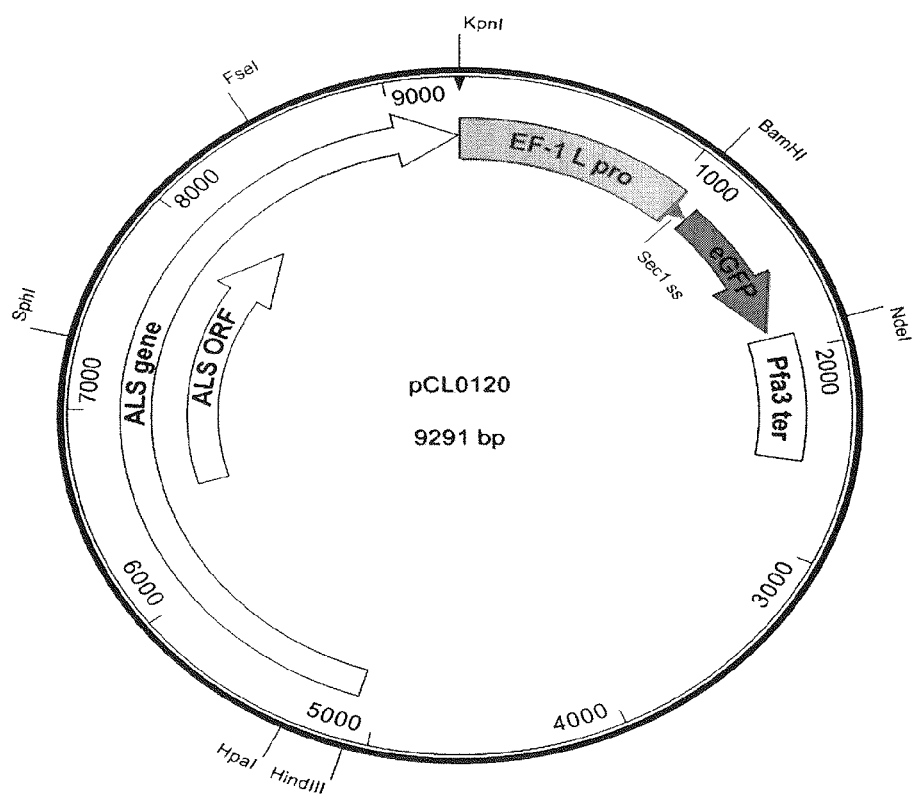
FIG. 43 shows a plasmid map of pCL0120.

The vector pAB0018 (ATCC Accession No. PTA-9616) was digested with HindIII, treated with mung bean nuclease, purified, and then further digested with KpnI generating four fragments of various sizes. A fragment of 2552 bp was isolated by standard electrophoretic techniques in an agar gel and purified using commercial DNA purification kits. A second digest of pAB0018 with PmeI and Kpn was then performed. A fragment of 6732 bp was isolated and purified from this digest and ligated to the 2552 bp fragment. The ligation product was then used to transform commercially supplied strains of competent DH5-α *E. coli* cells (Invitrogen) using the manufacturer's protocol. Plasmids from ampicillin-resistant clones were propagated, purified, and then screened by restriction digests or PCR to confirm that the ligation generated the expected plasmid structures. One verified plasmid was designated pCL0120. See FIG. 43.

Figure 45:
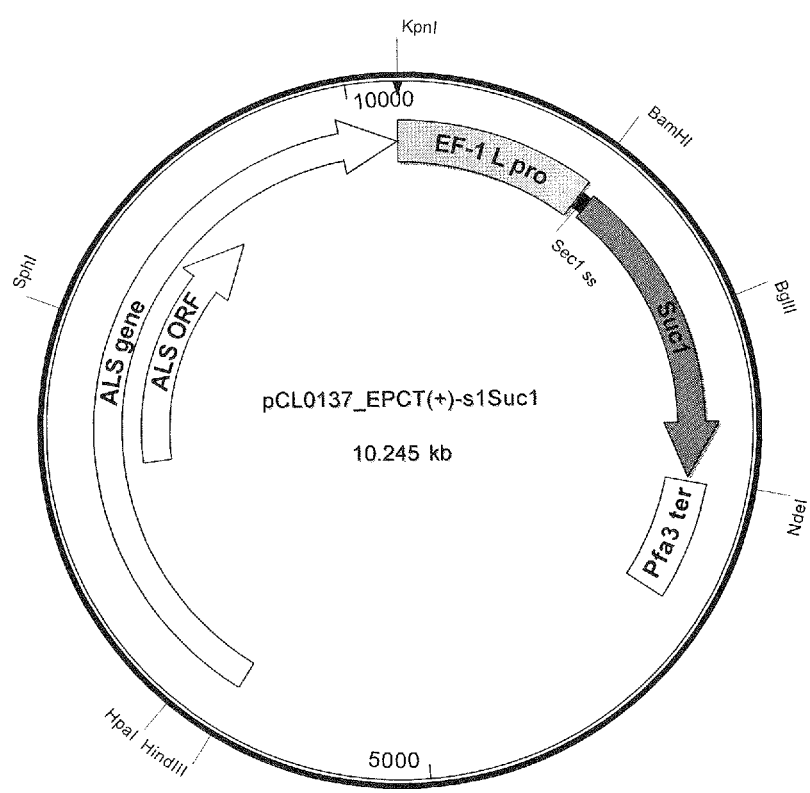
FIG. 45 shows a plasmid map of pCL0137 EPCT(+)-s1Suc1, also termed pCL0137.

The mature form of the Suc1 invertase protein from the fungus *Aspergillus niger* (GenBank Accession No. S33920) was codon-optimized for expression in *Schizochytrium* using the *Schizochytrium* codon usage table of FIG. 42 (codon optimization performed by Blue Heron Biotechnology, Bothell, Wash.). The codon optimized sequence was synthesized and the resulting polynucleotide sequence was fused to a polynucleotide sequence encoding the *Schizochytrium* Sec1 signal peptide ("Sec1 ss") as an N-terminal leader in place of the endogenous signal peptide. The resulting coding region of the "s1Suc1" nucleic acid sequence (SEQ ID NO:75) is shown in FIG. 44. This codon-optimized s1Suc1 polynucleotide was cloned to the vector pCL0120 using the 5' and 3° restriction sites BamHI and NdeI for insertion and ligation according to standard techniques. A plasmid map of the resulting vector, pCL0137, is shown in FIG. 45. Wild-type strain *Schizochytrium* sp. ATCC 20888 was transformed with this vector and the resulting clones were selected on solid SSFM media containing SMM. SMM-resistant clones were then re-plated to SSFM solid media containing sucrose as a sole carbon source to assay for growth. Depending on the transformation experiment, between 50% and 90% of the SMM-resistant primary transformants were capable of growth on sucrose media.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A recombinant nucleic acid molecule comprising:
   (a) a polynucleotide sequence having at least 90% sequence identity to the polynucleotide sequence of SEQ ID NO:43; or
   (b) a polynucleotide sequence that is fully complementary to the polynucleotide sequence of (a).

2. The recombinant nucleic acid molecule of claim 1, wherein the polynucleotide sequence has at least 95% sequence identity to the polynucleotide sequence of SEQ ID NO:43.

3. The recombinant nucleic acid molecule of claim 1, wherein the polynucleotide sequence is SEQ ID NO:43.

4. The recombinant nucleic acid molecule of claim 1 or claim 2, wherein the % sequence identity can be found over a sequence of at least 10 nucleotides of SEQ ID NO:43.

5. The recombinant nucleic acid molecule of claim 1 or claim 2, wherein the % sequence identity can be found over a sequence of at least 20 nucleotides of SEQ ID NO:43.

6. The recombinant nucleic acid molecule of claim 1 or claim 2, wherein the % sequence identity can be found over a sequence of at least 50 nucleotides of SEQ ID NO:43.

7. The recombinant nucleic acid molecule of claim 1 or claim 2, wherein the % sequence identity can be found over a sequence of at least 100 nucleotides of SEQ ID NO:43.

8. The recombinant nucleic acid molecule of claim 1 or claim 2, wherein the % sequence identity can be found over a sequence of at least 300 nucleotides of SEQ ID NO:43.

9. The recombinant nucleic acid molecule of claim 1 or claim 2, wherein the % sequence identity can be found over the entire length of SEQ ID NO:43.

10. The recombinant nucleic acid molecule of claim 1, wherein the recombinant nucleic acid molecule is a vector.

11. The recombinant nucleic acid molecule of claim 1, wherein the polynucleotide sequence is operably linked to a polynucleotide sequence encoding a protein.

12. The recombinant nucleic acid molecule of claim 11, wherein the protein is operably linked to a secretion signal.

13. A host cell comprising the recombinant nucleic acid molecule of claim 1.

14. The host cell of claim 13, wherein the host cell is a member of the order Thraustochytriales.

15. The host cell of claim 14, wherein the host cell is a *Schizochytrium* or a *Thraustochytrium*.

16. A method for production of a protein encoded by a polynucleotide that is operably linked to the polynucleotide of claim 1, comprising:
   (a) culturing a recombinant microorganism of the order Thraustochytriales in a medium, wherein the recombinant microorganism comprises recombinant nucleic acid molecule of claim 11 or claim 12;
   (b) producing the protein made in step (a); and
   (c) isolating the protein produced in step (b).

17. The method of claim 16, wherein the protein is recovered from an isolated Thraustochytriales biomass.

18. The method of claim 16, wherein the protein accumulates in the microorganism.

19. The method of claim 16, wherein the protein accumulates in a membrane of the microorganism.

20. The method of claim 16, wherein the protein is recovered from the culture medium.

21. The method of claim 16, wherein the protein is secreted.

22. The recombinant nucleic acid molecule of claim 10, wherein said vector is deposited under ATCC Accession No. PTA-9616.

* * * * *